US010106799B2

(12) United States Patent
Otte et al.

(10) Patent No.: US 10,106,799 B2
(45) Date of Patent: *Oct. 23, 2018

(54) STRINGENT SELECTABLE MARKERS

(71) Applicant: CellaGenics B.V., Amsterdam (NL)

(72) Inventors: Arie Pieter Otte, Amersfoort (NL); Henricus Johannes Maria Van Blokland, Wijde Wormer (NL); John Antonius Verhees, Wageningen (NL)

(73) Assignee: CELLAGENICS B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,380

(22) Filed: Feb. 8, 2016

(65) Prior Publication Data

US 2016/0160221 A1    Jun. 9, 2016

Related U.S. Application Data

(63) Continuation of application No. 13/378,006, filed as application No. PCT/NL2010/050367 on Jun. 15, 2010, now Pat. No. 9,284,563.

(60) Provisional application No. 61/187,022, filed on Jun. 15, 2009.

(51) Int. Cl.
| C12N 15/65 | (2006.01) |
| C12N 15/67 | (2006.01) |
| C12N 15/52 | (2006.01) |
| C12N 15/85 | (2006.01) |

(52) U.S. Cl.
CPC ............. *C12N 15/65* (2013.01); *C12N 15/52* (2013.01); *C12N 15/67* (2013.01); *C12N 15/85* (2013.01); *C12Y 404/01001* (2013.01); *C12N 2840/102* (2013.01); *C12N 2840/206* (2013.01)

(58) Field of Classification Search
CPC ... C12N 2840/102; C12N 15/67; C12N 15/65
See application file for complete search history.

(56) References Cited

U.S. PATENT DOCUMENTS

| 4,965,196 | A | 10/1990 | Levinson et al. |
| 6,027,915 | A | 2/2000 | Morris et al. |
| 6,110,707 | A | 8/2000 | Newgard et al. |
| 6,165,715 | A | 12/2000 | Collins et al. |
| 7,041,483 | B2 | 5/2006 | Rothnagel et al. |
| 2002/0019049 | A1 | 2/2002 | Lok |
| 2005/0106580 | A1* | 5/2005 | Enenkel ......... C12Y 207/01095 435/6.16 |
| 2006/0172382 | A1 | 8/2006 | Otte et al. |
| 2008/0286824 | A1 | 11/2008 | Dupraz et al. |

FOREIGN PATENT DOCUMENTS

| WO | WO-01/32901 A1 | 5/2001 |
| WO | WO-03/004704 A2 | 1/2003 |
| WO | WO-03/106674 A2 | 12/2003 |
| WO | WO-03/106684 A2 | 12/2003 |
| WO | WO-2006/005718 A2 | 1/2006 |
| WO | WO-2006/048459 A2 | 5/2006 |
| WO | WO-2006/123097 A2 | 11/2006 |
| WO | WO-2007/096399 A2 | 8/2007 |
| WO | WO-2010/147462 A2 | 12/2010 |

OTHER PUBLICATIONS

Hayden et al. Comparative genomic analysis of novel conserved peptide upstream open reading frames in *Drosophila melanogaster* and other dipteran species. BMC Genomics, vol. 9, 61, Feb. 2008, printed as pp. 1/14-14/14. (Year: 2008).*
Bergdoll, et al., "All in the family: Structural and evolutionary relationships among three modular proteins with diverse functions and variable assembly", Protein Science, (1998), vol. 7, pp. 1661-1670, XP002596221.
Database EMBL [Online] Dec. 19, 2011 (Dec. 19, 2011), "*Homo sapiens* RPL32 gene for ribosomal protein L32, complete cds and sequence.", XP002663329, retrieved from EBI accession No. EM_HUM:AB061831.
Database EMBL [online] Apr. 7, 2000 (Apr. 7, 2000), "*Homo sapiens* chromosome 3 clone RP11-767C1 map 3p, complete sequence.", XP002663328, retrieved from EBI accession No. EM_HUM:AC034198.
Dumas, et al., "Crystal structure and site-directed mutagenesis of a bleomycin resistance protein and their significance for drug sequestering," The European Molecular Biology Organization (EMBO) Journal, (1994) vol. 13, No. 11, pp. 2483-2492, XP002596206.
Fan, et al. "Development of a highly-efficient CHO cell line generation system with engineered SV40E promoter", Journal of Biotechnology, 2013, vol. 168, pp. 652-658.
Genbank Accession AC018843.4, 2001, accessed on Apr. 19, 2014; http://www.ncbi.nlm.nih.gov/nucleotide/13899386?report=genbank &log$=nuclalign&blast_rank=1&RID=N59Y1JJS01R.

(Continued)

*Primary Examiner* — Jennifer Dunston
(74) *Attorney, Agent, or Firm* — Gilberto M. Villacorta; Sunit Talapatra; Foley & Lardner LLP

(57) ABSTRACT

The present invention relates to nucleic acid constructs comprising selectable marker genes in a multicistronic transcription unit for use in the generation and selection of eukaryotic host cells for expression of a gene product of interest. For increased stringency of selection, the coding sequence of the selectable marker may be directed preceded by a relatively short functional open reading frame to reduce the efficiency of translation of the selectable marker, and/or the amino acid sequence of the selectable marker may comprise one or more mutations that reduce the level of resistance provide by the mutated marker as compared to its wild type counterpart. The invention further relates to methods for generating eukaryotic host cells for expression of a gene product of interest, wherein these nucleic acid constructs are used, and to methods for producing a gene product of interest wherein thus generated host cells are applied.

14 Claims, 21 Drawing Sheets

Specification includes a Sequence Listing.

(56) References Cited

OTHER PUBLICATIONS

Hoeksema, F. et al: "Placing the RPL32 Promoter Upstream of a Second Promoter Results in a Strongly Increased Number of Stably Transfected Mammalian Cell Lines That Display High Protein Expression Levels", Biotechnology Research International, vol. 2011, 492875, Dec. 19, 2010 (Dec. 19, 2010), XP002663330.
International Search Report for PCT/NL2011/050593—dated Nov. 29, 2011.
Kane, et al. "MDR1 bicistronic vectors: analysis of selection stringency, amplified gene expression, and vector stability in cell lines", Biochemical Pharmacology, 2001, vol. 62, pp. 693-704.
Kozak, "Regulation of translation via mRNA structure in prokaryotes and eukaryotes", GENE (2005), pp. 13-37.
Kozak, Constraints on reinitation of translation in mammals. Nucleic Acids Research, vol. 29, No. 24, pp. 5226-5232, 2001.
Levine, et al., "Efficient gene expression in mammalian cells from a dicistronic transcriptional unit in an improved retroviral vector," Gene, (1991), vol. 108, pp. 167-174, XP0023541477.
McCormick, et al. "Inducible Expression of Amplified Human Beta Interferon Genes in CHO Cells", Molecular and Cellular Biology (Jan. 1984), vol. 4, No. 1, pp. 166-172.
Mulsant, et al., "Phleomycin Resistance as a Dominant Selectable Marker in CHO Cells," Somatic Cell and Molecular Genetics, (1988), vol. 14, No. 3, pp. 243-252, XP009137462.
Needham et al., "Further Development of the Locus Control Region/Murine Erythroleukemia Expression System: High Level Expression and Characterization of Recombinant Human Calcitonin Receptor", 1995, Protein Expression and Purification, vol. 6, pp. 124-131.
Otte et al, "Various Expression-Augmenting DNA Elements Benefit from STAR-Select, a Novel High Stringency Selection System for Protein Expression", 2007, Biotechnol. Prog., vol. 23, pp. 801-807.
Perry, Robert P.: "The architecture of mammalian ribosomal protein promoters", BMC Evolutionary Biology, vol. 5, No. 15, Feb. 13, 2005 (Feb. 13, 2005), pp. 1-16, XP002601726, Biomed Central Ltd., London, GB.
Rees et al., "Bicistronic Vector for the Creation of Stable Mammalian Cell Lines that Predisposes All Antibiotic-Resistant Cells to Express Recombinant Protein", Jan. 1996, BioTechniques, vol. 20, pp. 102-110.
International Search Report in PCT/NL2010/050367 dated Mar. 10, 2011.
Van Blokland, et al. "A novel, high stringency selection system allows screening of fews clones for high protein expression", Journal of Biotechnology, 2007, vol. 128, pp. 237-245.
Yan, et al. "A mini-IRES sequence for stringent selection of high producers", J. Biosci., Jun. 2013, vol. 38, No. 2, pp. 245-249.
Yoshihama et al., "The human ribosomal protein genes: sequencing and comparative analysis of 73 genes." Genome Research, 2002, vol. 12, No. 3, pp. 379-390.
Aldrich et al., "Improved bicistronic mammalian expression vectors using expression augmenting sequence element (EASE)", Cytotechnology, 1998, vol. 28, pp. 9-17.
Kim et al., "Improved recombinant gene expression in CHO cells using matrix attachment regions", Journal of Biotechnology, 2004, vol. 107, pp. 95-105.
Kwaks et al., "Chapter 2: Identification of anti-repressor elements that confer high and stable protein production in mammalian cells", Nature Biotechnolgy, 2003, vol. 21, No. 5, pp. 553-558.
Ng et al., "Application of destabilizing sequences on selection marker for improved recombinant protein productivity in CHO-DG44", Metabolic Engineering, 2007, vol. 9, pp. 304-316.
Niwa et al., "Efficient selection for high-expression transfectants with a novel eukaryotic vector", Gene, 1991, vol. 108, pp. 193-200.
Sautter et al., "Selection of high-producing CHO cells using NPT selection marker with reduced enzyme activity", Biotechnology and Bioengineering, Mar. 2005, vol. 89, No. 5, pp. 530-538.
Williams et al., "CpG-island fragments from the HNRPA2BI/CBX3 genomic locus reduce silencing and enhance transgene expression from the hCMV promoter/enhancer in mammalian cells", BMC Biotechnology, 2005, vol. 5, No. 17, pp. 1-9.

* cited by examiner

Fig 2
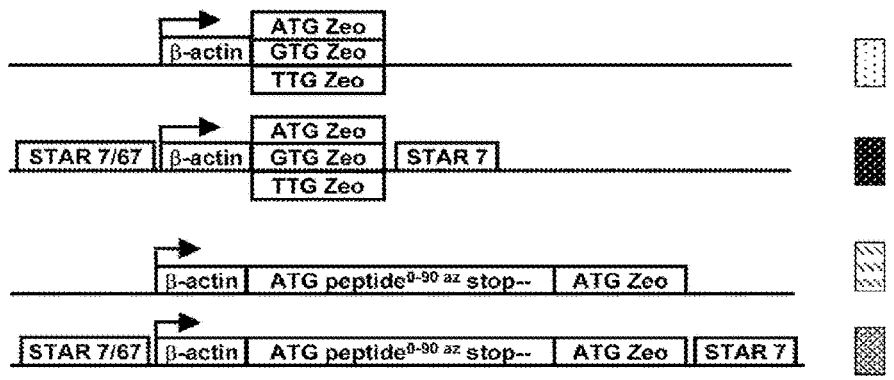
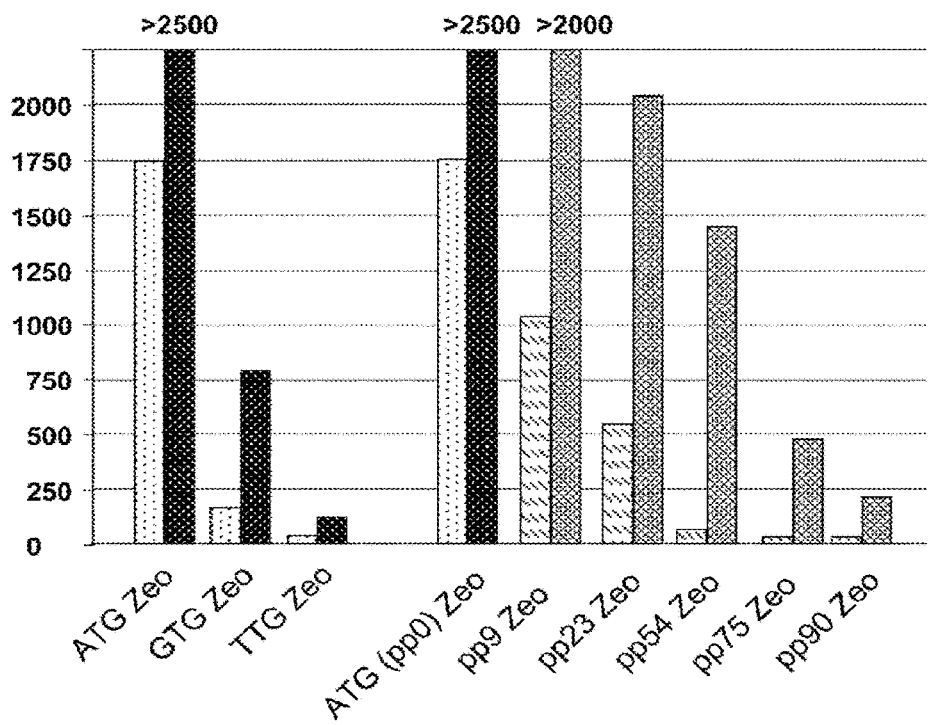

Fig 3
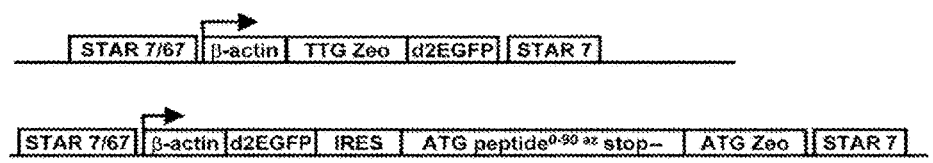
Mean d2GFP expression levels in Zeo^R colonies
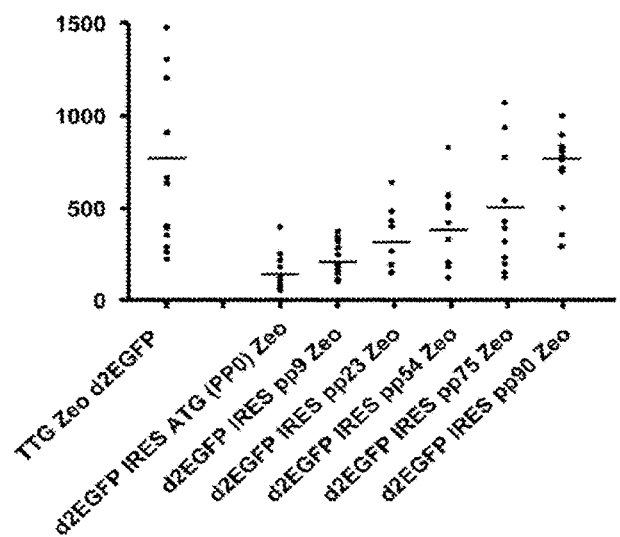

Fig 6

```
WT      makltsavpv ltardvagav efwtdrlgfs rdfveddfag      40
C  9    ---------C- ---------- ---------- ----------
Q  9    ---------Q- ---------- ---------- ----------
T  9    ---------T- ---------- ---------- ----------
V 94    ---------- ---------- ---------- ----------

EPP 14  --------A- -A-------- ---------- -------G--
EPP  7  ---------- ---------- -------R-- ----------
EPP 15  ---------- ---P------ ---------- ----------
EPP 28  ---------- ---------- -Y--G----- ----------
EPP 16  ---------- ---------- ---------- ---L------
EPP  5  ---------- ---------- G--------- ----------
EPP 66  ---------- ---------- ---------- ----------

WT      vvrddvtlfi savqdqvvpd ntlawvwvrg ldelyaewse      80
C  9    ---------- ---------- ---------- ----------
Q  9    ---------- ---------- ---------- ----------
T  9    ---------- ---------- ---------- ----------
V 94    ---------- ---------- ---------- ----------

EPP 14  ---------- ---------- ---------- ----------
EPP  7  ---------- ---------- ---------- ---G------
EPP 15  ---------- ---------- ---------- ---K------
EPP 28  ---------- ---------- ---------- ----------
EPP 16  ---------- ---------- ---------- ----------
EPP  5  ---------- ---------- ---------- ------T---
EPP 66  ---------- ---------- ---------- ----------

WT      vvstnfrdas gpamteigeq pwgrefalrd pagncvhfva eeqd  124
C  9    ---------- ---------- ---------- ---------- ----
Q  9    ---------- ---------- ---------- ---------- ----
T  9    ---------- ---------- ---------- ---------- ----
V 94    ---------- -----V---- ---------- ---------- ----

EPP 14  ---------- ---------- ---------- ---------- ----
EPP  7  ---------- ---------- ---------- ---------- ----
EPP 15  ------G--- ---------- ---------- ---------- ----
EPP 28  ---------- ---------- ---------- ---------- ----
EPP 16  ---------- ---------- ---------- ---------- ----
EPP  5  ---------- ---------- ---------- ---------- ----
EPP 66  -E-------- ---------- ---------- ---------- ----
```

Fig 9
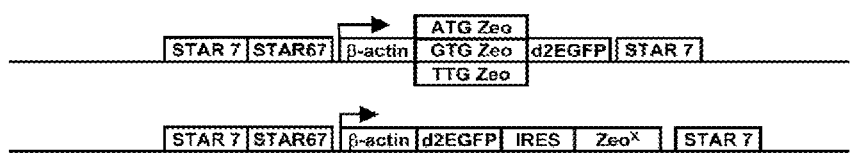
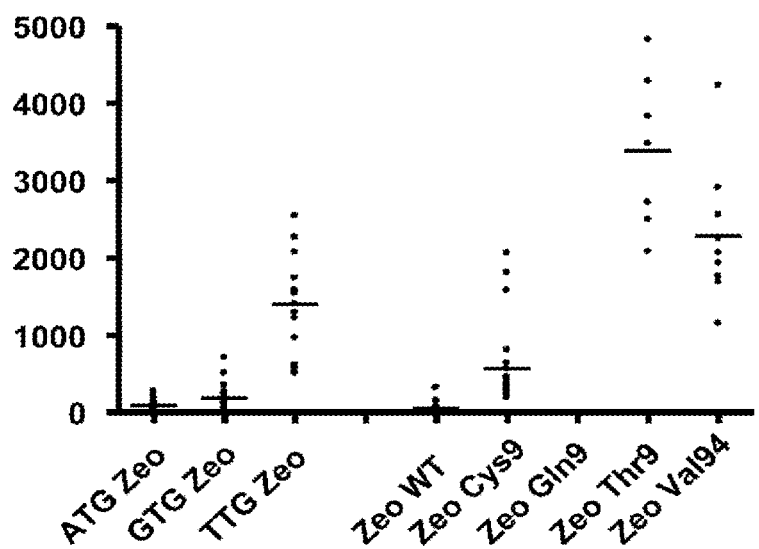
Mean d2EGFP fluorescence in Zeo^R colonies

Fig 17
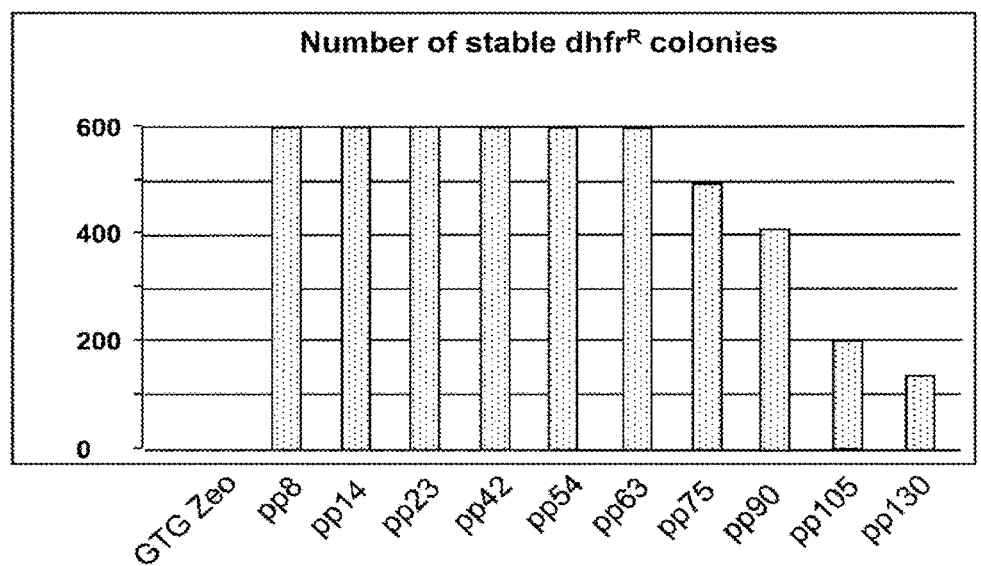

Fig 18
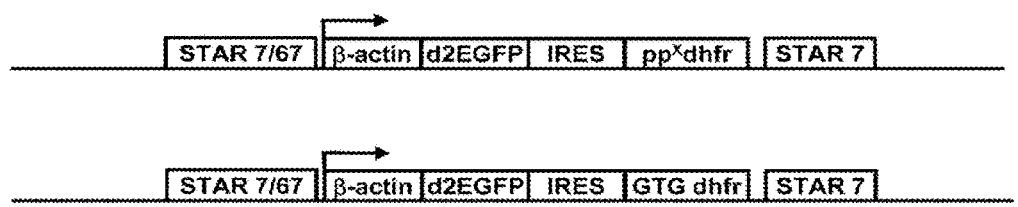
Mean d2GFP expression levels in dhfr^R colonies
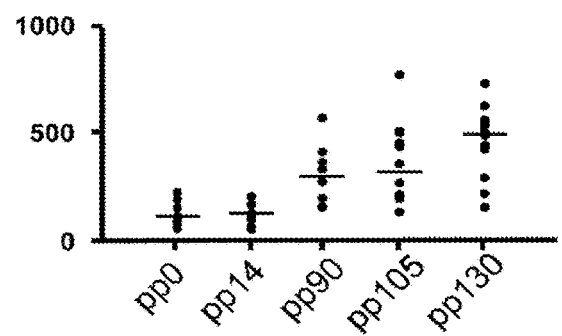

SEQUENCE LISTING

```
<160> NUMBER OF SEQ ID NOS: 48

<210> SEQ ID NO 1
<211> LENGTH: 375
<212> TYPE: DNA
<213> ORGANISM: Artificial Sequence
<220> FEATURE:
<223> OTHER INFORMATION: Description of Artificial Sequence: Synthetic
      wt Zeo resistance gene

<400> SEQUENCE: 1
atggccaagt tgaccagtgc cgttccggtg ctcaccgcgc gcgacgtcgc cggagcggtc        60
gagttctgga ccgaccggct cgggttctcc cgggacttcg tggaggacga cttcgccggt       120
gtggtccggg acgacgtgac cctgttcatc agcgcggtcc aggaccaggt ggtgccggac       180
aacaccctgg cctgggtgtg ggtgcgcggc ctggacgagc tgtacgccga gtggtcggag       240
gtcgtgtcca cgaacttccg ggacgcctcc gggccggcca tgaccgagat cggcgagcag       300 ccgtggggc gggagttcgc cctgcgcgac ccggccggca actgcgtgca cttcgtggcc       360
gaggagcagg actga                                                       375

<210> SEQ ID NO 2
<211> LENGTH: 600
<212> TYPE: DNA
<213> ORGANISM: Artificial Sequence
<220> FEATURE:
<223> OTHER INFORMATION: Description of Artificial Sequence: Synthetic
      wt puromycin resistance gene

<400> SEQUENCE: 2
atgaccgagt acaagcccac ggtgcgcctc gccacccgcg acgacgtccc cagggccgta        60
cgcaccctcg ccgccgcgtt cgccgactac cccgccacgc gccacaccgt cgatccggac       120
cgccacatcg agcgggtcac cgagctgcaa gaactcttcc tcacgcgcgt cgggctcgac       180
atcggcaagg tgtgggtcgc ggacgacggc gccgcggtgg cggtctggac cacgccggag       240
agcgtcgaag cgggggcggt gttcgccgag atcgcccgc gcatggccga gttgagcggt        300
tcccggctgg ccgcgcagca acagatggaa ggcctcctgg cgccgcaccg gcccaaggag       360
cccgcgtggt tcctggccac cgtcggcgtc tcgcccgacc accagggcaa gggtctgggc       420
agcgccgtcg tgctccccgg agtggaggcg gccgagcgcg ccggggtgcc cgccttcctg       480
gagacctccg cgccccgcaa cctccccttc tacgagcggc tcggcttcac cgtcaccgcc       540
gacgtcgagt gcccgaagga ccgcgcgacc tggtgcatga cccgcaagcc cggtgcctga       600

<210> SEQ ID NO 3
<211> LENGTH: 399
<212> TYPE: DNA
```

<213> ORGANISM: Artificial Sequence
<220> FEATURE:
<223> OTHER INFORMATION: Description of Artificial Sequence: Synthetic wt blasticidin resistance gene

<400> SEQUENCE: 3

```
atggccaagc ctttgtctca agaagaatcc accctcattg aaagagcaac ggctacaatc      60
aacagcatcc ccatctctga agactacagc gtcgccagcg cagctctctc tagcgacggc     120
cgcatcttca ctggtgtcaa tgtatatcat tttactgggg accttgtgc agaactcgtg      180
gtgctgggca ctgctgctgc tgcggcagct ggcaacctga cttgtatcgt cgcgatcgga     240
aatgagaaca gggcatctt gagcccctgc ggacggtgcc gacaggtgct ctcgatctg       300
catcctggga tcaaagccat agtgaaggac agtgatggac agccgacggc agttgggatt     360
cgtgaattgc tgccctctgg ttatgtgtgg gagggctaa                            399
```

<210> SEQ ID NO 4
<211> LENGTH: 1143
<212> TYPE: DNA
<213> ORGANISM: Artificial Sequence
<220> FEATURE:
<223> OTHER INFORMATION: Description of Artificial Sequence: Synthetic wt hygromycin resistance gene

<400> SEQUENCE: 4

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag ggtcgatgcg acgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc ggaggcaaag    1020
gaattcggga gatggggag ctaactgaa acacggaagg agacaatacc ggaaggaacc     1080
cgcgctatga cggcaataaa agacagaat aaaacgcacg ggtgttgggt cgtttgttca     1140
taa                                                                 1143
```

<210> SEQ ID NO 5
<211> LENGTH: 804
<212> TYPE: DNA
<213> ORGANISM: Artificial Sequence
<220> FEATURE:
<223> OTHER INFORMATION: Description of Artificial Sequence: Synthetic neomycin resistance gene

<400> SEQUENCE: 5

```
atgggatcgg ccattgaaca agatggattg cacgcaggtt ctccggccgc ttgggtggag    60
aggctattcg gctatgactg ggcacaacag acaatcggct gctctgatgc cgccgtgttc   120
cggctgtcag cgcaggggcg cccggttctt tttgtcaaga ccgacctgtc cggtgccctg   180
aatgaactgc aggacgaggc agcgcggcta tcgtggctgg ccacgacggg cgttccttgc   240
gcagctgtgc tcgacgttgt cactgaagcg ggaagggact ggctgctatt gggcgaagtg   300
ccggggcagg atctcctgtc atctcacctt gctcctgccg agaaagtatc catcatggct   360
gatgcaatgc ggcggctgca tacgcttgat ccggctacct gcccattcga ccaccaagcg   420
aaacatcgca tcgagcgagc acgtactcgg atggaagccg gtcttgtcga tcaggatgat   480
ctggacgaag agcatcaggg gctcgcgcca gccgaactgt tcgccaggct caaggcgcgc   540
atgcccgacg gcgatgatct cgtcgtgacc catggcgatg cctgcttgcc gaatatcatg   600
gtggaaaatg gccgcttttc tggattcatc gactgtggcc ggctgggtgt ggcggaccgc   660
tatcaggaca tagcgttggc tacccgtgat attgctgaag agcttggcgg cgaatgggct   720
gaccgcttcc tcgtgcttta cggtatcgcc gctcccgatt cgcagcgcat cgccttctat   780
cgccttcttg acgagttctt ctga                                          804
```

<210> SEQ ID NO 6
<211> LENGTH: 564
<212> TYPE: DNA
<213> ORGANISM: Artificial Sequence
<220> FEATURE:
<223> OTHER INFORMATION: Description of Artificial Sequence: Synthetic mouse DHFR gene

<400> SEQUENCE: 6

```
atggttcgac cattgaactg catcgtcgcc gtgtcccaaa atatggggat tggcaagaac    60
ggagacctac cctggcctcc gctcaggaac gagttcaagt acttccaaag aatgaccaca   120
acctcttcag tggaaggtaa acagaatctg gtgattatgg gtaggaaaac ctggttctcc   180
attcctgaga gaatcgacc tttaaaggac agaattaata tagttctcag tagagaactc   240
aaagaaccac cacgaggagc tcattttctt gccaaaagtt tggatgatgc cttaagactt   300
attgaacaac cggaattggc aagtaaagta gacatggttt ggatagtcgg aggcagttct   360
gtttaccagg aagccatgaa tcaaccaggc cacctcagac tctttgtgac aaggatcatg   420
caggaatttg aaagtgacac gttttttccca gaaattgatt ggggaaata taaacttctc   480
ccagaatacc caggcgtcct ctctgaggtc caggaggaaa aaggcatcaa gtataagttt   540
gaagtctacg agaagaaaga ctaa                                          564
```

<210> SEQ ID NO 7
<211> LENGTH: 1121
<212> TYPE: DNA
<213> ORGANISM: Artificial Sequence
<220> FEATURE:
<223> OTHER INFORMATION: Description of Artificial Sequence: Synthetic human glutamine synthase gene

<400> SEQUENCE: 7

```
atgaccacct cagcaagttc ccacttaaat aaaggcatca gcaggtgta catgtccctg    60
cctcagggtg agaaagtcca ggccatgtat atctggatcg atggtactgg agaaggactg   120
cgctgcaaga cccggaccct ggacagtgag cccaagtgtg tggaagagtt gcctgagtgg   180
```

```
aatttcgatg gctccagtac tttacagtct gagggttcca acagtgacat gtatctcgtg    240
cctgctgcca tgtttcggga ccccttccgt aaggacccta acaagctggt gttatgtgaa    300
gttttcaagt acaatcgaag gcctgcagag accaatttga ggcacacctg taaacggata    360
atggacatgg tgagcaacca gcacccctgg tttggcatgg agcaggagta tcccctcatg    420
gggacagatg ggcacccctt tggttggcct tccaacggct tcccagggcc cagggtcca     480 tattactgtg tgtgtgggagc agacagagcc tatggcaggg acatcgtgga ggcccattac   540
cgggcctgct tgtatgctgg agtcaagatt gcggggacta atgccgaggt catgcctgcc    600
cagtgggaat ttcagattgg accttgtgaa ggaatcagca tggagatca tctctgggtg     660 gcccgtttca tcttgcatcg tgtgtgtgaa gactttggag tgatagcaac ctttgatcct    720
aagcccattc ctgggaactg gaatggtgca ggctgccata ccaacttcag caccaaggcc    780
atgcgggagg agaatggtct gaagtacatc gaggaggcca ttgagaaact aagcaagcgg    840
caccagtacc acatccgtgc ctatgatccc aagggaggcc tggacaatgc ccgacgtcta    900
actggattcc atgaaacctc caacatcaac gacttttctg gtggtgtagc caatcgtagc    960
gccagcatac gcattccccg gactgttggc caggagaaga agggttactt tgaagatcgt    1020
cgcccctctg ccaactgcga ccccttttcg gtgacagaag ccctcatccg cacgtgtctt    1080
ctcaatgaaa ccggcgatga gcccttccag tacaaaaatt a                         1121
```

```
<210> SEQ ID NO 8
<211> LENGTH: 1122
<212> TYPE: DNA
<213> ORGANISM: Artificial Sequence
<220> FEATURE:
<223> OTHER INFORMATION: Description of Artificial Sequence: Synthetic
      mouse glutamine synthase gene

<400> SEQUENCE: 8
atggccacct cagcaagttc ccacttgaac aaaggcatca agcaaatgta catgtccctg     60
ccccagggtg agaaagtcca agccatgtat atctgggttg atggtaccgg agaaggactg   120
cgctgcaaga cccgtaccct ggactgtgag cccaagtgtg tggaagagtt acctgagtgg   180
aactttgatg gctctagtac cttttcagtct gaaggctcca acagcgacat gtacctccat   240
cctgttgcca tgtttcgaga ccccttccgc agagacccca acaagctggt gctatgtgaa    300
gttttcaagt ataaccggaa acctgcagag accaacttga ggcacatctg taaacggata   360
atggacatgg tgagcaacca gcacccctgg tttggaatgg agcaggaata tactcttatg    420
ggaacagacg gccacccatt tggttggcct tccaatggct tccctggacc ccaaggcccg    480
tattactgcg tgtgtgggagc agacaaggcc tacggcaggg acatcgtgga ggctcactac   540
cgggcctgct tgtatgctgg agtcaagatt acggggacaa atgcggaggt tatgcctgcc    600
cagtgggaat tccaaatagg accctgtgag gggatccgaa tggagatca tctttggata    660 gcccgtttta tcttgcatcg ggtgtgcgaa gactttgggg tgatagcaac ctttgacccc    720
aagcccattc cagggaactg gaatgttgca ggctgccata ccaacttcag caccaaggcc    780
atgcgggagg agaatggtct gaagtgcatt gaggaggcca ttgacaaact gagcaagagg    840
caccagtacc acattcgcgc ctacgatccc aaggggggcc tggacaatgc ccgtgctctg    900
actggattcc acgaaacctc caacatcaac gacttttctg ctggtgttgc aaccgcggt    960 gccagtatcc gcattccccg gactgtcggc caggagaaga agggctactt tgaagaccgt    1020
cgccttcgtg ccaattgtga cccсctatgcg gtgacagaag ccatcgtccg cacgtgtctc    1080
```
ctcaacgaaa caggcgacga acccttccaa tacaagaact aa            1122

<210> SEQ ID NO 9
<211> LENGTH: 1221
<212> TYPE: DNA
<213> ORGANISM: Artificial Sequence
<220> FEATURE:
<223> OTHER INFORMATION: Description of Artificial Sequence: Synthetic
      cystathione gamma-lyase gene

<400> SEQUENCE: 9

```
atgggccagg aaaaagacgc ctcctcacaa ggtttcctgc cacacttcca acatttcgcc     60
acgcaggcga tccatgtggg ccaggacccg gagcaatgga cctccagggc tgtagtgccc    120
cccatctcac tgtccaccac gttcaagcaa ggggcgcctg ccagcactc gggttttgaa     180
tatagccgtt ctggaaatcc cactaggaat tgccttgaaa aagcagtggc agcactggat    240
ggggctaagt actgtttggc ctttgcttca ggtttagcag ccactgtaac tattacccat    300
ctttttaaaag caggagacca aattatttgt atggatgatg tgtatggagg tacaaacagg    360
tacttcaggc aagtggcatc tgaatttgga ttaaagattt cttttgttga ttgttccaaa    420
atcaaattac tagaggcagc aattacacca gaaaccaagc tcgtttggat cgaaaccccc    480
acaaacccca cccagaaggt gattgacatt gaaggctgtg cacatattgt ccataagcat    540
ggagacatta ttttggtcgt ggataacact tttatgtcac catatttcca gcgcccttg     600
gctctgggag ctgatatttc tatgtattct gcaacaaaat acatgaatgg ccacagtgat    660
gttgtaatgg gcctggtgtc tgttaattgt gaaagccttc ataatagact tcgtttcttg    720
caaaactctc ttggagcagt tccatctcct attgattgtt acctctgcaa tcgaggtctg    780
aagactctac atgtccgaat ggaaaagcat ttcaaaaacg gaatggcagt tgcccagttc    840
ctggaatcta atccttgggt agaaaaggtt atttatcctg ggctgccctc tcatccacag    900
catgagttgg tgaagcgtca gtgcacaggt tgcacaggga tggtcacctt ttatattaag    960
ggcactcttc agcacgctga gattttcctc aagaacctaa agctatttac tctggccgag   1020
agcttgggag gattcgagag ccttgctgag cttccggcaa tcatgactca tgcatcagtt   1080
cttaagaatg acagagatgt cccttggaatt agtgacacac tgattcgact ttctgtgggc   1140
ttagaggatg aggaagacct actggaagac ctagatcagg ctttgaaggc agcacaccct   1200
ccaagtggga ttcacagcta g                                             1221
```

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      wild type zeocin resistance protein

<400> SEQUENCE: 10

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
            85                  90                  95

Ile Gly Glu Gln Pro Trp Gly Arg Glu Phe Ala Leu Arg Asp Pro Ala
        100                 105                 110

Gly Asn Cys Val His Phe Val Ala Glu Glu Gln Asp
        115                 120

<210> SEQ ID NO 11
<211> LENGTH: 3500
<212> TYPE: DNA
<213> ORGANISM: Homo sapiens
<220> FEATURE:
<223> OTHER INFORMATION: Human beta-actin promoter

<400> SEQUENCE: 11

| | |
|---|---|
| gccccagtga cagctccgaa agctccctta cagggcaaag ttcccaagca cagaagagaa | 60 |
| cctgttcact tctcccctgc tcggcccgcc cctggccag gcacctctac ttcctctttt | 120 |
| cctgctccgc tgcttgcttt ctctcttcag ctcctccctg ccctcaccc caggctgctc | 180 |
| ggccacctcc aacctgccac ctgaggacac ccaggcagtc actcattcaa cagcgaggag | 240 |
| ccctggggtg ggtgtagtgg aaggagtgg gggtgacgga gaccctggga gggctcgcag | 300 |
| cctggtggct gaggcccagt tctaaatgcc agctgcaagc cttggtctga ggtagggagg | 360 |
| aaggcgtggc tgcagaggct aaaacgcttc cccaagagg ggctttctgg gatgggactt | 420 |
| gaagggtgca taggagagca ctaggaagtg ccgctgcag acagagggaa ccacaagcca | 480 |
| ggaggacagg ccaggaatgc tgcagcccgg ggcggggtgg ggctggagct cctgtctctt | 540 |
| ggccagctga atggaggccc agtggcaaca caggtcctgc ctggggatca ggtctgctct | 600 |
| gcaccccacc ttgctgcctg agccgccca cctgacaacc tctcatccct gctctgcaga | 660 |
| tccggtccca tccccactgc ccaccccacc ccccagcac tccacccagt tcaacgttcc | 720 |
| acgaaccccc agaaccagcc ctcatcaaca ggcagcaaga agggccccc gcccatcgcc | 780 |
| ccacaacgcc agccgggtga acgttggcag gtcctgaggc agctggcaag acgcctgcag | 840 |
| ctgaaagata caaggccagg acaggacag tcccatcccc aggaggcagg gagtatacag | 900 |
| gctggggaag tttgcccttg cgtggggtgg tgatggagga ggctcagcaa gtcttctgga | 960 |
| ctgtgaacct gtgtctgcca ctgtgtgctg gtggtggtc atctttccca ccaggctgtg | 1020 |
| gcctctgcaa ccttcaaggg aggagcaggt cccattggct gagcacagcc ttgtaccgtg | 1080 |
| aactggaaca agcagcctcc ttcctggcca caggttccat gtccttatat ggactcatct | 1140 |
| ttgcctattg cgacacacac tcagtgaaca cctactacgc gctgcaaaga gccccgcagg | 1200 |
| cctgaggtgc ccccacctca ccactcttcc tattttgtg taaaaatcca gcttcttgtc | 1260 |
| accacctcca aggaggggga ggaggaggaa ggcaggttcc tctaggctga gccgaatgcc | 1320 |
| cctctgtggt cccacgccac tgatcgctgc atgcccacca cctgggtaca cacagtctgt | 1380 |
| gattcccgga gcagaacgga ccctgcccac ccggtcttgt gtgctactca gtggacagac | 1440 |
| ccaaggcaag aaaggtgac aaggacaggg tcttcccagg ctggctttga gttcctagca | 1500 |
| ccgccccgcc cccaatcctc tgtggcacat ggagtcttgg tccccagagt ccccagcgg | 1560 |
| cctccagatg gtctgggagg gcagttcagc tgtggctgcg catagcagac atacaacgga | 1620 |
| cggtgggccc agacccaggc tgtgtagacc cagccccccc gccccgcagt gcctaggtca | 1680 |
| cccactaacg ccccaggcct tgtcttggct gggcgtgact gttaccctca aaagcaggca | 1740 |

```
gctccagggt aaaaggtgcc ctgccctgta gagcccacct tccttcccag ggctgcggct   1800
gggtaggttt gtagccttca tcacgggcca cctccagcca ctggaccgct ggcccctgcc   1860
ctgtcctggg gagtgtggtc ctgcgacttc taagtggccg caagccacct gactccccca   1920
acaccacact ctacctctca agcccaggtc tctccctagt gacccaccca gcacatttag   1980
ctagctgagc cccacagcca gaggtcctca ggccctgctt tcagggcagt tgctctgaag   2040
tcggcaaggg ggagtgactg cctggccact ccatgccctc caagagctcc ttctgcagga   2100
gcgtacagaa cccagggccc tggcacccgt gcagaccctg gcccacccca cctgggcgct   2160
cagtgcccaa gagatgtcca cactaggat gtcccgcgt gggtgggggg cccgagagac   2220
```

```
gggcaggccg ggggcaggcc tggccatgcg gggccgaacc gggcactgcc cagcgtgggg   2280
cgcgggggcc acgcgcgcg ccccagccc ccgggcccag cacccaagg cggccaacgc   2340 caaaactctc cctcctcctc ttcctcaatc tcgctctcgc tcttttttt tttcgcaaaa   2400 ggaggggaga gggggtaaaa aaatgctgca ctgtgcggcg aagccggtga gtgagcggcg   2460
cggggccaat cagcgtgcgc cgttccgaaa gttgcctttt atggctcgag cggccgcggc   2520
ggcgccctat aaaacccagc ggcgcgacgc gccaccaccg ccgagaccgc gtccgccccg   2580
cgagcacaga gcctcgcctt tgccgatccg ccgcccgtcc acacccgccg ccaggtaagc   2640
ccggccagcc gaccggggca ggcggctcac ggcccggccg caggcggccg cggcccttc   2700 gcccgtgcag agccgccgtc tgggccgcag cggggggcgc atggggggg aaccggaccg   2760 ccgtgggggg cgcgggagaa gcccctgggc ctccggagat gggggacacc ccacgccagt   2820
tcggaggcgc gaggccgcgc tcgggaggcg cgctccgggg gtgccgctct cggggcgggg   2880
gcaaccggcg gggtctttgt ctgagccggg ctcttgccaa tggggatcgc agggtgggcg   2940
cggcggagcc cccgccaggc ccggtggggg ctggggcgcc attgcgcgtg cgcgctggtc   3000 cttttgggcgc taactgcgtg cgcgctggga attggcgcta attgcgcgtg cgcgctggga   3060
ctcaaggcgc taactgcgcg tgcgttctgg ggcccggggt gccgcggcct gggctggggc   3120
gaaggcgggc tcggccggaa ggggtggggt cgcgcgcggct cccgggcgct gcgcgcact   3180 tcctgcccga gccgctggcc gcccgagggt gtggccgctg cgtgcgcgcg cgccgacccg   3240
gcgctgtttg aaccgggcgg aggcggggct ggcgcccggt tgggaggggg ttggggcctg   3300
gcttcctgcc gcgcgccgcg gggacgcctc cgaccagtgt ttgccttta tggtaataac   3360 gcggccggcc cggcttcctt tgtccccaat ctgggcgcgc gccggcgccc cctggcggcc   3420
taaggactcg gcgcgccgga agtggccagg gcggggcga cctcggctca cagcgcgccc   3480
ggctattctc gcagctcacc                                              3500
```

<210> SEQ ID NO 12
<211> LENGTH: 1639
<212> TYPE: DNA
<213> ORGANISM: Artificial Sequence
<220> FEATURE:
<223> OTHER INFORMATION: Description of Artificial Sequence: Synthetic
      luciferase gene

<400> SEQUENCE: 12

```
atggaagacg ccaaaaacat aaagaaaggc ccggcgccat tctatccgct ggaagatgga    60
accgctggag agcaactgca taaggctatg aagagatacg ccctggttcc tggaacaatg   120
cttttacaga tgcacatatc gaggtggaca tcacttacgc tgagtacttc gaaatgtccg   180
ttcggttggc agaagctatg aaacgatatg ggctgaatac aaatcacaga atcgtcgtat   240
```

```
gcagtgaaac tctcttcaat tctttatgcc ggtgttgggc gcgttattta tcggagttgc    300
agttgcgccc gcgaacgaca tttataatga acgtgaattg ctcaacagta tgggcatttc    360
gcagcctacc gtgtgttcgt ttccaaaaag gggttgcaaa aattttgaa cgtgcaaaaa     420 aagctcccaa tcatccaaaa aattattatc atggattcta aaacggatta ccagggattt    480
cagtcgatgt acacgttcgt acatctcatc tacctcccgg ttttaatgaa tacgattttg    540
tgccagagtc cttcgatagg gacaagacaa ttgcactgat catgaactcc tctggatcta    600
ctggtctgcc taaaggtgtc gctctgctca tagaactgcc tgcgtgagat tctcgcatgc    660
cagagatcct atttttggca atcaaatcat tccggatact gcgattttaa gtgttgttcc    720
attccatcac ggttttggaa tgtttactac actcgatatt tgatatgtgg atttcgagtc    780
gtcttaatgt atagatttga agagagctgt ttctgaggag ccttcaggat tacaagattc    840
aaagtgcgct gctggtgcca accctattct ccttcttcgc caaagcactc tgattgacaa    900
atacgattta tctaatttac acgaaattgc ttctggtggc gctcccctct ctaaggaagt    960
cggggaagcg gttgccaaga ggttccatct gccaggtatc aggcaaggta tgggctcact   1020
gagactacat cagctattct gattacaccc gaggggatg ataaaccggg cgcggtcggt    1080
aaagttgttc cattttttga agcgaaggtt gtggatctgg atacgggaaa acgctggcgt   1140
taatcaaaga ggcgaactgt gtgtgagagg tcctatgatt atgtccggtt atgtaaacaa   1200
tccggaagcg accaacgcct tgattgacaa ggatggatgg ctacattctg agacatagc    1260 ttctgggacg aagacgaaca cttcttcatc gttgaccgcc tgaagtctct gattaagtac   1320
aaaggctatc aggtggctcc cgctgaattg gaatccatct tgctccaaca ccccaacatc   1380
ttcgacgcag tgtcgcaggt cttcccgacg atgacgccgg tgaacttccc gccgccgttg   1440
ttgttttgga gcacggaaag acgatgacgg aaaaagagat cgtggattac gtcgccagtc   1500
aagtaacaac cgcgaaaagt tgcgcggagg agttgtgttt gtggacgaag taccgaaagg   1560
tcttaccgga aaactcgacg caagaaaaat cagagagatc ctcataaagg ccaagaaggg   1620
cggaaagatc gccgtgtaa                                                1639
```

<210> SEQ ID NO 13
<211> LENGTH: 270
<212> TYPE: DNA
<213> ORGANISM: Artificial Sequence
<220> FEATURE:
<223> OTHER INFORMATION: Description of Artificial Sequence: Synthetic
      pp90 polynucleotide

<400> SEQUENCE: 13

```
gaaattgctt ctggtggcgc tcccctctct aaggaagtcg gggaagcggt tgccaagagg     60
ttccatctgc caggtatcag gcaaggatat gggctcactg agactacatc agctattctg    120
attacacccg aggggatga taaaccgggc gcggtcggta agttgttcc attttttgaa     180 gcgaaggttg ggatctggat acgggaaaac gctggcgtt aatcaaagag gcgaactgtg    240
tgtgagaggt cctatgatta tgtccggtta                                     270
```

<210> SEQ ID NO 14
<211> LENGTH: 219
<212> TYPE: DNA
<213> ORGANISM: Artificial Sequence
<220> FEATURE:
<223> OTHER INFORMATION: Description of Artificial Sequence: Synthetic
      pp75 polynucleotide

<400> SEQUENCE: 14
gccaagaggt tccatctgcc aggtatcagg caaggatatg ggctcactga gactacatca        60
gctattctga ttacacccga gggggatgat aaaccgggcg cggtcggtaa agttgttcca       120 tttttgaag cgaaggttgg gatctggata cgggaaaacg ctgggcgtta atcaaagagg       180
cgaactgtgt gtgagaggtc ctatgattat gtccggtta                             219

<210> SEQ ID NO 15
<211> LENGTH: 159
<212> TYPE: DNA
<213> ORGANISM: Artificial Sequence
<220> FEATURE:
<223> OTHER INFORMATION: Description of Artificial Sequence: Synthetic
      pp54 polynucleotide

<400> SEQUENCE: 15
gctattctga ttacacccga gggggatgat aaaccgggcg cggtcggtaa agttgttcca        60 tttttgaag cgaaggttgg gatctggata cgggaaaacg ctgggcgtta atcaaagagg       120
cgaactgtgt gtgagaggtc ctatgattat gtccggtta                             159

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Synthetic
      pp23 oligonucleotide

<400> SEQUENCE: 16
gggaaaacgc tgggcgttaa tcaaagaggc gaactgtgtg tgagaggtcc tatgattatg        60
tccggtta                                                                68

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      pp9 oligonucleotide

<400> SEQUENCE: 17
gtgagaggtc ctatgattat gtccggtta                                          29

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      pp90-forward primer

<400> SEQUENCE: 18
aggcgctagc atggaaattg cttctggtgg cgctc                                   35

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      pp75-forward primer

<400> SEQUENCE: 19
aggcgctagc atggccaaga ggttccatct g                          31

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      pp54-forward primer

<400> SEQUENCE: 20
aggcgctagc atggctattc tgattacacc cgag                       34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      pp23-forward primer

<400> SEQUENCE: 21
aggcgctagc atggggaaaa cgctgggcgt taatc                      35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      pp9-forward primer

<400> SEQUENCE: 22
aggcgctagc atgtgagagg tcctatgatt atgtc                      35

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      luc stop-reverse primer

<400> SEQUENCE: 23
aggcactagt ttaaccggac ataatcatag gac                        33

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      alpha97 primer

<400> SEQUENCE: 24
attaggatcc accatggcca agttgaccag tgccg                      35

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      alpha100 primer

<400> SEQUENCE: 25
accggaattc tcagtcctgc tcctcggcca cg                         32

<210> SEQ ID NO 26
<211> LENGTH: 550
<212> TYPE: PRT
<213> ORGANISM: Artificial Sequence
<220> FEATURE:
<223> OTHER INFORMATION: Description of Artificial Sequence: Synthetic luciferase amino acid sequence

<400> SEQUENCE: 26

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe

```
                    355                 360                 365
Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ile Ala Val
545                 550

<210> SEQ ID NO 27
<211> LENGTH: 129
<212> TYPE: PRT
<213> ORGANISM: Artificial Sequence
<220> FEATURE:
<223> OTHER INFORMATION: Description of Artificial Sequence: Synthetic
      PPx amino acid sequence

<400> SEQUENCE: 27

Glu Leu Phe Leu Arg Ser Leu Gln Asp Tyr Lys Ile Gln Ser Ala Leu
1               5                   10                  15

Leu Val Pro Thr Leu Phe Ser Phe Ala Lys Ser Thr Leu Ile Asp
            20                  25                  30

Lys Tyr Asp Leu Ser Asn Leu His Glu Ile Ala Ser Gly Ala Pro
            35                  40                  45

Leu Ser Lys Glu Val Gly Glu Ala Val Ala Lys Arg Phe His Leu Pro
50                  55                  60

Gly Ile Arg Gln Gly Tyr Gly Leu Thr Glu Thr Thr Ser Ala Ile Leu
65                  70                  75                  80

Ile Thr Pro Glu Gly Asp Asp Lys Pro Gly Ala Val Gly Lys Val Val
                85                  90                  95

Pro Phe Phe Glu Ala Lys Val Val Asp Leu Asp Thr Gly Lys Thr Leu
                100                 105                 110

Gly Val Asn Gln Arg Gly Glu Leu Cys Val Arg Gly Pro Met Ile Met
            115                 120                 125

Ser

<210> SEQ ID NO 28
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      19 nt spacer between PPx and ATG of selectable marker

<400> SEQUENCE: 28
actagcatta ggatccacc                                                  19

<210> SEQ ID NO 29
<211> LENGTH: 7
<212> TYPE: RNA
<213> ORGANISM: Artificial Sequence
<220> FEATURE:
<223> OTHER INFORMATION: Description of Artificial Sequence: Synthetic
      Kozak sequence
<220> FEATURE:
<221> NAME/KEY: modified_base
<222> LOCATION: (2)..(3)
<223> OTHER INFORMATION: a, c, u or g
<220> FEATURE:
<221> NAME/KEY: modified_base
<222> LOCATION: (7)..(7)
<223> OTHER INFORMATION: a, c, u or g

<400> SEQUENCE: 29 annaugn                                                                7

<210> SEQ ID NO 30
<211> LENGTH: 7
<212> TYPE: RNA
<213> ORGANISM: Artificial Sequence
<220> FEATURE:
<223> OTHER INFORMATION: Description of Artificial Sequence: Synthetic
      Kozak sequence
<220> FEATURE:
<221> NAME/KEY: modified_base
<222> LOCATION: (2)..(3)
<223> OTHER INFORMATION: a, c, u or g

<400> SEQUENCE: 30 gnnaugg                                                                7

<210> SEQ ID NO 31
<211> LENGTH: 10
<212> TYPE: RNA
<213> ORGANISM: Artificial Sequence
<220> FEATURE:
<223> OTHER INFORMATION: Description of Artificial Sequence: Synthetic
      Kozak sequence

<400> SEQUENCE: 31 gccrccaugg                                                            10

<210> SEQ ID NO 32
<211> LENGTH: 377
<212> TYPE: DNA
<213> ORGANISM: Artificial Sequence
<220> FEATURE:
<223> OTHER INFORMATION: Description of Artificial Sequence: Synthetic
      spacer sequence

<400> SEQUENCE: 32
taaggatccc tcatcatcaa ctcctctcga tctactcgtc tccctcaagg tatcgctctc     60
cctcaaagaa ctccctccgt cagatcctcg catcccagag atcctatcta gatcctatat    120
catccaaaaa atcatcatca tcgatcctca aatcgatcac cagggatctc agtcgatcta    180
catcttcgtc acatctcatc tacctcccgg ttttcatcaa tatcatcttc taccagagtc    240
```

| | |
|---|---|
| cttcgaaagg gacaagacaa tcccactcat catcaactcc tctcgatcta ctcgtctccc | 300 |
| tcaaggtatc gctctccctc aaagaactcc ctccgtcaga tcctcgcatc ccagagatcc | 360 |
| tatctagatc caccatg | 377 |

<210> SEQ ID NO 33
<211> LENGTH: 411
<212> TYPE: DNA
<213> ORGANISM: Artificial Sequence
<220> FEATURE:
<223> OTHER INFORMATION: Description of Artificial Sequence: Synthetic
DNA polynucleotide encoding the pp8Zeo-EPP5
selection marker

<400> SEQUENCE: 33

| | |
|---|---|
| atgggtccta tgattatgtc cggttaagga tccaccatgg ccaagttgac cagtgccgtt | 60 |
| ccggtgctca ccgcgcgcga cgtcgcagga gcggtcgggt tctggaccga ccggctcggg | 120 |
| ttctcccggg acttcgtgga ggacgacttc gccggtgtgg tccgggacga cgtgaccctg | 180 |
| ttcatcagcg cggtccagga ccaggtggtg ccggacaaca ccctggcctg ggtgtgtgtg | 240 |
| cgcggcctgg acgagctgta caccgagtgg tcggaggtcg tgtccacgaa cttccgggac | 300 |
| gcctccgggc cggccatgac cgagatcggc gagcagccgt gggggcggga gttcgccctg | 360 |
| cgcgacccgg ccggcaactg cgtgcacttc gtggccgagg agcaggactg a | 411 |

<210> SEQ ID NO 34
<211> LENGTH: 1312
<212> TYPE: DNA
<213> ORGANISM: Artificial Sequence
<220> FEATURE:
<223> OTHER INFORMATION: Description of Artificial Sequence: Synthetic
DNA polynucleotide encoding the pp23CLase
selection marker

<400> SEQUENCE: 34

| | |
|---|---|
| atggggaaaa cgctgggcgt taatcaaaga ggcgaactgt gtgtgagagg tcctatgatt | 60 |
| atgtccggtt aaactagcat taggatccac catgggccag gaaaaagacg cctcctcaca | 120 |
| aggtttcctg ccacacttcc aacatttcgc cacgcaggcg atccatgtgg gccaggaccc | 180 |
| ggagcaatgg acctccaggg ctgtagtgcc ccccatctca ctgtccacca cgttcaagca | 240 |
| aggggcgcct ggccagcact cgggttttga atatagccgt tctggaaatc ccactaggaa | 300 |
| ttgccttgaa aaagcagtgg cagcactgga tggggctaag tactgtttgg cctttgcttc | 360 |
| aggtttagca gccactgtaa ctattaccca tcttttaaaa gcaggagacc aaattatttg | 420 |
| tatggatgat gtgtatggag gtacaaacag gtacttcagg caagtggcat ctgaatttgg | 480 |
| attaaagatt tcttttgttg attgttccaa aatcaaatta ctagaggcag caattacacc | 540 |
| agaaaccaag ctcgtttgga tcgaaacccc cacaaacccc acccagaagg tgattgacat | 600 |
| tgaaggctgt gcacatattg tccataagca tggagacatt attttggtcg tggataacac | 660 |
| ttttatgtca ccatatttcc agcgcccttt ggctctggga gctgatattt ctatgtattc | 720 |
| tgcaacaaaa tacatgaatg gccacagtga tgttgtaatg ggcctggtgt ctgttaattg | 780 |
| tgaaagcctt cataatagac ttcgtttctt gcaaaactct cttggagcag ttccatctcc | 840 |
| tattgattgt tacctctgca atcgaggtct gaagactcta catgtccgaa tggaaaagca | 900 |
| tttcaaaaac ggaatggcag ttgcccagtt cctggaatct aatccttggg tagaaaaggt | 960 |
| tatttatcct gggctgccct ctcatccaca gcatgagttg gtgaagcgtc agtgcacagg | 1020 |
| ttgcacaggg atggtcacct tttatattaa gggcactctt cagcacgctg agattttcct | 1080 |

-continued

| | |
|---|---|
| caagaaccta aagctattta ctctggccga gagcttggga ggattcgaga gccttgctga | 1140 |
| gcttccggca atcatgactc atgcatcagt tcttaagaat gacagagatg tccttggaat | 1200 |
| tagtgacaca ctgattcgac tttctgtggg cttagaggat gaggaagacc tactggaaga | 1260 |
| cctagatcag gctttgaagg cagcacaccc tccaagtggg attcacagct ag | 1312 |

<210> SEQ ID NO 35
<211> LENGTH: 6969
<212> TYPE: DNA
<213> ORGANISM: Homo sapiens

<400> SEQUENCE: 35

| | |
|---|---|
| ctatgtcatt tttgctaaca tgtaatgggc ttactattgt tattttaatt aaattgataa | 60 |
| atatatattt aaaatgttct tagtttaaat ttctaatata gtaaatattg atagatacaa | 120 |
| cctacataaa caaaagctat atggagtcct caataatttt taagaatgta aagggattct | 180 |
| gaggccaaaa tgtttgagaa ttgctgggct aggattgttc aagcctctct ggggcatatg | 240 |
| ctaattatct taaagccacc caatcatcac ccaccttccc accaatgtct tcgtactcac | 300 |
| ttcttgtgag ccaatcctca cagtcaggag gcagtagtgt taggatggtt gaaagtaaaa | 360 |
| gcacaaagag attgagttca aattctttct tggctacctg tgaagtttgt aactttgact | 420 |
| aatttactgg gcccttcaaa agtctcagtt ttctcatcta taaaggggt ataatggtag | 480 |
| tacctacctt atacgtttgt gagaattaag aaagaaggca cataatttat gttagctata | 540 |
| atagatgaaa ttcttagag ttttatttgt ggttatctaa tcataaggat tggaaagaag | 600 |
| taaagtccat gccaacttgt tttacttctt tgaaaaagag aaacaagagg tatagtaacg | 660 |
| tttaatgttt ggtttaacat gtacagtgga tgagagggca ttctatattg atctcctcaa | 720 |
| tctggccaga aaagtgttgt gatttctaac agtttatttt cacattttgt ttccctaagt | 780 |
| tcaatgagcc ctccacttct aatgaggtgg ctttagggta gagaaatcaa aaggcagttg | 840 |
| gctttgttgt gacgggcaga tctggatgga gcattataag ggtgaggctg ctgagtttcc | 900 |
| catcttgctt atacatatga tgctttgaaa cctacgctga cctgttttaa ctctggccta | 960 |
| aagacaggcc aggtgaacag aaatagagcc agcgtctcca ctggcaacac agccatcctg | 1020 |
| aagaggaatg tctgtgtgtg catctgccac cagaagtggg atgctagaga ggcattgatc | 1080 |
| tcttttttga tattgagttt tatccaagta ctcattaagt agatcccttt tattttcaaa | 1140 |
| atatctgggg ttaatgtgct taatttggtt agacctagtg agtgagctat ggagaactgg | 1200 |
| aatcatttta tatcagttcc tcatctttgc tcagattcat tctgtactgc ctgtctcttc | 1260 |
| tgcttcttag acaaagattg aacttgcagg ccaggtgcag tggctcatgc ctgtaattcc | 1320 |
| aacactttgg gaggccgagg cgggcagatc acttgaggtc gggaattcga accagcctg | 1380 |
| accaacatgg agaaaccccg cctctactaa aaatacaaag ttagctgggt gtggtggtgc | 1440 |
| atgcctgtaa tcccagctac tcaggaggct gaggcaggag aattgcttca acccaggaga | 1500 |
| cggagattgt ggtgagccga ggtgacgcca ttgcactcca gcctgggcaa caagagtgaa | 1560 |
| actccatctc aaaataaata aataaaaaga ttgaacttgc tacatgcttc tatctctatc | 1620 |
| tgccttctgt gctgccagct cctgcttcta gcaagaagca agagaactta tgttttttca | 1680 |
| acccctagtt ctctcctggt aaaactgtga agaatctatt tgcatatcta gccattctac | 1740 |
| atgcataaaa atgctatatc gacacaaaga aaagacttgt tcataggctc atagttctga | 1800 |
| tacaaggctt accagctgaa ttgcccacag tcaggcccta cagagaactc tgctagtttg | 1860 |

```
atactcctat taatatacag ctaataggtg gtcctgtatc ctacagctgt ggccaaggtc    1920
ccacacacaa tcaattttcc attccgttag actgggaggg agattgttag ctttctatga    1980
acataagaag atccctgat ggagccatct acataggata ggttttttgta taggtttaat    2040 gacccttcag agttggtaaa tggtccacaa tttctctaac cttcacttcc tggacccaaa    2100
gagagattgg caccaacttt actgtgtcat taatttcagg agtcattcac tgaccttctc    2160
cagcagtggc agcaactccc caagtcaatc aggcaataaa accagctgta ccaaaaatgt    2220
aacaacagtt caagtttact ttatccaggg gcctcaagta ttcaagattg acgtccctac    2280
ctccccatct ccaaggatgc ccccccctcc ccgccatgat gatacccaag agtgagtcag    2340
tgtagccagg taccattgcc cacaggaggc tcagctttgt cccttcaaa tgatcctccc      2400 caagggcttc tgtttctctt acttctagcc atttggtctt agccattgtg tttcctgtga    2460
tccatatgcc aagccccac atcttacata ggccattgga aatttgggtg ctctgggaaa    2520
cctcattaat caaccatgt cctgcaaggc tgactgccaa ccagcccaaa gactgacctg    2580
gtgtcacaga gatgtcctga aggccttctc ctcctggtga agcccatcat caagaagatg    2640
ttggacttgc agatccagac aagagaatat gaggatgttc ttaccacatc aggcagtaat    2700
acaatggcct cctaactggt gtccttgtgc ccgtgctttt cctcttctcc attccccata    2760
cagcagtcag gaaatctgat tgtgttcttc ctttgtttaa aaccctttcc tgtgtcccac    2820
atgatggcct gcatgatcct tcatgccctt gaccttgcca acctctcagg tctcatctca    2880
tgccaccttc ttcctcccctg ctgtgctcag gccacatggc cttcctctag ctcctcaagt    2940
gcctagaggc ccttccagag gctggtccct ttgactcttc aactcattaa tttccactca    3000
tccttcagag ctcagctcaa atgtcacttc ctcgaggcga ctgtccttga gtccccactc    3060
gctcatcata cttttgctag ctctgcgtcc cgttccatca taggttgtaa ttacaagtct    3120
gagtaatgtg tgcctccttt agtggcttgt aaggttcatg aaggcaggat ctatatctat    3180
caaagttccc cctgaattct gagtacctac acagtaggag tctgataaat atttattgga    3240
caaataaatc aacaaaaata aatatggaaa agttgctatt gtgggcttca ccagttggtg    3300
agtacagatg tagtcctata acttcataca ctttcaattg ctctatcaca tttgtgatag    3360
ctatgaagtt tttccttcta tgcaacatgc tgctattaga cagctacagg aatgagtgaa    3420
tagcttctcc tctagtttct tgtcctcaat ctctctcttt cctcccctct ggcccaccct    3480
aaatacttat acaggcgagt gtggacacac acacacacac acatcctgtg aagaggaatg    3540
agagcacaaa aagttatata caattcattg taatatgaat caggaaaaag cttcctgact    3600
tcagcctaaa gattccctgg gctgagggga aagggaatgt ccagatggca aatggagtga    3660
ggagagaact tatcctggtg ggtcactgaa aagagtgcta agcctgctcc agtggggaag    3720
aggaagatga cagaaatgtc aggtaagttt gtgggaactg aaaggggagg caatctagaa    3780
gtgttctcag gcaaaggccc aaggagaccc aagatctcag agactaaggt gctatgtggc    3840
agatatgagt ctgggacagc ttacagagtc ccatacgtca cagtgtggcc tggaagcaga    3900
tggatggttc tggggcctga gagtgccgca ggagtccatg ggtcttgggt cacagcctgc    3960
agtttccatg actcagcctg gcagtggaat gacttcctgg gcaccccaaa ggctttatag    4020
aagttgaaag gatagttgtc aaacgtgcag gagcctttta aatgggatca tagggacaag    4080
gtagcaatca tctgcatgtc aggaaacgaa cactaaacag gatgatggat ggcccagtga    4140
aggcccaggt gatagcagtc tagaaccagg taccccatct ccccacatgt tgacatgcca    4200
caagcacccc agaaattagt tatttccctg cagttacata ttgactaatt ttaaattgtt    4260
```

```
actgcttaca ggatggaggc tctaaataga aaaaaagtta gagagaaaca taaatttgtt      4320 atgttttat acagctgggt ttgtgggctg caaattgaaa ccattataca attctctttt       4380
aaaatgcaaa tatccctcat acgcatatca tgtggacaaa gtgtttgttt tattaatagc     4440
atcccctaac ctagtttcac tattaaaagg taggtctgag tgggatgtgg gtccctagtg      4500
acctagtgtg agaatagagg gtgttttgtt ttgttttgtt tttgagactg agtctcgctc     4560
tgttgcccag gctggagtgc agtggcatga tctcggctca ctgcaacctc tgcctcctgg     4620
gttcaagtga ttctcatgcc tcagcctctt gagtagctgg gattagatgt gcccaacacc    4680
acgcctgact aattttgta tttttagtag ggatgggtt tcaccatgtt ggccaggctg       4740
gtctcaaact cctgacctca gtaatccac ccactttggt ctcccaaagt gctgggatta     4800
caggcgtgag ccaccacgtc cggccttaga gggcatttta agggaagaag agaggagttg    4860
ggaaaggatc ttctttctaa tgggaagaga agaagagac aatagaaaaa ggaagaagga      4920
aaagggccca tgaatgtcc aatattcctt ttgttttcat tgtgattctc atacagaatt      4980
cataaatact tcaacctaaa ccattgaaat tggaatttaa tctgaggtat gaaaaaaatg    5040
ctaggtttaa aatcacaacc caggttgaat ttcttactt gcccattaat agatgtgtga      5100
ccttgagcat tctcttaact tctctgagcc tcagttactt cagttgtaaa aagggtctaa    5160
taaaacacat cccactgaat tactgagagg attgatccaa ttacatgaaa gagctctgaa     5220
acaataaaaa gttgcaccat ctggggtatc agtttgcggt cgaggagaca atggggagaa   5280
ataatgtaag tgttgagcac atctgcggtc tttaaacaga gagctcaaca caaggacatg   5340
ggcatattgg aaaaaactat ttcagaagag gggaaaaggg agaaaggggg atatgtgggt   5400
attagaggca aacccagata tcctgccttg aggtcaaata attataacat taaatcctgt   5460
ttactgatgc ttagctgtca ggctcttgct catttacctt ggagatccat ttagaattag    5520
tgtaaggtgt aattgacctg tacttagagt tccagaatag acaatcact tccaaatgcc     5580 ctcagtataa gaaattaaca gtacttgggg ctttagaaat caatgttcaa cctttcaact    5640
actagaaagc ctttttagtt attgtgctta ctatgaaagc ccttggctgt cagttcaaca   5700
agtcgttctt gctttgtgac atctctggaa gtttaatagt tctgtgagaa agtccttgtc    5760
agtgttctga aaactgggaa ttaggaagtc gacttccaat caagcttcag atgacatgcg   5820
acatgcgtta agtttagaaa taacgttagt gttttctaatt tagcatcgtg ttggagtcct   5880
aattatgaaa tgacattaag aaaattccat tcctcagaat tcttgtgcag tagcattggg    5940
tagaaacacc attgtgttct gtgacctggg gtagggatga tatctcaaaa acgcatgctc    6000
aggttgccca tggtgatagc taaactgtct tctcaggaga ggagcaggct ttattaactg    6060
gaactcacca gatttcacag aacatttga agggcttagg attgtgagtt tggaggtaga   6120
tgccaagcag aggtaaacat tttgtataac agaagaaaca tatttgatat gggagagaga   6180
cagaaatctt gtgaaaact ccagagccat caaagctggg acagtgttaa agacgagcac    6240
cctggaagtg aggagccaag tgtgggtttt gaggaacaga tatattaagg gggattctca    6300
caaatgtttt attttgacaa atatcaataa tttagaaaag ttgcaagaat agtatagcaa   6360
ttattcatat accccttcca tatagtacac agaaaaagag ggtatatatt ttaataaata    6420
tttgtgtata cacattttgt gtatagatag gcagataaat agataaagag acaaatgtgc    6480
acctgtgtat aattttctga actgtttgag aattggttgt aagcatcacg acacttcacc    6540
accaaatact tcagcatgtg tctcctaaga acaaggctgt tctctacatg accacaacat    6600
```

| | |
|---|---:|
| agttatttca cccagaaact taaacttgat acaatacaat atctaatatt cagtccatat | 6660 |
| tcaaatttct cctatcatcc aaataatatc attactaatc tccaatataa agagatttaa | 6720 |
| aacatgtttt ccatgttcaa cataaatgtc ttctccattt ttcttacaaa atcatcaaaa | 6780 |
| acaactacgt ttcccattta tacttttaca ccagtagttt ctttggagga acttgcactt | 6840 |
| gtcccacatc cagattggca ggggataaaa tagaaataat aagagctggc agaagagagg | 6900 |
| ctggttgatg ctgattacat tcaaaataac tatttggagg aaaaagcact gattctgttc | 6960 |
| ctggggtgt | 6969 |

<210> SEQ ID NO 36
<211> LENGTH: 3498
<212> TYPE: DNA
<213> ORGANISM: Homo sapiens

<400> SEQUENCE: 36

| | |
|---|---:|
| gcccacccta aatacttata caggcgagtg tggacacaca cacacacaca catcctgtga | 60 |
| agaggaatga gagcacaaaa agttatatac aattcattgt aatatgaatc aggaaaaagc | 120 |
| ttcctgactt cagcctaaag attccctggg ctgagggaa agggaatgtc cagatggcaa | 180 |
| atggagtgag gagagaactt atcctggtgg gtcactgaaa agagtgctaa gcctgctcca | 240 |
| gtggggaaga ggaagatgac agaaatgtca ggtaagtttg tgggaactga aggggaggc | 300 |
| aatctagaag tgttctcagg caaaggccca aggagaccca agatctcaga gactaaggtg | 360 |
| ctatgtggca gatatgagtc tgggacagct tacagagtcc catacgtcac agtgtggcct | 420 |
| ggaagcagat ggatggttct ggggcctgag agtgccgcag gagtccatgg gtcttgggtc | 480 |
| acagcctgca gtttccatga ctcagcctgg cagtggaatg acttcctggg cacccaaag | 540 |
| gctttataga agttgaaagg atagttgtca aacgtgcagg agccttttaa atgggatcat | 600 |
| agggacaagg tagcaatcat ctgcatgtca ggaaacgaac actaaacagg atgatggatg | 660 |
| gcccagtgaa ggcccaggtg atagcagtct agaaccaggt accccatctc cccacatgtt | 720 |
| gacatgccac aagcacccca gaaattagtt atttccctgc agttacatat tgactaattt | 780 |
| taaattgtta ctgcttacag gatggaggct ctaaatagaa aaaagttag agagaaacat | 840 |
| aaatttgtta tgtttttata cagctgggtt tgtgggctgc aaattgaaac cattatacaa | 900 |
| ttctcttta aaatgcaaat atccctcata cgcatatcat gtggacaaag tgtttgtttt | 960 |
| attaatagca tcccctaacc tagtttcact attaaaggt aggtctgagt gggatgtggg | 1020 |
| tccctagtga cctagtgtga aatagaggg tgttttgttt tgttttgttt ttgagactga | 1080 |
| gtctcgctct gttgcccagg ctggagtgca gtggcatgat ctcggctcac tgcaacctct | 1140 |
| gcctcctggg ttcaagtgat tctcatgcct cagcctcttg agtagctggg attagatgtg | 1200 |
| cccaacacca cgcctgacta attttgtat ttttagtagg gatggggttt caccatgttg | 1260 |
| gccaggctgg tctcaaactc ctgacctcaa gtaatccacc cactttggtc tcccaaagtg | 1320 |
| ctgggattac aggcgtgagc caccacgtcc ggccttagag gcatttaa gggaagaaga | 1380 |
| gaggagttgg gaaaggatct tctttctaat gggaagagaa agaagagaca atagaaaag | 1440 |
| gaagaaggaa aagggcccaa tgaatgtcca atattccttt tgttttcatt gtgattctca | 1500 |
| tacagaattc ataaatactt caacctaaac cattgaaatt ggaatttaat ctgaggtatg | 1560 |
| aaaaaaatgc taggttaaa atcacaaccc aggttgaatt tcttactttg cccattaata | 1620 |
| gatgtgtgac cttgagcatt ctcttaactt ctctgagcct cagttacttc agttgtaaaa | 1680 |
| agggtctaat aaaacacatc ccactgaatt actgagagga ttgatccaat tacatgaaag | 1740 |

```
agctctgaaa caataaaaag ttgcaccatc tggggtatca gtttgcggtc gaggagacaa    1800
tggggagaaa taatgtaagt gttgagcaca tctgcggtct ttaaacagag agctcaacac    1860
aaggacatgg gcatattgga aaaaactatt tcagaagagg ggaaaaggga gaaaggggga    1920
tatgtgggta ttagaggcaa acccagatat cctgccttga ggtcaaataa ttataacatt    1980
aaatcctgtt tactgatgct tagctgtcag gctcttgctc atttaccttg gagatccatt    2040
tagaattagt gtaaggtgta attgacctgt acttagagtt ccagaatagg acaatcactt    2100
ccaaatgccc tcagtataag aaattaacag tacttggggc tttagaaatc aatgttcaac    2160 cttcaacta ctagaaagcc ttttagtta ttgtgcttac tatgaaagcc cttggctgtc    2220
agttcaacaa gtcgttcttg ctttgtgaca tctctggaag tttaatagtt ctgtgagaaa    2280
gtccttgtca gtgttctgaa aactgggaat taggaagtcg acttccaatc aagcttcaga    2340
tgacatgcga catgcgttaa gtttagaaat aacgttagtg tttctaattt agcatcgtgt    2400
tggagtccta attatgaaat gacattaaga aaattccatt cctcagaatt cttgtgcagt    2460
agcattgggt agaaacacca ttgtgttctg tgacctgggg tagggatgat atctcaaaaa    2520
cgcatgctca ggttgcccat ggtgatagct aaactgtctt ctcaggagag gagcaggctt    2580
tattaactgg aactcaccag atttcacaga acattttgaa gggcttagga ttgtgagttt    2640
ggaggtagat gccaagcaga ggtaaacatt ttgtataaca gaagaaacat atttgatatg    2700
ggagagagac agaaatcttg tggaaaactc cagagccatc aaagctggga cagtgttaaa    2760
gacgagcacc ctggaagtga ggagccaagt gtgggttttg aggaacagat atattaaggg    2820
ggattctcac aaatgtttta ttttgacaaa tatcaataat ttagaaaagt tgcaagaata    2880
gtatagcaat tattcatata ccccttccat atagtacaca gaaaaagagg gtatatattt    2940
taataaatat ttgtgtatac acattttgtg tatagatagg cagataaata gataaagaga    3000
caaatgtgca cctgtgtata atttttctgaa ctgtttgaga attggttgta agcatcacga    3060
cacttcacca ccaaatactt cagcatgtgt ctcctaagaa caaggctgtt ctctacatga    3120
ccacaacata gttatttcac ccagaaactt aaacttgata caatacaata tctaatattc    3180
agtccatatt caaatttctc ctatcatcca aataatatca ttactaatct ccaatataaa    3240
gagatttaaa acatgttttc catgttcaac ataaatgtct tctccatttt tcttacaaaa    3300
tcatcaaaaa caactacgtt tcccatttat acttttacac cagtagtttc tttggaggaa    3360
cttgcacttg tcccacatcc agattggcag gggataaaat agaaataata agagctggca    3420
gaagagaggc tggttgatgc tgattacatt caaaataact atttggagga aaaagcactg    3480
attctgttcc tggggtgt                                                  3498
```

<210> SEQ ID NO 37
<211> LENGTH: 3352
<212> TYPE: DNA
<213> ORGANISM: Homo sapiens

<400> SEQUENCE: 37

```
ttagtctaaa ttagggatac acactcctcc ctgagctcta gaccctctc tctaactttc      60 actgatatc tccaccttga tagttcacca tgtctcaagt tcagttttgc tgaacctgaa     120
ctcataatct tcaccttaaa ctgcatcctc atccagcatt ccctaccttg gtgaccatga     180
tcaccaacct ctctcattgt aaaaacctgc ctaacacctt cccttccctc atcttccatc     240
tccagttcat tgctaagtgc tgatgttatt cttaaatat gtcttaaagc aatctacttc     300
```

```
tctccatctt ggctcaggca ctttagtcca agctaccata acctatcctc tgaactactg    360
gcccacagaa tccactcttg cctctcccct aaaccattct ccaaaatgca ttccaagtat    420
tttttaaatt taactgaaaa tctgatcaca tcatgtgtct ttataaacac atcaatggct    480
tatccttaag ataaagacaa aagtcctaac atggcctata cagctctaca acattttttcc   540
atgcttattt ctcagctagc tacaatgttt tcctccatcc ctatgctcca gtcacaattc    600
cttcaatatg tccttgcttt gtcccacctc agagcttgcc acatgcagtt tcttctgact    660
cacatcccct tccttggaat gactgcctct cttttgatta gttaattttc tataatactg    720
cagacctcaa ctcaaatatc tcttgattcc ctcaaccacc agaccagatc agctctctca    780
ctatgcactt accatgtttt gaaattaata ctctctgaat tgtttatcac ctgtacctag    840
aatatagtgt atgatattta ttggggggggc tcaatatttt gagtggatga gtaaatatat    900
tacagatagc taattattca agatttcatg ttcacattat tgctaaaaat gtagatgaag    960
taaaagtaga ttgaaatagg aggatataaa catgttggcg ctctttacat cacatacatg   1020
gattatgttt ttctttgttt gtttttagat gaagtcttgc gctgtcaccc aggctggacg   1080
gcagtggccc gagtgcacag gcaacctctg cctcccaggt tcaagcgatt ctcctccctc   1140
agcctcccga gtagctggga ttacaggagc ccaccaccaa gcccagctaa ttttgtatt    1200
tttagtagag acggggtttc gccatgttgg ccaggctggt ctgaactgct gacctcaggt   1260
gatccacccg cctcggcctc ccaaagtgct gggattacag gcgtgagcca ccatgcgcgg   1320
cccatggcat atgttatcag taatatgtaa gtatggcttc agtcaaagca aggaagttga   1380
aagtaacaat taaaaaaaaa aaagtcatca ggatccaaag ctgtggagaa aactcaacct   1440
ctgcctcctg ggttcaagca attctcctgc ctcagcctcc ctggtagctg ggattacagg   1500
tgcctgacac caccccagc taattttgt attttagta gagacatggt ttcaccatgt    1560
tggtcaggct ggtcttgaac tcctgacctc aggtgatcca cccacctcag cctcccaaag   1620
tgctgggatt acaggcgtga gccacttttta gaaaatgttt tcatctatct caatacctca   1680
ctacccctcc tgatattcca tctataatag caacagttgt gaaatgcact agattctaac   1740
attaacacta gatccattaa gaacagagca gaagagagtc tggatacaca aatttcacaa   1800
ttattggctc ccatcaacat atctaactca agcataaagt tgtttcagca gtagtttaag   1860
gttggttact aatgcaacac ctctttgcat gcaatggccc attaaattat cttcaacttt   1920
aaaaggttcc tttgttttta atgcttata atgaacaaat ataccaat accttggcag    1980
aattcattaa cttaataact tcaatatgtt gttcatataa aaatttctgg taaatgagaa   2040
ctgtacatta ctgatgtgac aaggtacaca agccaatgtt gacataatgt tttcaaaatg   2100
gggtgtctgc tgtaactgaa ctaaatataa taactttatt caagaatgag tttcaatgat   2160
aggacaaaac ttgataaaat gaataaataa ataattatat gccagagttc agtaaaccct   2220
gtgtgtacac ctgaaaaagc tcaaacttgc ctagcacata tagagtccga attcagttgg   2280
gtttgtgtga acgggtagg ttgagcccta aaaagaggt agataaccca tataggcaga    2340
cttccttatt ttatttattt ttttctgctt cagcctcctg agtagctggg actacaggtg   2400
tgtgccacca cgtctggcta attttgtttg tttttagtag agatgggtt tcaccatatt    2460
ggccaggctg gtctcgaact cctgaccttg tgatctgcgc gcctcggcct cccaaagtgc   2520
tgggattaca ggcgtgagcc actgcgcctc gccaacttcc ttattttaaa tgccatttcc   2580
cactaaaaat aaaaccagta attctttgaa aaaaagttaa tattatgtat aggactggaa   2640
gtatataaga taaaactgga atatattgtc ataccagaaa tcaaagattt tgtcaaagac   2700
```

```
taatagttcc atgtcaaaaa gattcactaa tcaatttgca gaggctccca ctggccaaag    2760
atagagcttg atcatcaaca ggaataataa ctataatggg ttaaaacata gcaattatgt    2820
ttaaatctat aggtttatag taataatgtt aaaatcatta gtcacctttg aaagatgcta    2880
cgactcttta atccatcttg aattaatttt tgtataaggt gtaaggaagg gatccagttt    2940
cagctttcta catatggcta gccagttttc ccagcaccat ttattcaata gggaatcctt    3000
tccccattgc ttgttttttct caggtttgtc aaagatcaga tagttgtaga tatgcggtgt    3060
tatttctgag ggctctgttc tgttccattg atctatatct ctgttttggt accagtacca    3120
tgctgttttg gttactgtag ccttgtagta tagtttgaag tcaggttgca tgatgcctcc    3180
agctttgttc ttttggctta ggattgactt ggcaatgcgg gctccttttt ggttccatat    3240
gaactttaaa gtagttttttt ccaattctgt gaagaaagtc attggcagct tgatggggat    3300
gacattgaat ctataaatta ccttgggcag tatggccatt ttcacgatat tg            3352
```

<210> SEQ ID NO 38
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ala Lys Leu Thr Ser Ala Val Cys Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 39
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ala Lys Leu Thr Ser Ala Val Gln Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala

```
Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Met Thr Glu
                 85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 40
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ala Lys Leu Thr Ser Ala Val Thr Val Leu Thr Ala Arg Asp Val
  1               5                  10                  15

Ala Gly Ala Val Glu Phe Trp Thr Asp Arg Leu Gly Phe Ser Arg Asp
             20                  25                  30

Phe Val Glu Asp Asp Phe Ala Gly Val Val Arg Asp Asp Val Thr Leu
         35                  40                  45

Phe Ile Ser Ala Val Gln Asp Gln Val Val Pro Asp Asn Thr Leu Ala
     50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Met Thr Glu
                 85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 41
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ala Lys Leu Thr Ser Ala Val Pro Val Leu Thr Ala Arg Asp Val
  1               5                  10                  15

Ala Gly Ala Val Glu Phe Trp Thr Asp Arg Leu Gly Phe Ser Arg Asp
             20                  25                  30

Phe Val Glu Asp Asp Phe Ala Gly Val Val Arg Asp Asp Val Thr Leu
         35                  40                  45

Phe Ile Ser Ala Val Gln Asp Gln Val Val Pro Asp Asn Thr Leu Ala
     50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Val Thr Glu
                 85                  90                  95

Ile Gly Glu Gln Pro Trp Gly Arg Glu Phe Ala Leu Arg Asp Pro Ala
            100                 105                 110
```

Gly Asn Cys Val His Phe Val Ala Glu Glu Gln Asp
            115                 120

<210> SEQ ID NO 42
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ala Lys Leu Thr Ser Ala Val Pro Ala Leu Ala Ala Arg Asp Val
1               5                   10                  15

Ala Gly Ala Val Glu Phe Trp Thr Asp Arg Leu Gly Phe Ser Arg Asp
            20                  25                  30

Phe Val Gly Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120

<210> SEQ ID NO 43
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Ala Lys Leu Thr Ser Ala Val Pro Val Leu Thr Ala Arg Asp Val
1               5                   10                  15

Ala Gly Ala Val Glu Phe Trp Thr Asp Arg Leu Arg Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Gly Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120

<210> SEQ ID NO 44
<211> LENGTH: 124
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 44

Met Ala Lys Leu Thr Ser Ala Val Pro Val Leu Thr Ala Pro Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Lys Leu Tyr Ala Glu Trp Ser Glu
65                  70                  75                  80

Val Val Ser Thr Asn Phe Arg Gly Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 45
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Lys Leu Thr Ser Ala Val Pro Val Leu Thr Ala Arg Asp Val
1               5                   10                  15

Ala Gly Ala Val Glu Tyr Trp Thr Gly Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 46
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Ala Lys Leu Thr Ser Ala Val Pro Val Leu Thr Ala Arg Asp Val
1               5                   10                  15
```

-continued

Ala Gly Ala Val Glu Phe Trp Thr Asp Arg Leu Gly Phe Ser Arg Asp
            20                  25                  30

Leu Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 47
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Lys Leu Thr Ser Ala Val Pro Val Leu Thr Ala Arg Asp Val
1               5                   10                  15

Ala Gly Ala Val Gly Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Thr Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 48
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

```
Trp Val Trp Val Arg Gly Leu Asp Glu Leu Tyr Ala Glu Trp Ser Glu
65                  70                  75                  80

Val Glu Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115             120
```

STRINGENT SELECTABLE MARKERS

CROSS-REFERENCE TO RELATED APPLICATIONS

This application is a Continuation of U.S. patent application Ser. No. 13/378,006 filed Mar. 6, 2012, which is the U.S. National Stage of International Patent Application No. PCT/NL2010/050367, filed Jun. 15, 2010 which claims the benefit of U.S. Provisional Patent Application No. 61/187,022, filed Jun. 15, 2009, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 4, 2016, is named Sequence.txt and is 64.6 KB in size.

FIELD OF THE INVENTION

The present invention relates to the field of molecular biology and biotechnology. More specifically the present invention relates to means and methods for improving the selection of host cells with high expression levels.

BACKGROUND OF THE INVENTION

Bioactive proteins are produced in various host cells, ranging from bacteria and yeast to mammalian cells. Mammalian cells as host cell are preferred when the protein requires certain posttranslational modifications, such as glycosylation to function properly. In general, proteins produced in mammalian cells are expressed from a so-called 'transgene' encoding the protein of interest. To ensure that the right, protein-producing cell is selected, the transgene coding for the gene of interest is coupled to a second transgene encoding a selectable marker that most often is placed on the same vector. When a selection agent is added to the cell culture that has been transfected with the plasmid harboring the transgene, only those cells will survive that also harbor the selectable marker. A common problem is that the stringency of selection is often low. That implies that the cell has to make only very small amounts of selection protein in order to survive the toxic selection agent. In particular when the selection marker is an enzyme that neutralizes the toxic selection agent, these problems occur. One enzyme molecule can neutralize many molecules of selection agent in the course of time. Neomycin and the aminoglycoside phosphotransferase (neomycin) selection marker are an example of such combination. The limited requirement of selection marker protein has also implications for the expression levels of the transgenic protein. Low expression levels of selection marker can, for instance, be achieved by incorporation of only few copies of the plasmid. This, however, implies that also only few gene copies are available for the expression of the transgene protein, with low transgenic protein expression levels as result. Therefore, low expression levels of the protein of interest commonly accompany low selection stringency. This is obviously an unwanted side effect of low selection stringency.

An improvement in selection stringency can be seen when Zeocin and the Zeocin selection marker are used. The Zeocin selection protein is a selection marker protein that does not act as an enzyme. It stoichiometrically binds two Zeocin selection molecules and does not further process these molecules. Thus the available Zeocin selection proteins have only a limited capacity to neutralize a certain number of Zeocin molecules added to the culture medium. Therefore, the cell must produce much more Zeocin than for instance the Neomycin selection marker mRNA to produce enough selection protein to respectively neutralize Zeocin or Neomycin. When coupled to a gene of interest, this commonly also results in higher mRNA levels that encode the gene product of interest. These higher mRNA levels in turn signify higher expression levels of the gene product of interest.

Stably transfected clones can only be selected for the expression levels of the selection marker and not for the expression level of the gene of interest. Because of this, it is preferable that the expression of the gene of interest is directly linked to the expression level of the selection marker. There are multiple ways to physically couple the gene of interest to the gene encoding the selection marker gene. An IRES (Internal Ribosome Entry Site) sequence can be placed between the gene of interest and the gene encoding the selection marker. This creates a bicistronic mRNA from which both the gene product of interest and the selection protein are translated (Rees et al., 1996, Biotechniques 20: 102-110). When a high amount of selection protein, such as Zeocin selection protein is needed for the cell to survive, high levels of this bicistronic mRNA are needed. This in turn implies that high levels of mRNA encoding the gene product of interest are available for translation, and that relatively high expression levels of the gene product of interest are achieved. This principle provides higher selection stringency than when the gene of interest and the gene encoding the selection marker are not coupled through an IRES sequence. This procedure to select cell clones that express relatively high levels of the gene product of interest is an accepted and often employed method (see e.g. WO 03/106684, WO 2006/005718 and WO 2007/096399).

Other means to reach a higher level of selection stringency is to use selectable markers that harbor mutations that attenuate but do not completely destroy the activity of the selection marker. In order to neutralize a similar number of toxic selection molecules in the culture medium more mutated, more impaired selection protein has to be produced than the wild type selection protein. When coupled to the gene of interest through an IRES sequence, the higher impaired selection marker mRNA levels warrant that there is also more mRNA of the gene of interest available for translation. (see e.g. WO 01/32901 and WO 2006/048459)

In yet another example of high selection stringency systems the translation of the selection marker protein is severely impaired. In this example the modified selection marker gene is placed upstream of the gene of interest, not separated by an IRES sequence. In essence, the optimal ATG translation initiation codon of the selection marker is replaced by a less favorable translation initiation codon, such as GTG or TTG. In either case the translation machinery will not initiate translation on the GTG or even less so on the TTG, but will proceed scanning the mRNA. Provided there are no ATGs present in the selection gene (these have to be removed), the first ATG that will be encountered is the ATG of the gene of interest. In this configuration, high levels of this mRNA have to be produced to obtain enough selection protein, which in turn is needed for the cell to survive. However, these high mRNA levels also warrant that concomitantly high levels of the coupled gene of interest will be translated. Through this principle a system of high selection stringency has been created that results in a) only few colonies that survive the selection procedure and b) these colonies display relatively high expression levels of the gene product of interest. In particular a configuration that couples a TTG Zeocin selection marker to the gene of interest provides extremely high selection pressure. Collectively, these selection systems have been termed STAR-Select (WO 2006/048459 and WO 2007/096399).

The present invention discloses further improved means and methods for high stringency selection of mammalian cells to achieve high expression levels of gene products of interest.

DESCRIPTION OF THE INVENTION

Definitions

A "nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell. Common types of vectors may be derived from naturally occurring plasmids, phages and viruses. Vectors usually comprise further genetic elements to facilitate their use in molecular cloning, such as e.g. selectable markers, multiple cloning sites and replication origins functional in one or more host cells and the like.

One type of nucleic acid construct is an "expression cassette" or "expression vector". These terms refers to nucleotide sequences that are capable of effecting expression of a gene in host cells or host organisms compatible with such sequences. Expression cassettes or expression vectors typically include at least suitable transcription regulatory sequences and optionally, 3' transcription termination signals. Additional factors necessary or helpful in effecting expression may also be present, such as expression enhancer elements.

The term "monocistronic gene" is defined as a gene capable of providing a RNA molecule that encodes one gene product. A "multicistronic transcription unit", also referred to as multicistronic gene, is defined as a gene capable of providing an RNA molecule that encodes at least two gene products. The term "bicistronic gene", also referred to as "dicistronic gene", is defined as a gene capable of providing a RNA molecule that encodes two gene products. A bicistronic gene is therefore encompassed within the definition of a multicistronic gene.

The term peptide herein refers to any molecule comprising a chain of amino acids that are linked in peptide bonds. The term peptide thus includes oligopeptides, polypeptides and proteins, including multimeric proteins, without reference to a specific mode of action, size, 3-dimensional structure or origin. A "polypeptide" as used herein usually comprises at least five amino acids linked by peptide bonds. The terms "protein" or "polypeptide" are used interchangeably. A "fragment" or "portion" of a protein may thus still be referred to as a "protein". An "isolated protein" is used to refer to a protein which is no longer in its natural environment, for example in vitro or in a recombinant (fungal or plant) host cell. The term peptide also includes post-expression modifications of peptides, e.g. glycosylations, acetylations, phosphorylations, and the like.

A "gene" or a "transcription unit" as used in the present invention can comprise chromosomal DNA, cDNA, artificial DNA, combinations thereof, and the like. Transcription units comprising several cistrons are transcribed as a single mRNA.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in eukaryotic (host) cells.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

As used herein, an "internal ribosome entry site" or "IRES" refers to an element that promotes direct internal ribosome entry to the translation initiation codon (also known as start codon) of a cistron (a protein encoding region), thereby leading to the cap-independent translation of the gene. See, e.g., Jackson R J, Howe 11 M T, Kaminski A (1990) Trends Biochem Sci 15 (12): 477-83) and Jackson R J and Kaminski, A. (1995) RNA 1 (10): 985-1000. The present invention encompasses the use of any cap-independent translation initiation sequence, in particular any IRES element that is able to promote direct internal ribosome entry to the initiation codon of a cistron. "Under translational control of an IRES" as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron.

As used herein, "cistron" refers to a segment of a polynucleotide sequence (DNA) that contains all the information for production of single polypeptide chain.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Nucleotide sequences encoding a selectable marker of the invention may also be defined by their capability to hybridize with the nucleotide sequences of SEQ ID NO.'s 1-9, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

The adaptiveness of a nucleotide sequence encoding protein of interest to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51).

DETAILED DESCRIPTION OF THE INVENTION

A nucleic acid construct according to the invention can be used to select eukaryotic cells, preferably mammalian cells, that have high expression levels of a gene product of interest, by selecting for the expression of the selectable marker. Subsequently or simultaneously, one or more of the selected cell(s) can be identified, and further used for expression of high levels of the gene product of interest.

The present invention is based on an impaired efficiency of expression of a selectable marker. Expression of a selectable marker can be detected using routine methods known to the person skilled in the art, e.g. by determining the number of surviving colonies after a normal selection period. As is well known to the person skilled in the art there are a number of parameters that indicate the expression level of a selection marker polypeptide such as, the maximum concentration of selection agent to which cells are still resistant, number of surviving colonies at a given concentration, growth speed (doubling time) of the cells in the presence of selection agent, combinations of the above, and the like. By using the present invention, cells can be identified that have high levels of expression, in particular high levels of transcription of the selectable marker.

In a first aspect, the present invention relates to a nucleic acid construct comprising a multicistronic transcription unit, comprising a) a nucleotide sequence encoding a selectable marker functional in a eukaryotic host cell; and, b) a functional open reading frame. Preferably, the stop codon of the functional open reading frame is present between 0 and 250 nucleotides upstream of the separate translation initiation codon of the nucleotide sequence encoding the selectable marker. Preferably, the sequence separating the stop codon of functional open reading frame and the separate translation initiation codon of the nucleotide sequence encoding the selectable marker is devoid of translation initiation codons.

A multicistronic transcription unit according to the invention has the nucleotide sequence coding for the selectable marker downstream of the functional open reading frame. A multicistronic transcription unit according to the invention preferably is a bicistronic transcription unit comprising in a 5' to 3' direction 1) a functional open reading frame and 2) a sequence coding for selectable marker. Hence, the functional open reading frame is present upstream of the sequence coding for the selectable marker. A functional open reading frame is herein understood as a nucleotide sequence comprising in a 5' to 3' direction 1) a translation initiation codon, 2) one or more codons coding for an amino acid, and 3) a translation stop codon, whereby it is understood that 1), 2) and 3) are operably linked in frame. The functional open reading frame will thus consist of a multiple of 3 nucleotides (triplets).

For the present invention, it is beneficial to be able to fine tune low levels of translational efficiency of the selectable marker polypeptide, so that the exact required level of stringency of selection is obtained. In the present invention this is brought about by varying the length of the functional open reading frame in the multicistronic transcription unit. In the constructs of the invention the functional open reading frame may thus encode at least 1, 2, 3, 4, 5, 6, 7, 8, 9, 10, 11, 12, 13, 14, 15, 20, 25, 30, 35, 40, 45, 50, 55, 60, 70, 80 or 90 amino acid residues and preferably encodes no more than 200, 180, 160, 150, 140, 130, 120, 110, 100, 99, 98, 97, 96, 95, 94, 93, 92, 91, or 90 amino acid residues with a startcodon at the 5' and a stopcodon at the 3' end. By thus varying the length of the functional open reading frame that immediately precedes the sequence encoding the selectable marker in the transcript, a near continuous range of translational efficiencies of the selectable marker is provided, as opposed to limited discrete steps in translational efficiency as disclosed in the prior art by applying suboptimal non-AUG initiation codons (see e.g. WO 2007/096399).

The functional open reading frame may be located immediately upstream of the separate startcodon of the selectable marker, in which case the stopcodon of the functional open reading frame is immediately adjacent to the start codon of the sequence coding for the selectable marker. Alternatively the stopcodon of the upstream functional open reading frame and the startcodon of the sequence coding for the selectable marker may be separated by 1, 2, 3, 4, 5, 6, 7, 8, 9, 10, 12, 14, 16, 18, 19, 20, 25, 30, 35, 40, 45, 50, 60, 70, 80, 90, 100, 120, 140, 160 180, 200, 250, 300, 350 or more nucleotides. Variation of the length of the spacer sequence separating the stopcodon of the upstream functional open reading frame and the startcodon of the sequence coding for the selectable marker adds a further level of fine tuning of the translational efficiency of the selectable marker. The spacer sequence separating the stop codon of functional open reading frame and the separate translation initiation codon of the nucleotide sequence encoding the selectable marker is devoid of translation initiation codons. Preferably therefore, the spacer sequence lacks ATG codons. More preferably, the spacer sequence also lacks suboptimal non-ATG codons such as GTG, TTG, CTG, ATT, and ACG (see below) embedded in a Kozak sequence (see below). Most preferably, the spacer sequence is devoid of any of the ATG, GTG, TTG, CTG, ATT, and ACG codons. In a further preferred embodiment, the spacer sequence separating the stop codon of functional open reading frame and the separate translation initiation codon of the nucleotide sequence encoding the selectable marker is devoid of stopcodons, i.e. lacks TAA, TAG and TGA codons. An example of a spacer sequence is provided in SEQ ID NO: 28.

The functional open reading frame will thus at least encode one amino acid but will usually encode a small peptide of which the length may vary as indicated above, i.e. 2-200 or more amino acids. The functional open reading frame may encode any amino acid or amino acid sequence. The amino acid sequence encoded in the functional open reading frame may e.g. be taken from any known protein coding sequence or other naturally occurring ORFs or it may be partially or completely artificial. Preferably however expression of the amino acid sequence encoded in the functional open reading frame is not harmful to the eukaryotic host cell, i.e. the amino acid sequence is of a non-toxic and preferably inert peptide. For example, the amino acid sequence encoded in the functional open reading frame may be arbitrarily taken from any protein coding gene, such as e.g. a luciferase gene (SEQ ID NO: 12). The amino acid sequence encoded in the functional open reading frame may thus be a fragment from a luciferase amino acid sequence (SEQ ID NO: 24), preferably a fragment from the pp.sup.x amino acids sequence (SEQ ID NO: 25). Alternatively, it may be randomly synthesized, e.g. by PCR using random primers. To further slow down the ribosome during translation of the functional open reading frame, the encoded amino acid sequence may comprise homopolymer stretches or be enriched in one particular amino acid.

A nucleic acid construct of the invention can be present in the form of double stranded DNA, having with respect to the selectable marker and the functional open reading frame encoding peptide a coding strand and a non-coding strand, the coding strand being the strand with the same sequence as the translated RNA, except for the presence of T instead of U. Hence, an AUG startcodon is coded for in the coding strand by an ATG sequence, and the strand containing this ATG sequence corresponding to the AUG startcodon in the RNA is referred to as the coding strand of the DNA. It will be clear to the skilled person that startcodons or translation initiation sequences are in fact present in an RNA molecule, but that these can be considered equally embodied in a DNA molecule coding for such an RNA molecule; hence, wherever the present invention refers to a startcodon or translation initiation sequence, the corresponding DNA molecule having the same sequence as the RNA sequence but for the presence of a T instead of a U in the coding strand of said DNA molecule is meant to be included, and vice versa, except where explicitly specified otherwise. In other words, a startcodon is for instance an AUG sequence in RNA, but the corresponding ATG sequence in the coding strand of the DNA is referred to as startcodon as well in the present invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

In a preferred embodiment, at least one of the translation initiation codons of the nucleotide sequence encoding the selectable marker and the functional open reading frame is an ATG codon. More preferably at least the initiation codon of the nucleotide sequence encoding the functional open reading is an ATG codon, in which case the initiation codon of the nucleotide sequence encoding the selectable marker can be a non-ATG startcodon (also known as suboptimal or less-favorable translation initiation codon), in order to allow for even more stringent selection (see below). Most preferably both the translation initiation codons of the nucleotide sequence encoding the selectable marker and the functional open reading frame are ATG codons. However, the invention does not exclude that the initiation codon of the nucleotide sequence encoding the functional open reading is a non-ATG startcodon.

A non-ATG startcodon is herein understood as a translation initiation codon comprising a mutation in the startcodon that decreases the translation initiation efficiency of the selectable marker polypeptide in a eukaryotic host cell. Examples of non-ATG start codons that may be used for the coding sequence of the selectable marker in the invention include e.g. GTG, TTG, CTG, ATT, and ACG. In a preferred embodiment, the ATG startcodon is mutated into a GTG startcodon. More preferably, the ATG startcodon is mutated to a TTG startcodon, which provides even lower expression levels of the selectable marker polypeptide than with the GTG startcodon (see also examples 9-13 in WO 2006/048459, incorporated by reference herein). When using a non-ATG startcodon, it is strongly preferred that the non-ATG start codon is present in an optimal context for translation initiation codon, such as a Kozak consensus sequence as herein defined below. When applying a non-ATG startcodon for the selectable marker the nucleotide sequence coding for the selectable marker can be mutated to be devoid of internal ATG codons, particularly devoid of internal ATG codons that are in frame with the non-ATG start codon. This is preferred in constructs wherein the selectable marker is upstream of a nucleotide sequence coding for a gene product of interest without using an IRES in between the sequences coding for the gene of interest and the marker and the gene product. WO 2006/048459 discloses how to bring this about (e.g. by substitution, insertion or deletion, preferably by substitution) and how to test the resulting selectable marker polypeptides for functionality. In the nucleic acid constructs of the invention it is further preferred that the use of non-ATG startcodons for the functional open reading frame is avoided, particularly so if the start codon for the downstream selectable marker is an ATG codon, as this will likely not result in an appreciable decrease in translation efficiency of the selectable marker.

In one embodiment, at least one of the initiation codons of the nucleotide sequence encoding the selectable marker and the functional open reading frame is embedded in a Kozak consensus sequence. The Kozak consensus sequence (for vertebrate host cells) is herein defined as ANN(AUG)N(SEQ ID NO: 29) and GNN(AUG)G (SEQ ID NO: 30), wherein (AUG) stands for the initiation codon of the relevant coding sequence. Preferably, both N's preceding the (AUG) are C's. A more preferred Kozak consensus sequence is GCCRCC(AUG)G (SEQ ID NO: 31), wherein R is a purine. In a further preferred embodiment, the Kozak consensus sequence may be preceded by yet another GCC triplet.

The term "selectable marker" is a term familiar to one of ordinary skill in the art and is used herein to describe any genetic entity which, when expressed, can be used to select for a cell or cells containing the selectable marker. Selectable markers may be dominant or recessive or bidirectional. The selectable marker may be a gene coding for a product which confers to a cell expressing the gene resistance to a selection agent such as e.g. an antibiotic or herbicide. The selectable marker may e.g. encode a selection protein that is able to neutralize or inactivate a toxic selection agent and protects the host cell from the agent's lethal or growth-inhibitory effects. Other selectable markers complement a growth-inhibitory deficiency in the cell under certain conditions. Examples of such genes include a gene which confers prototrophy to an auxotrophic strain. The term "reporter" is mainly used to refer to visible markers, such as green fluorescent protein (GFP), eGFP, luciferase, GUS and the like, as well as nptII markers and the like. Such reporters can be used for selecting cells expressing the visible marker by actively sorting cells expressing the marker from cells that do not, e.g. using a fluorescence activated cell sorter (FACS) for selecting cells that express a fluorescent marker protein. Preferably, the selectable marker according to the invention provides resistance against lethal and/or growth-inhibitory effects of a selection agent.

A nucleotide sequence encoding a selectable marker for use in the present invention encodes a protein that can be used for selection of eukaryotic host cells, e.g. because upon expression of the protein in the host cell it provides a growth advantage to the host cells expressing the selectable marker protein, as compared to host that do not. A preferred nucleotide sequence encoding a selectable marker provides resistance to a selection agent (e.g. an antibiotic) upon expression of the encoded selectable marker protein in the host cell, which selection agent causes lethality and/or growth inhibition of host cells not expressing the selectable marker protein. The selectable marker according to the invention must thus be functional in a eukaryotic host cell, and hence being capable of being selected for in eukaryotic host cells. Any selectable marker polypeptide fulfilling this criterion can in principle be used according to the present invention. Such selectable markers are well known in the art and routinely used when eukaryotic host cell clones are to be obtained, and several examples are provided herein.

For convenience and as generally accepted by the skilled person, in many publications as well as herein, often the gene encoding for the selectable marker and the selectable marker that causes resistance to a selection agent is referred to as the 'selectable agent (resistance) gene' or 'selection agent (resistance) protein', respectively, although the official names may be different, e.g. the gene coding for the protein conferring resistance to neomycin (as well as to G418 and kanamycin) is often referred to as neomycin (resistance) (or neo') gene, while the official name is aminoglycoside 3'-phosphotransferase gene.

In a preferred embodiment of the invention, the selectable marker provides resistance against lethal or growth-inhibitory effects of a selection agent selected from the group consisting of the bleomycin family of antibiotics, puromycin, blasticidin, hygromycin, an aminoglycoside antibiotic, methotrexate, and methionine sulphoximine.

A nucleotide sequence encoding a selectable marker providing resistance to bleomycin family of antibiotics is e.g. a nucleotide sequence encoding a wild-type "ble" gene, including but not limited to Sh ble, Tn5 ble and Sa ble. An example thereof is depicted in SEQ ID NO: 1. In general the gene products encoded by the ble genes confer to their host resistance to the copper-chelating glycopeptide antibiotics of the bleomycin family, which are DNA-cleaving glycopeptides. Examples of antibiotics of the bleomycin family for use as selection agents in accordance with the present invention include but are not limited to bleomycin, phleomycin, tallysomycin, pepleomycin and Zeocin™.

A nucleotide sequence encoding a selectable marker providing resistance to puromycin, is e.g. a nucleotide sequence encoding a wild-type puromycin resistance protein as depicted in SEQ ID NO: 2.

A nucleotide sequence encoding a selectable marker providing resistance to blasticidin, is e.g. a nucleotide sequence encoding a wild-type blasticidin resistance protein as depicted in SEQ ID NO: 3.

A nucleotide sequence encoding a selectable marker providing resistance to hygromycin, is e.g. a nucleotide sequence encoding a wild-type hygromycin resistance protein as depicted in SEQ ID NO: 4.

A nucleotide sequence encoding a selectable marker providing resistance to the aminoglycoside antibiotic is e.g. a nucleotide sequence encoding a wild-type aminoglycoside 3'-phosphotransferase as depicted in SEQ ID NO: 5. An aminoglycoside according to the present invention are the commonly known aminoglycoside antibiotics (Mingeot-Leclercq, M. et al., 1999, Chemother. 43: 727-737) comprising at least one amino-pyranose or amino-furanose moiety linked via a glycosidic bond to the other half of the molecule. Their antibiotic effect is based on inhibition of protein synthesis. Examples of aminoglycoside antibiotics for use as selection agents in accordance with the present invention include but are not limited Kanamycin, Streptomycin, Gentamicin, Tobramycin, G418 (Geneticin), Neomycin, Neomycin B (Framycetin), Sisomicin, Amikacin, Isepamicin and the like.

Other examples of selectable markers which can be used in the invention are selectable markers which may be used as auxotrophic (metabolic) selection markers and include e.g. a cystathionine gamma-lyase gene, a DHFR gene and a glutamine synthetase (GS) gene. A potential advantage of the use of these types of metabolic enzymes as selectable marker polypeptides is that they can be used to keep the host cells under continuous selection, which may advantageous under certain circumstances (see also below).

A nucleotide sequence encoding a selectable marker providing resistance to methotrexate, is e.g. a nucleotide sequence encoding a wild-type dihydrofolate reductase (DHFR) as depicted in SEQ ID NO: 6. The DHFR gene, which can be selected for by methotrexate, especially by increasing the concentration of methotrexate cells can be selected for increased copy numbers of the DHFR gene. The DHFR gene may also be used to complement a DHFR-deficiency, e.g. in CHO cells that have a DHFR⁻ phenotype, in a culture medium with folate and lacking glycine, hypoxanthine and thymidine, or at least lacking hypoxanthine and thymidine. If the selectable marker is DHFR, the host cell in advantageous embodiments is cultured in a culture medium that contains folate and which culture medium is essentially devoid of hypoxanthine and thymidine, and preferably also of glycine. In general, with "culture medium is essentially devoid" is meant herein that the culture medium has insufficient of the indicated component present to sustain growth of the cells in the culture medium, so that a good selection is possible when the genetic information for the indicated enzyme is expressed in the cells and the indicated precursor component is present in the culture medium. Preferably, the indicated component is absent from the culture medium. A culture medium lacking the indicated component can be prepared according to standard methods by the skilled person or can be obtained from commercial media suppliers.

A nucleotide sequence encoding a selectable marker providing resistance to methionine sulphoximine, is e.g. a nucleotide sequence encoding a wild-type human or mouse glutamine synthetase (GS) as depicted in SEQ ID NO: 7 or 8. The glutamine synthetase (GS) gene, for which selection is possible in cells having insufficient GS (e.g. NS—O cells) by culturing in media without glutamine, or alternatively in cells having sufficient GS (e.g. CHO cells) by adding an inhibitor of GS, methionine sulphoximine (MSX).

A nucleotide sequence encoding a selectable marker that is crucial for the synthesis of the amino acid L-cysteine, e.g. a nucleotide sequence encoding a wild-type human or mouse cystathionine gamma-lyase (EC 4.4.1.1) as depicted in SEQ ID NO: 9. CHO cells are natural auxotrophs for the conversion of cysthathionine to cysteine. Therefore, the cysta-thionine gamma-lyase (cys-lyase) gene can be used for selection of cells by complementation by culturing cells in media without L-cysteine and L-cystine. Selection on the basis of the cys-lyase marker may require the non-toxic precursor L-cystathionin to be present in the culture medium. The use of cys-lyase as selectable marker in some vertebrate cell lines may first require inactivation (knock-out) of the endogenous cystathionine gamma-lyase genes.

Further selectable markers and their selection agents that could be used in the context of the present invention, are for instance described in Table 1 of U.S. Pat. No. 5,561,053, incorporated by reference herein; see also Kaufman, Methods in Enzymology, 185:537-566 (1990), for a review of these selectable markers and their selection agents.

The term "selection" is typically defined as the process of using a selectable marker and a selection agent to identify host cells with specific genetic properties (e.g. that the host cell contains a transgene integrated into its genome). It is clear to a person skilled in the art that numerous combinations of selection markers are possible. One antibiotic that is particularly advantageous as a selection agent is zeocin, because the zeocin-resistance protein (zeocin-R) acts by binding the drug and rendering it harmless. Therefore it is easy to titrate the amount of drug that kills cells with low levels of zeocin-R expression, while allowing the high-expressors to survive. Most if not all other antibiotic-resistance selectable markers in common use are enzymes, and thus act catalytically (i.e. not in a given, e.g. 1:1, stoichiometry with the selection agent). Hence, the antibiotic zeocin is a preferred selectable marker.

In one embodiment, alternatively or in combination with a decreased translation initiation efficiency, it can be beneficial to also provide for decreased translation elongation efficiency of the selectable marker polypeptide. This may be achieved by e.g. mutating the sequence coding the selectable marker polypeptide so as to decrease the adaptation of the codon usage to the host cell in question. This again provides a further level of controlling the stringency of selection of the nucleic acid constructs of the invention. Thus, a nucleotide sequence encoding a selectable marker protein, is preferably adapted to a codon usage to that is suboptimal in host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). An codon adapted nucleotide sequence in accordance with the present invention preferably has a CAI of no more than 0.7, 0.6, 0.5, 0.4, 0.3 or 0.2.

In one embodiment, alternatively or in combination with the above described embodiments of the invention, mutants or derivatives of selectable markers are suitably used according to the invention, and are therefore included within the scope of the term 'selectable marker', as long as the selectable marker is still functional. Mutants or derivatives of a selectable marker preferably have reduced activity of the selectable marker compared to its wild-type counterpart allowing a further level of control in fine tuning of the stringency of selection of the nucleic acid constructs of the invention. Alternatively or in combination with one or more other embodiments, in a preferred embodiment, the nucleotide sequence encoding the selectable marker encodes a selectable marker polypeptide comprising one or more mutations that (collectively) reduce the activity of the selectable marker polypeptide compared to its wild-type counterpart. The activity of the mutated selectable marker polypeptide can be or more than 90, 80, 70, 60, 50, 40, 30, 20, 10, 5 or 1% to its wild-type counterpart.

As non-limiting examples, proline at position 9 in the zeocin resistance polypeptide may be mutated, e.g. to Thr or Phe (see e.g. example 14 of WO 2006/048459, incorporated by reference herein), and for the neomycin resistance polypeptide, amino acid residue 182 or 261 or both may further be mutated (see e.g. WO 01/32901).

In a preferred embodiment the selectable marker polypeptide with reduced activity is selected from the group consisting of: a) a zeocin resistance polypeptide wherein proline at position 9 is changed into a different amino acid; b) a zeocin resistance polypeptide wherein valine at position 10 is changed into a different amino acid; c) a zeocin resistance polypeptide wherein threonine at position 12 is changed into a different amino acid; d) a zeocin resistance polypeptide wherein arginine at position 14 is changed into a different amino acid; e) a zeocin resistance polypeptide wherein glutamic acid at position 21 is changed into a different amino acid; f) a zeocin resistance polypeptide wherein phenylalanine at position 22 is changed into a different amino acid; g) a zeocin resistance polypeptide wherein aspartic acid at position 25 is changed into a different amino acid; h) a zeocin resistance polypeptide wherein glycine at position 28 is changed into a different amino acid; i) a zeocin resistance polypeptide wherein phenylalanine at position 33 is changed into a different amino acid j) a zeocin resistance polypeptide wherein glycine at position 35 is changed into a different amino acid; k) a zeocin resistance polypeptide wherein glutamic acid at position 73 is changed into a different amino acid; l) a zeocin resistance polypeptide wherein alanine at position 76 is changed into a different amino acid; m) a zeocin resistance polypeptide wherein valine at position 82 is changed into a different amino acid; n) a zeocin resistance polypeptide wherein aspartic acid at position 88 is changed into a different amino acid; o) a zeocin resistance polypeptide wherein methionine at position 94 is changed into a different amino acid; and, p) a neomycin resistance polypeptide wherein at least one of amino acid residue 182 and 261 is changed into a different amino acid.

In a more preferred embodiment, the selectable marker polypeptide with reduced activity is selected from the group consisting of: a) a zeocin resistance polypeptide wherein proline at position 9 is changed into cysteine, glutamine or threonine; b) a zeocin resistance polypeptide wherein valine at position 10 is changed into alanine; c) a zeocin resistance polypeptide wherein threonine at position 12 is changed into alanine; d) a zeocin resistance polypeptide wherein arginine at position 14 is changed into proline; e) a zeocin resistance polypeptide wherein glutamic acid at position 21 is changed into glycine; f) a zeocin resistance polypeptide wherein phenylalanine at position 22 is changed into tyrosine; g) a zeocin resistance polypeptide wherein aspartic acid at position 25 is changed into glycine; h) a zeocin resistance polypeptide wherein glycine at position 28 is changed into arginine; i) a zeocin resistance polypeptide wherein phenylalanine at position 33 is changed into leucine j) a zeocin resistance polypeptide wherein glutamic acid at position 35 is changed into glycine; k) a zeocin resistance polypeptide wherein glutamic acid at position 73 is changed into glycine or lysine; l) a zeocin resistance polypeptide wherein alanine at position 76 is changed into threonine; m) a zeocin resistance polypeptide wherein valine at position 82 is changed into glutamic acid; n) a zeocin resistance polypeptide wherein aspartic acid at position 88 is changed into glycine; o) a zeocin resistance polypeptide wherein methionine at position 94 is changed into valine.

In an even more preferred embodiment, the selectable marker polypeptide with reduced activity is selected from the group consisting of: a) a zeocin resistance polypeptide wherein at least one of valine at position 10 is changed into alanine, threonine at position 12 is changed into alanine, and glutamic acid at position 35 is changed into glycine; b) a zeocin resistance polypeptide wherein at least one of arginine at position 14 is changed into proline, glutamic acid at position 73 is changed into lysine, and aspartic acid at position 88 is changed into glycine; c) a zeocin resistance polypeptide wherein at least one of glutamic acid at position 21 is changed into glycine, and alanine at position 76 is changed into threonine; d) a zeocin resistance polypeptide wherein at least one of glycine at position 28 is changed into arginine, and glutamic acid at position 73 is changed into glycine; and e) a zeocin resistance polypeptide wherein at least one of phenylalanine at position 22 is changed into tyrosine, and aspartic acid at position 25 is changed into glycine. An example of a wild type zeocin resistance polypeptide with respect to which the mutant polypeptides with reduced activity in the above embodiments can be defined is provided in SEQ ID NO: 10.

It will be clear that also encompassed in the invention are nucleic acid constructs of the invention as described above but having mutations in the sequence downstream of the first ATG (startcodon) coding for the selectable marker polypeptide as long as the respective encoded selectable marker protein still has activity, i.e. provides the required level of resistance to the selection agent. For instance any silent mutations that do not alter the encoded protein because of the redundancy of the genetic code are also encompassed. Further mutations that lead to conservative amino acid mutations or to other mutations are also encompassed, as long as the encoded protein still has activity, which may or may not be lower than that of the wild-type protein as encoded by the indicated sequences. In particular, it is preferred that the amino acid sequence of the encoded protein is at least 70%, preferably at least 80%, more preferably at least 90%, still more preferably at least 95% identical to the respectively indicated amino acid sequences (e.g. as provided in any one of SEQ ID NO.'s: 1-8). Testing for activity of the selectable marker proteins can be done by routine methods (see e.g. Examples 4 and 5 herein).

Examples of mutations in a cystathionine gamma-lyase (CLase) amino acid sequence that reduce CLase activity compared to the wild-type CLase counterpart are e.g. described by Wang and Hegele (2002, Hum. Genet. 112: 404-408) and include one or more of the mutations T67I, Q240E and S403I. Corresponding mutations in CLase amino acid sequences from other organisms are expressly included herein, such as e.g. the mutations T66I and Q239E.

In a second aspect, the present invention relates to an expression cassette comprising a nucleic acid construct according to invention, wherein the expression cassette comprises a promoter operably linked to the multicistronic transcription unit and a transcription termination sequence downstream of the multicistronic transcription unit, and wherein the promoter is functional in a eukaryotic host cell for initiating transcription of the multicistronic transcription unit.

An "expression cassette" as used herein is a nucleotide sequence comprising at least a promoter functionally linked to a sequence of which expression is desired. Preferably, an expression cassette further contains transcription termination and polyadenylation sequences. Other regulatory sequences such as enhancers may also be included. Hence, the invention provides an expression cassette preferably comprising in a 5' to 3' direction: 5'-promoter-multicistronic transcription unit according to the invention, comprising the functional open reading frame and downstream thereof sequence coding for a selectable marker polypeptide-transcription termination sequence-3'. The promoter, as well as the other regulatory sequences, must be capable of functioning in the eukaryotic host cell in question, i.e. it must be capable of driving transcription of the multicistronic transcription unit. The promoter is thus operably linked to the multicistronic transcription unit. The expression cassette may optionally further contain other elements known in the art, e.g. splice sites to comprise introns, and the like. In some embodiments, an intron is present behind the promoter and before the sequence encoding the functional open reading frame. In other embodiments, an IRES may be present in the multicistronic transcription unit that contains the selectable marker polypeptide coding sequence, which IRES may be operably linked to the functional open reading frame upstream of the selectable marker coding sequence or the IRES may be operably linked to a further cistron.

Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000, Mol. Biotechnol 16: 151-160). According to the present invention, strong promoters that give high transcription levels in the eukaryotic cells of choice are preferred. Some well-known and frequently used strong promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable e.g. from pcDNA, Invitrogen), promoters derived from Simian Virus 40 (SV40) (Das et al, 1985, Prog Nucleic Acid Res Mol Biol. 32: 217-36), and the like. Suitable strong promoters can also be derived from eukaryotic cells, such as methallothionein (MT) promoters, an elongation factor (EF-1α) promoter, an ubiquitin C or UB6 promoter (Gill et al., 2001, Gene Therapy 8: 1539-1546; Schorpp et al, 1996, Nucleic Acids Res 24: 1787-8), an actin promoter such as a β-actin promoter, e.g. a hamster or human β-actin promoter (SEQ ID NO: 11), an immunoglobulin promoter, a heat shock promoter and the like. Testing for promoter function and strength of a promoter is a matter of routine for a person skilled in the art, and in general may for instance encompass cloning a reporter gene such as lacZ, luciferase, GFP, etc. behind the promoter sequence, and test for expression of the reporter gene. Of course, promoters may be altered by deletion, addition, mutation of sequences therein, and tested for functionality, to find new, attenuated, or improved promoter sequences.

In a third aspect, the present invention relates to an expression vector comprising an expression cassette according the invention, preferably further comprising a nucleotide sequence coding for a gene product of interest. An expression vector (also known as expression system), e.g. a plasmid, can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art, and several aspects hereof have been described in WO 2006/048459 (e.g. pages 30-31), incorporated by reference herein.

It is widely appreciated that chromatin structure and other epigenetic control mechanisms may influence the expression of transgenes in eukaryotic cells (e.g. Whitelaw et al, 2001, Methods Mol Biol 158: 351-68). The nucleic acid constructs, expression cassettes and vectors according to the invention form part of selection systems with a rather rigorous selection regime. This generally requires high transcription levels in the host cells of choice. To increase the chance of finding clones of host cells that survive the rigorous selection regime, and possibly to increase the stability of expression in obtained clones, it will generally be preferable to increase the predictability of transcription. Therefore, in preferred embodiments, an expression cassette according to the invention further comprises at least one chromatin control element. A 'chromatin control element' as used herein is a collective term for DNA sequences that may somehow have an effect on the chromatin structure and therewith on the expression level and/or stability of expression of transgenes in their vicinity (they function 'in cis', and hence are placed preferably within 5 kb, more preferably within 2 kb, still more preferably within 1 kb from the transgene) within eukaryotic cells. Such elements have sometimes been used to increase the number of clones having desired levels of transgene expression. Several types of such elements that can be used in accordance with the present invention have been described in WO 2006/048459 (e.g. page 32-34), incorporated by reference herein, and for the purpose of the present invention chromatin control elements are chosen from the group consisting of matrix or scaffold attachment regions (MARs/SARs), insulators such as the beta-globin insulator element (5' HS4 of the chicken beta-globin locus), scs, scs', and the like, a ubiquitous chromatin opening element (UCOE), and anti-repressor sequences (also referred to as 'STAR' sequences).

Preferably, said chromatin control element is an anti-repressor sequence, preferably chosen from the group consisting SEQ. ID. NO. 1 to SEQ. ID. NO. 66 as disclosed in WO 2007/096399. More preferably, said chromatin control element is chosen from the group consisting of STAR67, STAR7, STAR5, STAR17, STAR27, STAR29, STAR43, STAR44, STAR45, STAR47, STAR61, as disclosed in WO 2007/096399 or a functional fragment or derivative of said STAR sequences. In a most preferred embodiment, a combination of STAR7 and STAR 67 is used, or functional fragments or derivatives of STAR7 and STAR67. In certain preferred embodiments, at least one of STAR7 and STAR 67 or a functional fragment or derivative thereof is positioned upstream of a promoter driving expression of the multicistronic transcription unit. In other preferred embodiments, the expression cassettes according to the invention are flanked on both sides by at least one the anti-repressor sequence as described above. In certain embodiments, expression cassettes are provided according to the invention, comprising in 5' to 3' order: anti-repressor sequence A-anti-repressor sequence B-[promoter-multicistronic transcription unit according to the invention (encoding the gene product of interest and downstream thereof the functional selectable marker protein)-transcription termination sequence]-anti-repressor sequence C, wherein A, B and C may be the same or different. In a preferred embodiment A and C are STAR7 and B is STAR67. Sequences having anti-repressor activity (anti-repressor sequences) and characteristics thereof, as well as functional fragments or derivatives thereof, and structural and functional definitions thereof, and methods for obtaining and using them, which sequences are useful for the present invention, have been described in WO 2006/048459 (e.g. page 34-38), incorporated by reference herein.

Another preferred gene expression enhancing element (that may be used in stead of the above-mentioned chromatin control elements or anti-repressor sequences) for use in the present invention is a nucleic acid fragment which functions as a source for intergenic transcription. Preferably the nucleic acid fragment which functions as a source for intergenic transcription comprising at least 1,000, 1,500, 2,000, 3,500 or 7,000 consecutive nucleotides of a genomic region that is present upstream of the translation initiation site of a vertebrate Rb1 or P15 gene and functions as a source for intergenic transcription. Preferably the nucleic acid fragment comprises at least 1,000, 1,500, 2,000, 3,500 or 7,000 consecutive nucleotides of SEQ ID NO: 35 (human Rb1F and E) consisting of a nucleotide sequences present about 7 kb upstream of the translation initiation site of the human Rb1 gene. More preferably the nucleic acid fragment comprises at least 1,000, 1,500, 2,000, 2,500, 3,000 or 3,498 consecutive nucleotides of SEQ ID NO: 36 (human Rb1E) (see also Examples herein). Alternatively preferred, the nucleic acid fragment comprises at least 1,000, 1,500, 2,000, 2,500, 3,000 or 3,352 consecutive nucleotides of SEQ ID NO: 37 (human P15C). In certain embodiments, expression cassettes are provided according to the invention, comprising in 5' to 3' order: a nucleic acid fragment which functions as a source for intergenic transcription A-[promoter-multicistronic transcription unit according to the invention (encoding the gene product of interest and a CLase selectable marker)-transcription termination sequence]-a nucleic acid fragment which functions as a source for intergenic transcription B, wherein A and B may be the same or different. In a preferred embodiment A and B are SEQ ID NO: 36, or A and B are SEQ ID NO: 37, or A and B are a sub fragment of one of SEQ ID NO's: 36 and 37 as indicated above.

A gene product of interest according to the invention can be any gene product, e.g. a protein. A gene product of interest may be a monomeric protein or a (part of a) multimeric protein. A multimeric protein comprises at least two polypeptide chains. Non-limiting examples of a protein of interest according to the invention are enzymes, hormones, immunoglobulins or chains or fragments thereof, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

A gene product of interest may be from any source, and in certain embodiments is a mammalian protein, an artificial protein (e.g. a fusion protein or mutated protein), and preferably is a human protein.

In a preferred embodiment, a nucleotide sequence encoding a gene product of interest is codon optimized for the host cell in which the peptide of interest is to be expressed, using the codon adaptation index of the host cell.

In one embodiment, an expression cassette of the present invention is used when the ultimate goal is not the production of a polypeptide of interest, but rather an RNA molecule, e.g. for producing increased quantities of RNA from an expression cassette, which may be used for purposes of regulating other genes (e.g. RNAi, antisense RNA), gene therapy, in vitro protein production, etc.

For the production of multimeric proteins, two or more expression cassettes can be used. Preferably, both expression cassettes are multicistronic expression cassettes according to the invention, each coding for a different selectable marker protein, so that selection for both expression cassettes is possible. This embodiment has proven to give good results, e.g. for the expression of the heavy and light chain of antibodies. It will be clear that both expression cassettes may be placed on one nucleic acid molecule or both may be present on a separate nucleic acid molecule, before they are introduced into host cells. An advantage of placing them on one nucleic acid molecule is that the two expression cassettes are present in a single predetermined ratio (e.g. 1:1) when introduced into host cells. On the other hand, when present on two different nucleic acid molecules, this allows the possibility to vary the molar ratio of the two expression cassettes when introducing them into host cells, which may be an advantage if the preferred molar ratio is different from 1:1 or when it is unknown beforehand what is the preferred molar ratio, so that variation thereof and empirically finding the optimum can easily be performed by the skilled person. According to the invention, preferably at least one of the expression cassettes, but more preferably each of them, comprises a chromatin control element, more preferably an anti-repressor sequence.

In another embodiment, the different subunits or parts of a multimeric protein are present on a single expression cassette. Useful configurations of anti-repressors combined with expression cassettes have been described in WO 2006/048459 (e.g. page 40), incorporated by reference herein.

In a preferred embodiment, the nucleotide sequence coding for the gene product of interest is comprised in the multicistronic transcription unit. In the multicistronic transcription unit, the nucleotide sequence coding for the gene product of interest may be located upstream of (i.e. 5' to) the functional open reading frame and selectable marker. Preferably, the nucleotide sequence coding for the gene product of interest is located downstream of (i.e. 3' to) the selectable marker. In these situations multicistronic transcription unit is preferably configured such that the upstream open reading frame(s) are translated in a cap-dependent manner, whereas the one or more downstream open reading frame(s) under translational control of an IRES. For example, if the nucleotide sequence coding for the gene product of interest is located upstream of the functional open reading frame and selectable marker, the sequence coding for the gene product of interest is translated in a cap-dependent manner and the functional open reading frame is under translational control of an IRES. Vice versa, if the nucleotide sequence coding for the gene product of interest is located downstream of the selectable marker, the functional open reading frame is translated in a cap-dependent manner and the sequence coding for the gene product of interest is under translational control of an IRES. The coding sequence(s) upstream of the IRES comprise a stopcodon, so that translation ends upstream of an IRES, which IRES is operably linked to the downstream codon sequences. Internal ribosome binding site (IRES) elements are known from viral and mammalian genes (Martinez-Salas, 1999, Curr Opin Biotechnol 10: 458-464), and have also been identified in screens of small synthetic oligonucleotides (Venkatesan & Dasgupta, 2001 Mol Cell Biol 21: 2826-2837). The IRES from the encephalomyocarditis virus has been analyzed in detail (Mizuguchi et al., 2000, Mol Ther 1: 376-382). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas, 1999, supra).

In one embodiment, an expression vector according to the invention comprises an additional selection marker, e.g. a dhfr metabolic selection marker as described supra. An advantage of such a nucleic acid construct is that selection of a host cell with high expression can be established by use of a selection marker operably linked with an IRES, e.g. zeocin, neomycin, etc, whereas after the selection of a host cell with high expression the antibiotic selection is discontinued and either continuous or intermittent selection is done using the additional selection marker. The multicistronic transcription units in this aspect are at least tricistronic.

It is preferred to use separate transcription units for the expression of different gene products of interest, also when these form part of a multimeric protein (see e.g. example 13 of WO 2006/048459, incorporated by reference herein: the heavy and light chain of an antibody each are encoded by a separate transcription unit, each of these expression units being a bicistronic expression unit). When two multicistronic transcription units are to be selected for according to the invention in a single host cell, each one preferably contains the coding sequence for a different selectable marker, to allow selection for both multicistronic transcription units. Of course, both multicistronic transcription units may be present on a single nucleic acid molecule or alternatively each one may be present on a separate nucleic acid molecule.

In a fourth aspect, the present invention relates to a eukaryotic host cell comprising a nucleic acid construct according to the invention, an expression cassette according to the invention or an expression vector according to the invention.

The terms "cell" or "host cell" and "cell line" or "host cell line" are respectively defined as a cell and homogeneous populations thereof that can be maintained in cell culture by methods known in the art, and that have the ability to express heterologous or homologous proteins. The host is an eukaryotic host cell such as a cell of fungal, insect or vertebrate origin. More preferably the host cell is a mammalian cell. Several exemplary host cells that can be used have been described in WO 2006/048459 (e.g. page 41-42), incorporated by reference herein, and such cells include for instance mammalian cells, including but not limited to CHO cells, e.g. CHO-K1, CHO—S, CHO-DG44, CHO-DG44-S, CHO-DUKXBI 1, including CHO cells having a dhfr⁻ phenotype, as well as myeloma cells (e.g. Sp2/0, NS0), HEK 293 cells, HEK 294 cells, and PER.C6 cells.

Such eukaryotic host cells can express desired gene products, and are often used for that purpose. They can be obtained by introduction of a nucleic acid construct of the invention, preferably in the form of an expression cassette or an expression vector according to the invention, into the cells. Preferably, the expression cassette is integrated in the genome of the host cell, which can be in different positions in various host cells, and selection will provide for a clone where the transgene is integrated in a suitable position, leading to a host cell clone with desired properties in terms of expression levels, stability, growth characteristics, and the like.

Alternatively the multicistronic transcription unit may be targeted or randomly selected for integration into a chromosomal region that is transcriptionally active, e.g. behind a promoter present in the genome. Selection for cells containing the DNA of the invention can be performed by selecting for the selectable marker polypeptide, using routine methods known by the person skilled in the art. When such a multicistronic transcription unit is integrated behind a promoter in the genome, an expression cassette according to the invention can be generated in situ, i.e. within the genome of the host cells.

Preferably the host cells are from a stable clone that can be selected and propagated according to standard procedures known to the person skilled in the art. A culture of such a clone is capable of producing gene product of interest, if the cells comprise the multicistronic transcription unit of the invention.

Introduction of nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like. Suitable host cells that express the gene product of interest can be obtained by selection.

In preferred embodiments, a nucleic acid construct according to the invention, preferably in the form of an expression cassette, is integrated into the genome of the eukaryotic host cell according to the invention. This will provide for stable inheritance of the multicistronic transcription unit.

In a fifth aspect, the present invention relates to a method of generating a eukaryotic host cell for expression of a gene product of interest, wherein the method comprises the steps of: a) introducing into a plurality of host cells an expression vector according to the invention; b) culturing the plurality of host cells obtained in a) under conditions selecting for expression of the selectable marker polypeptide; and, c) selecting at least one host cell expressing the selectable marker polypeptide for expression of the gene product of interest.

Advantages of this method are similar to those described for the method disclosed in WO 2006/048459 (e.g. page 46-47), incorporated by reference herein. While clones having relatively low copy numbers of the multicistronic transcription units and high expression levels can be obtained, the selection system of the invention nevertheless can be combined with amplification methods to even further improve expression levels. This can for instance be accomplished by amplification of a co-integrated DHFR gene using methotrexate, for instance by placing DHFR on the same nucleic acid molecule as the multicistronic transcription unit of the invention, or by cotransfection when dhfr is on a separate DNA molecule. The DHFR gene can also be part of a multicistronic expression unit of the invention.

Selection for the presence of the selectable marker polypeptide, and hence for expression, can be performed during the initial obtaining of the host cell. In certain embodiments, the selection agent is present in the culture medium at least part of the time during the culturing, either in sufficient concentrations to select for cells expressing the selectable marker polypeptide or in lower concentrations.

In a sixth aspect, the present invention relates to a method of expressing a gene product of interest, comprising culturing a host cell comprising an expression vector according to the invention, and expressing the gene product of interest from the expression vector. In preferred embodiments, selection agent is no longer present in the culture medium during final the production phase of gene product of interest so as to avoid any risk of contamination of the gene product with trace of the possibly noxious selection agent.

In a further preferred embodiment the expression vector comprises an auxotrophic (or metabolic) selection marker and the host cell is cultured under conditions that are selective for expression of the auxotrophic selection marker. Preferably the auxotrophic selection marker in the expression vector is a stringent auxotrophic selection marker as herein defined above. Thus the nucleotide encoding the auxotrophic marker may be comprised in a nucleic acid construct comprising a multicistronic transcription unit, which unit comprises a) a nucleotide sequence encoding the auxotrophic selection marker; and b) a functional open reading frame, wherein the nucleic acid construct comprising the multicistronic transcription unit is as further defined herein above (i.e. a $pp^x$ construct). Alternatively, or in combination therewith, the nucleotide encoding the auxotrophic marker may comprise a non-ATG translation initiation codon as herein defined above, and/or the nucleotide encoding the auxotrophic marker may encode a variant of the auxotrophic marker having reduce enzymatic activity as compared to the corresponding wild-type enzyme e.g. as herein defined above for the CLase marker.

An auxotrophic selection marker is herein defined as a nucleotide sequence encoding an enzyme that metabolizes one or more essential steps in the (bio)synthesis of a compound, usually an organic compound (e.g. a metabolite), required for growth of the auxotrophic cell. By expression of the auxotrophic selection marker, the auxotrophic host cell is converted to a prototroph that is able to grow under selective conditions wherein compound required for growth of the auxotrophic cell is absent, or present at a concentration that reduces the growth rate of the auxotrophic cell to an extent that allows selection of host cells comprising the expression vector comprising the auxotrophic marker. Compounds required for growth of auxotrophs are often essential amino acids or nucleosides, which e.g. cannot be synthesized by the auxotrophic host cell, such as e.g. a mammalian cell. Preferably the compound required for growth is an amino acid, a nucleoside, a vitamin or a precursors for an amino acid, a nucleoside, or a vitamin.

Preferred nucleotide sequences encoding for auxotrophic (or metabolic) selection marker genes for use in the present invention include e.g. nucleotide sequences encoding a L-cystathionine γ-lyase (CLase), dihydrofolate reductase (DHFR) and glutamine synthase (GS), as defined herein above. A advantage of using auxotrophic/metabolic enzymes as selectable marker polypeptides is that they can be used to keep the host cells under continuous selective conditions while avoiding the use of toxic and/or expensive selection agents such as e.g. antibiotics. In this embodiment of the method the selectable marker is used as maintenance marker. Conditions that are selective for expression of the auxotrophic selection marker will usually be conditions wherein the compound required for growth of auxotrophic host cell is absent from the culture medium and wherein preferably one or more precursor for the biosynthesis of the compound by the auxotrophic selection marker enzyme are present in the culture medium. Selective conditions for the DHFR marker include the presence of folate and the absence of glycine, hypoxanthine and thymidine, or at least the absence of hypoxanthine and thymidine in the culture medium. Selective conditions for the DHFR marker include the absence of glutamine in the culture medium. Selective conditions for the CLase marker include the absence of L-cysteine and L-cystine and preferably the presence of L-cystathionine.

The auxotrophic host cell to be used in the method for producing a gene product under selective conditions may be a host cell that is a natural auxotroph. Alternatively the host cell may be made into an auxotrophic host cell by inactivation (knock-out) of endogenous genes coding for the auxotrophic marker enzyme. Alternatively, in the method the host cell is cultured under conditions selecting for expression of auxotrophic marker activity as defined herein above, which may further include the presence of an inhibitor of auxotrophic marker activity. Thus, in a preferred method the host cell is cultured in the presence of an inhibitor of auxotrophic marker activity. An inhibitors of GS activity is e.g. methionine sulphoximine (MSX) and inhibitors of CLase activity include e.g. aminoethoxyvinylglycine, propargylglycine, trifluoroalanine and L-beta-oxalyl-amino-L-alanine, of which propargylglycine is most preferred. In certain embodiments, an expression vector of the invention encodes an immunoglobulin heavy or light chain or an antigen binding part, derivative and/or analogue thereof. In a preferred embodiment a protein expression unit according to the invention is provided, wherein said protein of interest is an immunoglobulin heavy chain. In yet another preferred embodiment a protein expression unit according to the invention is provided, wherein said gene product of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression vectors, or on a single expression vector. Thus, the heavy and light chain can each be present on a separate expression vector, each having its own promoter (which may be the same or different for the two expression vectors), each comprising a multicistronic transcription unit according to the invention, the heavy and light chain being the gene product of interest, and preferably each coding for a different selectable marker protein, so that selection for both heavy and light chain expression vector can be performed when the expression vectors are introduced and/or present in a eukaryotic host cell. Alternatively, the heavy and light chain coding sequences can be present on a single expression vector comprising a multicistronic transcription unit according to the invention, driven from a single promoter, and wherein the light and heavy chains are the gene products of interest with an IRES in between their respective coding sequences.

Culturing a cell is done to enable it to metabolize, and/or grow and/or divide and/or produce gene products of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant gene products through cell culture it is preferred in the art to have cells capable of growing in suspension, and it is preferred to have cells capable of being cultured in the absence of animal- or human-derived serum or animal- or human-derived serum components.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, a method of expressing a gene product of interest according to the invention further comprises harvesting the gene product of interest. The expressed gene product, e.g. protein may be harvested, collected or isolated either from the cells or from the culture medium or from both. It may then be further purified using known methods, e.g. filtration, column chromatography, etc, by methods generally known to the person skilled in the art.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, $2^{nd}$ edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988. [0088] The invention is further explained in the following examples. The examples do not limit the invention in any way. They merely serve to clarify the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

BRIEF DESCRIPTION OF THE FIGURES

FIG. 2: Influence of the length of an upstream peptide on colony formation in the absence or presence of STAR elements. The same pp encoding luciferase stretches as used in FIG. 1/Example 2 ($pp^9$, $pp^{23}$, $pp^{54}$, $pp^{75}$ and $pp^{90}$) were placed immediately upstream of a gene encoding the zeocin selection marker. The novel pp-zeocin selection stringencies were compared with known zeocin selection markers that were modified at the translation initiation codon, e.g., the GTG and TTG translation codons. All constructs were tested in the presence and absence of flanking STARs 7 and 67 upstream of the expression cassettes and STAR 7 downstream of the expression cassettes. The various constructs are schematically depicted and the bars indicate the number of stably transfected zeocin resistant colonies obtained with the various constructs as indicated.

FIG. 3: The use of small peptides creates a high stringency selection system that can be used to achieve high protein expression levels. The novel zeocin selection markers with the same pp encoding luciferase stretches as used in FIG. 1/Example 2 ($pp^9$, $pp^{23}$, $pp^{54}$, $pp^{75}$ and $pp^{90}$) were placed behind an internal ribosome entry site (IRES). The Zeocin genes and IRES were placed downstream of the d2EGFP reporter gene, to determine the expression levels after selecting stably transfected clones. As controls the ATG Zeo gene (or $pp^0$) behind the IRES sequence was used and for comparison the constructs with the TTG Zeo-d2EGFP STAR-Select configuration were included. The various constructs are schematically depicted and the mean d2GFP expression levels in the zeocine resistant colonies are indicated (bars).

FIG. 6: Amino acid substitutions in various zeocin muteins with reduced activity. Figure discloses SEQ ID NOS 10 and 38-48, respectively, in order of appearance.

FIG. 9: Influence of zeocin mutations on reporter protein expression levels. Zeocin mutants as indicated were placed behind an internal ribosome entry site (IRES). The zeocin genes and IRES were placed downstream of the d2EGFP reporter gene, to determine the expression levels after selecting stably transfected clones. As controls the wild type zeocin gene (Zeo WT) behind the IRES sequence was used and for comparison the constructs with the ATG/GTG/TTG Zeo-d2EGFP STAR-Select configuration were included. The various constructs are schematically depicted and the mean d2GFP expression levels in the zeocine resistant colonies are indicated (bars).

FIG. 17: The use of small peptides to create a selection system using dhfr as marker for direct selection. The TTG Zeo marker was removed from the construct depicted in FIGS. 16A and 16B to test the dhfr proteins modified with small peptides as direct selection marker. In a control construct the GTG dhfr gene was placed downstream of the IRES sequence Constructs as depicted were transfected to CHO-DG44 cells and grown in the absence of HT supplement. The number of stable dhfr-dependent colonies was determined for the various constructs.

FIG. 18: The use of small peptides to create a selection system using dhfr as marker for direct selection. Mean d2EGFP fluorescence of dhfr-dependent colonies obtained with the constructs of FIG. 17 is determined.

In FIG. 19, (A) shows direct selection with cells expressing the same constructs and cultured in medium absent L-cysteine/L-cystine. EPO levels and the average doubling times at day 1 or day 45 is shown in (B).

Figure 1:
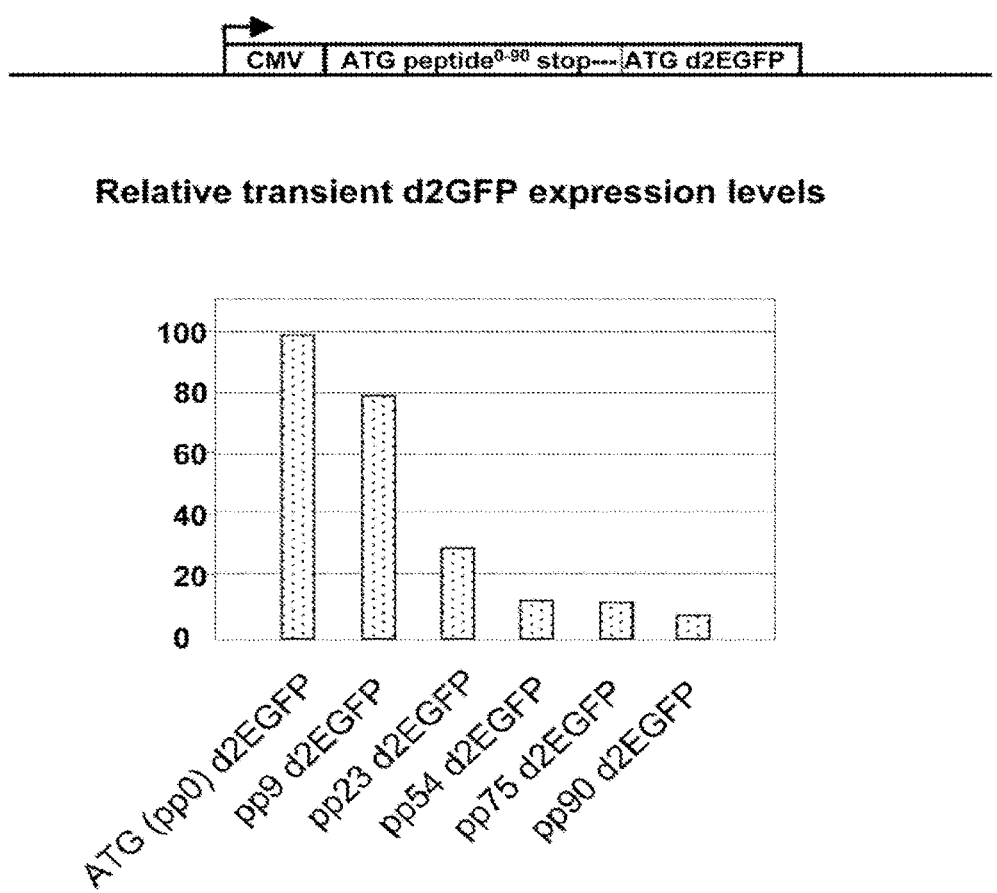
FIG. 1: Influence of the length of an upstream small peptide on transient expression. Stretches of DNA from the luciferase of four different lengths were cloned immediately upstream of ATG of the d2EGFP reporter gene. Each luciferase stretch contained a 5' ATG and was terminated by a TAA stop codon. The CMV promoter drove expression. Six different constructs were thus created, containing no peptide, or a small peptide (pp for 'petit peptide'). The constructs are a control construct, containing no peptide ($pp^0$), $pp^9$, $pp^{23}$, $pp^{54}$, $pp^{75}$ and $pp^{90}$. These constructs were transfected to CHO-K1. 24 hours after transfection cell were analyzed for d2EGFP protein expression by flowcytometry. The resulting fluorescence signal derived from the d2EGFP protein is linear with the amount of available d2EGFP protein in a cell and thus a reliable indicator of the d2EGFP expression levels in the cells.

A. Wild-type human U2 OS cells and human U2 OS cells transfected with a construct as depicted were grown in the absence or presence of $10^{-5}$ M aminoethoxyvinylglycine and in the absence or presence of $10^{-4}$ M L-cysteine and average cell divisions times under the various conditions were determined as indicated. B. Mean d2EGFP expression levels obtained with human U2 OS cells transfected with a construct as depicted, grown under the conditions as indicated and described in detail in Example 10.

EXAMPLES

1. Example 1: Placing Increasingly Longer Peptides Upstream of a Reporter Gene Results in Decreasing Protein Expression Levels The wild type Zeocin selection marker is translated from an ATG. In the current example this configuration has been preserved, but we placed small stretches of coding DNA upstream of this ATG. This piece of DNA was arbitrarily taken from the luciferase gene. Different lengths were taken, encoding respectively peptides of 9, 23, 54, 75 and 90 amino acids. Each stretch of DNA started with an optimal ATG to provide a translation initiation codon, and a TAA stop codon, which was placed upstream of the ATG of the Zeocin selection marker, with 19 nucleotides (SEQ ID NO: 28) between the stopcodon of the luciferase DNA stretch and the ATG of the Zeocin gene. The idea underlying these Zeocin gene configurations is that translation will be initiated at the ATG of the luciferase DNA stretch (or more accurately, at the AUG of the corresponding RNA), and stop again at the stop codon of the RNA stretches, this creating small non-functional luciferase peptides. However, since the peptides are relatively small, the translation machinery is likely to re-initiate translation when it encounters a second AUG present on the same messenger RNA, in this configuration at the start of the coding region for Zeocin. (Marilyn Kozak Nucleic Acids Research, 2001, vol. 29, No. 24, 5226-5232). This ability of the translation machinery will, however, become more and more difficult when the luciferase stretches become longer. Thus, a Zeocin selection marker mRNA coupled to a mRNA stretch encoding 9 amino acids will be less efficiently translated than when no extra mRNA stretch is present (wild type), but will still be more efficiently translated than a Zeocin selection marker mRNA coupled to a mRNA stretch encoding 90 amino acids. As a result, the last mentioned Zeocin marker (with a peptide of 90 amino acids) will functionally become a more stringent selection marker than the Zeocin selection marker harboring the 9 amino acids long small peptide, which in turn will be more stringent than the wild type Zeocin marker. The translation efficiency of the selection marker and thereby the selection stringency in this configuration depends on the length of the DNA stretch placed in front of the Zeocin selection marker.

In Example 1 we tested whether placing small peptides upstream of a reporter gene creates a system in which the expression levels of the reporter protein can be influenced.

1.1 Results

We isolated a stretch of DNA from the luciferase (accession number pGL3 Basic E1751, Promega; SEQ ID NO: 12) gene by PCR and four different lengths were cloned immediately upstream of ATG of the d2EGFP reporter gene (FIG. 1). Each primer that was used contained a 5' ATG and each DNA stretch was terminated by a TAA stop codon (see Table 1). Forward primers harbor an NheI site (Caps) and a ATG start codon. Reverse primers harbor an SpeI site (Caps) and a TAA stop codon. The start codons are shown in bold.

TABLE 1

PCR primer sequences amplifying $pp^x$ from the Luciferase gene.

| Primer | Sequence | SEQ ID NO |
|---|---|---|
| pp9-forward | aggcGCTAGCatgtgagaggtcctatgattatgtc | 22 |
| pp23-forward | aggcGCTAGCatggggaaaacgctgggcgttaatc | 21 |
| pp54-forward | aggcGCTAGCatggctattctgattacacccgag | 20 |
| pp75-forward | aggcGCTAGCatggccaagaggttccatctg | 19 |
| pp90-forward | aggcGCTAGCatggaaattgcttctggtggcgctc | 18 |
| luc stop-reverse | aggcACTAGTttaaccggacataatcataggac | 23 |

The CMV promoter drove expression. Six different constructs were thus created, containing no peptide, or a small peptide (pp for 'petit peptide'). The constructs are a control construct, containing no peptide (pp0), pp9 (SEQ ID NO: 17), pp23 (SEQ ID NO: 16), pp54 (SEQ ID NO: 15), pp75 (SEQ ID NO: 14) and pp90 (SEQ ID NO: 13). These constructs were transfected to CHO-K1 (ATCC Cat. No. CCl-61) cells with LIPOFECTAMINE 2000 (cationic liposomal transfection reagent, Invitrogen) etc. 4 µg DNA mixed with 6 µl LIPOFECTAMINE was added to 600.000 cells. 24 hours after transfection cell were analyzed for d2EGFP protein expression by flowcytometry (EPIXS-XL, Beckman-Coulter). The resulting fluorescence signal derived from the d2EGFP (destabilized) protein is linear with the amount of available d2EGFP protein in a cell, thus a reliable indicator of the d2EGFP expression levels in the cells.

As is shown in FIG. 1, placing a stretch of DNA encoding a small peptide upstream of the d2EGFP reporter gene had a profound and progressive effect on the d2EGFP expression levels. Inclusion of a 9 and 23 amino acid long peptide resulted in a decrease of d2EGFP expression to 80% and 30% respectively, of the d2EGFP expression level of the control construct (put at 100%). The d2EGFP expression levels decreased further when longer peptides were included, down to 10% of the control d2EGFP expression levels when a 90 amino acid peptide was placed upstream of the d2EGFP gene.

We conclude that placing small peptides that are defined by a 5'ATG and 3'TAA stop codon, upstream of a reporter gene results in decreased expression levels of the reporter protein.

2. Example 2: Placing Increasingly Longer Peptides Upstream of the Zeocin Selection Marker Results in a Decreasing Number of Stably Transfected Colonies We next placed increasingly longer luciferase DNA stretches immediately upstream of a gene encoding a selection marker. We did this to test whether this would create more stringent selection markers, due to the increasingly diminished protein expression levels of such selection marker. In this example we chose the Zeocin selection marker protein. We placed the described (see example 1) pp9, pp23, pp54, pp75 and pp90 DNA stretches of the luciferase gene immediately upstream of the Zeocin gene. In order to compare the novel Zeocin selection stringencies with known systems, we compared the constructs with Zeocin selection markers that were modified at the translation initiation codon, e.g., the GTG and TTG translation codons. These configurations are known as STAR-Select configurations. It has been found that in particular the selection stringency of the TTG Zeocin configuration is so high that only very few stably transfected colonies can form. To establish more stably transfected colonies, STAR elements have to be introduced to flank the expression cassette in the construct. The STAR elements elevate the activity of the promoter that drives the expression cassettes, thus increasing the Zeocin mRNA levels expression levels, which in turn allows the cell to survive more easily. Therefore, we tested all constructs in the presence and absence of flanking STAR elements. For ease of comparison, we placed STARs 7 and 67 upstream of the expression cassettes and STAR 7 downstream of the expression cassettes. This configuration has been reported to provide a favorable context for highly elevated protein expression levels in multiple cell lines and with different promoters.

2.1 Results

We placed five different luciferase small peptides encoding DNA stretches immediately upstream of the ATG of the Zeocin selection marker gene (FIG. 2). As control constructs we took the ATG Zeo (which is in fact a pp0 Zeo), the GTG Zeo and TTG Zeo selection markers. No reporter genes were included in these constructs that were all driven by the human β-actin promoter (FIG. 2). The same amount of DNA of all constructs was transfected to CHO-DG44 cells with LIPOFECTAMINE 2000 (cationic liposomal transfection reagent, Invitrogen) and selection was performed with 400 µg/ml Zeocin in the culture medium. The culture medium consisted of HAMF12:DMEM=1:1, +10% foetal bovine serum. After approximately two weeks the number of stably established colonies were counted. As shown in FIG. 2, transfection of the construct containing the ATG Zeo selection marker created most stable colonies (~1750) in the absence of STAR elements and >2500 in the presence of STAR elements. As expected, the inclusion of the GTG Zeo and TTG Zeo selection markers resulted in significantly less stable CHO DG44 colonies. GTG Zeo induced ~150 colonies in the absence and ~750 in the presence of STAR elements (FIG. 2). TTG Zeo induced ~10 colonies in the absence and ~40 in the presence of STAR elements (FIG. 2).

In comparison, inclusion of pp9 Zeo in the construct induced ~1000 colonies in the absence and >2000 in the presence of STAR elements (FIG. 2). Inclusion of longer peptides resulted in the formation of only a few stable colonies when no STAR elements were included in the construct. However, when STAR elements were added to flank the expression cassette, pp23, pp54, pp75 and pp90 still gave ~2000, ~1400, ~450 and ~100 stable colonies, respectively.

Thus, inclusion of increasingly longer peptides resulted in the establishment of a smaller number of stably transfected colonies. This indicates that with increasingly longer peptides the resulting Zeocin selection marker system becomes more stringent, presumably due to increasingly lower Zeocin protein expression levels. This is in agreement with the decreased d2EGFP protein expression levels in transient transfections (see Example 1) with increasing lengths of the peptides. This also indicates that the inclusion of independently translated small peptides in a protein expression system can be used for the creation of a stringent selection system for mammalian cells. Finally, we note that the number of stably transfected colonies with pp90 is in the same order as with the TTG Zeo selection marker. In either case hardly any stable colonies are formed in the absence of STAR elements and an increased, but still limited number of colonies when STAR elements are present. This indicates that the inclusion of the pp90 peptide creates a Zeocin selection system with approximately similar selection stringency as the TTG Zeo STAR-Select system.

3. Example 3: Placing Increasingly Longer Peptides Upstream of the Zeocin Selection Marker Results in Increased Expression Levels of a Reporter Protein We next placed the Zeocin selection markers behind an internal ribosome entry site (IRES). Between the IRES and the Zeocin coding region we placed increasingly longer luciferase DNA stretches. The Zeocin genes were placed downstream of the d2EGFP reporter gene, to determine the expression levels after selecting stably transfected clones (FIG. 3). As control construct we placed the ATG Zeo gene (or pp0) behind the IRES sequence. We also compared the constructs with the TTG Zeo-d2EGFP STAR-Select configuration. Since only small numbers of colonies are established when no STAR elements are included, we chose to only test constructs in which also STAR elements 7 and 67 were incorporated. The human β-actin promoter drove all expression cassettes.

3.1 Results

The same amount of DNA of all constructs were transfected to CHO-DG44 cells with LIPOFECTAMINE 2000 (cationic liposomal transfection reagent, Invitrogen) and selection was performed with 400 µg/ml Zeocin (Invitrogen) in the culture medium. The culture medium consisted of HAMF12: DMEM=1:1, +10% foetal bovine serum. Up to 24 independent colonies were isolated. Colonies were propagated before analysis by flow cytometric analysis (EPIXS-XL, Beckman-Coulter), 3 to 4 weeks after transfection. The fluorescence signal derived from d2EGFP (destabilized) is linear with the amount of available d2EGFP protein in a cell, and is thus a reliable indicator of the d2EGFP expression levels in the cell. In a single FACS analysis, fluorescence signals from a sample that contain up to 4000 cells are analyzed. One such sample of cells is taken from an independent, stably transfected cell colony. Since the signal will vary amongst the individual cells in the colony, the mean fluorescence level of the 4000 cells in the sample is taken as a measure for the d2EGFP expression level in the stably transfected cell colony.

As shown in FIG. 3, incorporation of increasingly longer peptides upstream of the Zeocin selection marker, gave significantly higher d2EGFP expression levels, as compared to the control construct with the ATG Zeo (pp0) marker. The average d2EGFP expression level in 12 independent colonies rose from 100 to 700 with the ATG (pp0)Zeo and pp90 Zeo marker, respectively. It is important to note that incorporation of the TTG Zeo selection marker in this same experiment resulted in an average d2EGFP expression level of 750. This is very similar to the average d2EGFP expression level that is achieved with the pp90 Zeo selection marker, indicating that these Zeocin marker configurations convey similar selection stringencies. We conclude that the inclusion of small DNA stretches that translate to small peptides upstream of a selection marker creates a potent selection system for mammalian cells.

4. Example 4: The Creation of Zeocin Mutant Proteins with Attenuated Ability to Neutralize Zeocin Another means to obtain higher selection stringency might be achieved by functionally impairing the selection marker protein. This implies that more selection marker protein has to be made in order to neutralize similar amounts of the selection agent in the culture medium. Higher levels of selection marker protein require higher mRNA levels of the selection marker and this may in turn result in higher expression levels of the protein of interest that is expressed in the transfected cell. Introducing mutations in the coding region of the protein may create functionally impaired selection marker proteins. In this example we systematically introduced mutations in the coding region of the Zeocin resistance marker and tested whether this created Zeocin marker proteins with different selection stringencies.

4.1 Results

We created mutations in the Zeocin resistance marker gene by PCR amplifying the gene in such a way that random mutations are introduced. More manganese and magnesium ions in the reaction mix, as well as an adjusted mix of nucleotides induce random mutations in the PCR product (Bloom J D, Silberg J J, Wilke C O, Drummond D A, Adami C, Arnold F H. Thermodynamic prediction of protein neutrality. Proc Natl Acad Sci USA. 2005 Jan. 18; 102(3):606-11). 50 ng of the pCMV/ZEO plasmid (Invitrogen, V50120) that harbors the Zeocin gene was amplified with 0.75 µM each of the following primers:

α97 (ATTAGGATCCACCATGGCCAAGTTGACCA-GTGCCG) and

α100 (ACCGGAATTCTCAGTCCTGCTCCTCGGC-CACG) SEQ ID NO.'s: 24 and 25, respectively. The reaction was performed in 7 mM MgCl2, 75 µM MnCl2, 0.2 mM dATP, 0.2 mM dGTP, 0.5 mM dTTP, 0.5 mM dCTP, 1× GOTag buffer (Promega) with 5 u GOTag polymerase (Promega). Amplification was for 10 to 40 cycles for 1 m in at 95° C., 1 min at 50° C., and 1 min at 72° C. The resulting Zeocin fragments derived from the PCR reaction was cut with BamH1 and EcoRI, and cloned behind the EM7 promoter in the pBS EM7 W4950 plasmid. This plasmid also harbors the Ampicillin resistance gene. E. coli (XL10) colonies were selected on 100 µg/ml ampicillin. The Ampicillin resistance gene was driven by its natural, beta lactamase promoter. Randomly chosen ampicillin-resistant recombinants were then plated on agar plates containing both 100 µg/ml ampicillin and 50 µg/ml Zeocin. The growth of the recombinants was then compared to the growth of E. coli XL10 transformed with the wild type Zeocin gene. Since the Ampicillin resistance gene is not affected by the PCR procedure on the Zeocin resistance gene, equal numbers of ampicillin-resistant colonies are to be expected, even if the Zeocin resistance gene is functionally totally destroyed by mutations. This results in a lower ratio of Zeo/Amp resistant colonies. Colonies showing impaired growth on Zeocin were then further characterized by plating them on various Zeocin concentrations.

Figure 4:
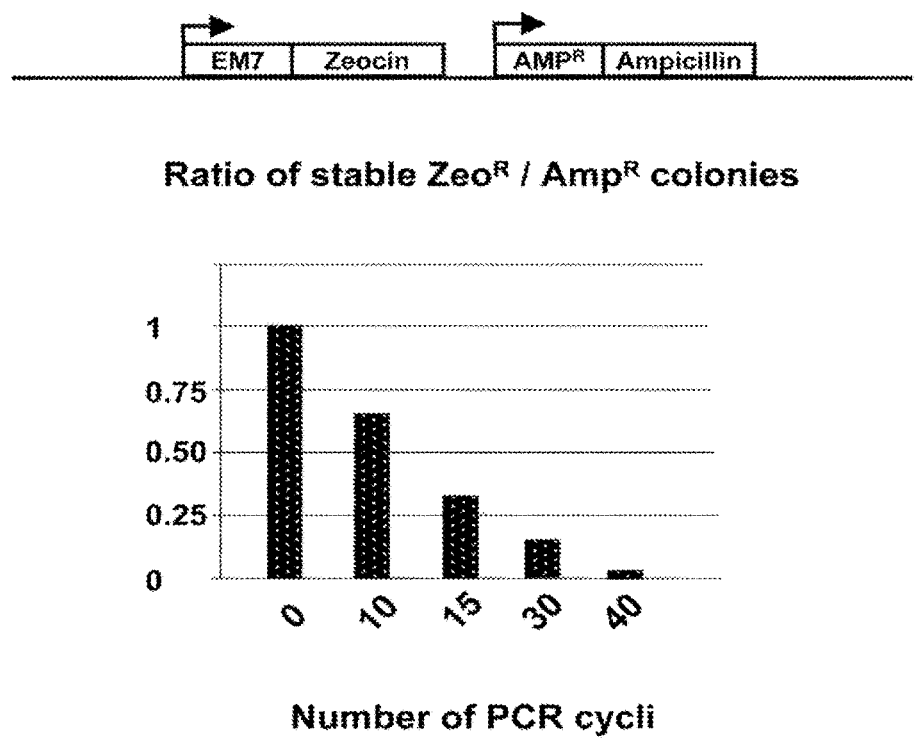
FIG. 4: Error prone PCR strategy to create high stringency zeocin mutants. The bars indicate the ratio of stable zeocin vs ampicilin resistant colonies for increasing the number of PCR cycles performed on the zeocin marker.

FIG. 4 shows that increasing the number of PCR cycles resulted in a decreasing number of Zeocin resistant transformants. This was signified by the decreasing ratio of Ampicillin resistant transformants that are still also Zeocin resistant. Cloning and subsequent transformation of Zeocin fragments that had undergone 40 PCR cycles hardly delivered colonies that were both Ampicillin and Zeocin resistant. We therefore chose to concentrate on Zeocin mutation screens that resulted from 10, 12 and 15 PCR cycles.

Figure 5:
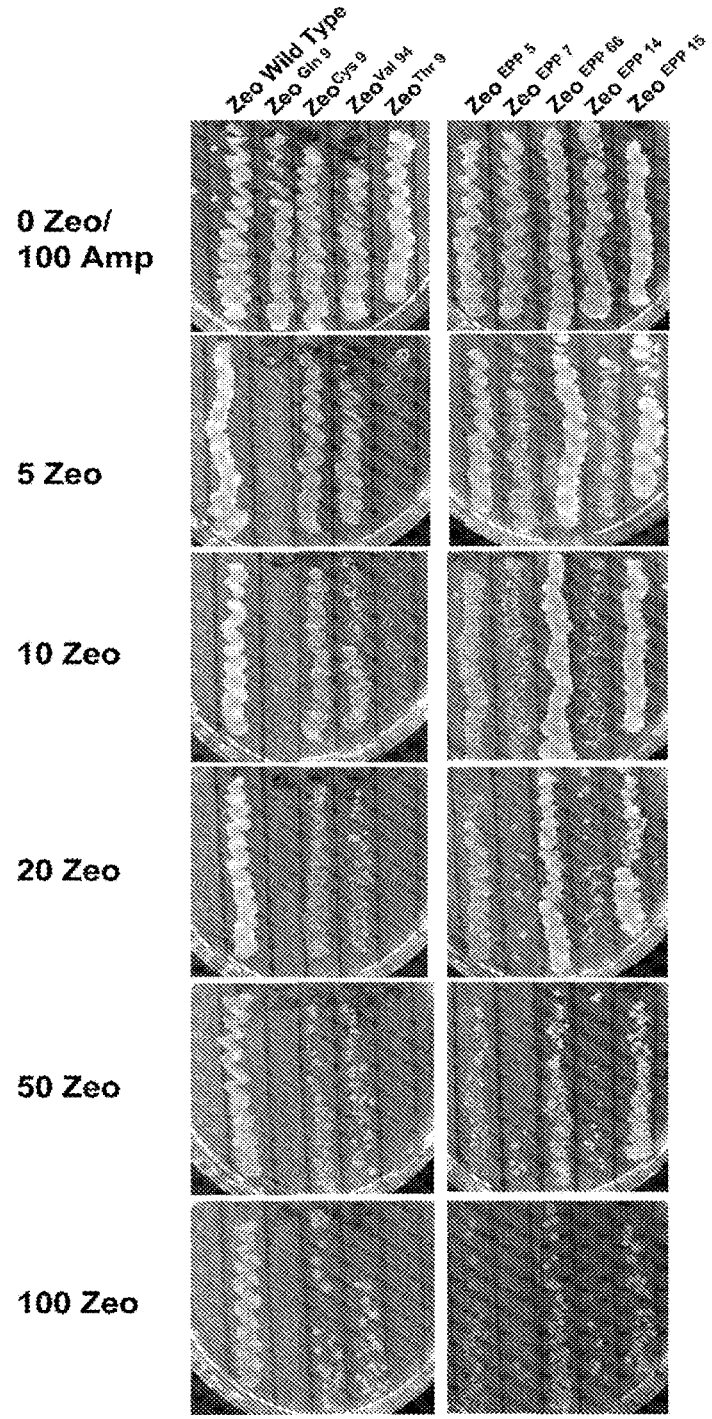
FIG. 5: Zeocin marker mutants as indicated (see also Example 4 and FIG. 6) plated on different zeocin concentrations, ranging from 0 to 100 µg zeocin/ml.

A number of Zeocin marker mutants were plated on different Zeocin concentrations, ranging from 0 to 100 µg/ml Zeocin, as indicated in FIG. 5. Note that all constructs containing a mutated Zeocin marker still grew efficiently on ampicillin alone (top panel). Several control Zeocin marker genes were included in this comparison. These encompassed the wild type Zeocin protein, as well as described mutations at amino acid position 9, in which a proline was changed to glutamine, cystein and threonine (FIG. 5). Also a Zeocin mutant in which the methionine at position 94 was changed to valine was tested (FIG. 5). These Zeocin mutants were selected to allow a comparison between the selection stringencies that resulted from the introduction of these mutations. The results show that the Zeo$^{cys9}$ mutation was relatively mild, since the transformed bacteria still showed significant growth on 100 µg/ml Zeocin. On the other hand, the glutamine 9 mutation was very severe, resulting in no growth of the bacteria at the lowest, 5 µg/ml Zeocin concentration. The other mutations fell in between these extremes. In the right column of FIG. 5 novel Zeocin mutants are shown, described as Zeocin EPP, which stands for Error Prone PCR. These mutants were affected by increasing Zeocin concentrations, much in the range of the His9 and Val94 mutations. In FIG. 6 the amino acid positions of several EPP Zeocin mutations are shown. For instance, the EPP 66, 7 and 14 mutants harbored one, two and three mutations respectively, at different amino acid positions.

5. Example 5: Error Prone PCR Created Zeocin Mutants Confer Different Selection Stringencies In example 4 we introduced mutations in the Zeocin coding region, which resulted in the creation of Zeocin marker proteins that have different abilities to grow on a range of Zeocin concentration, when tested in E. coli. Next we tested whether these Zeocin mutants could be used as high stringency Zeocin selection marker in mammalian CHO-DG44 cells.

5.1 Results

Figure 7:
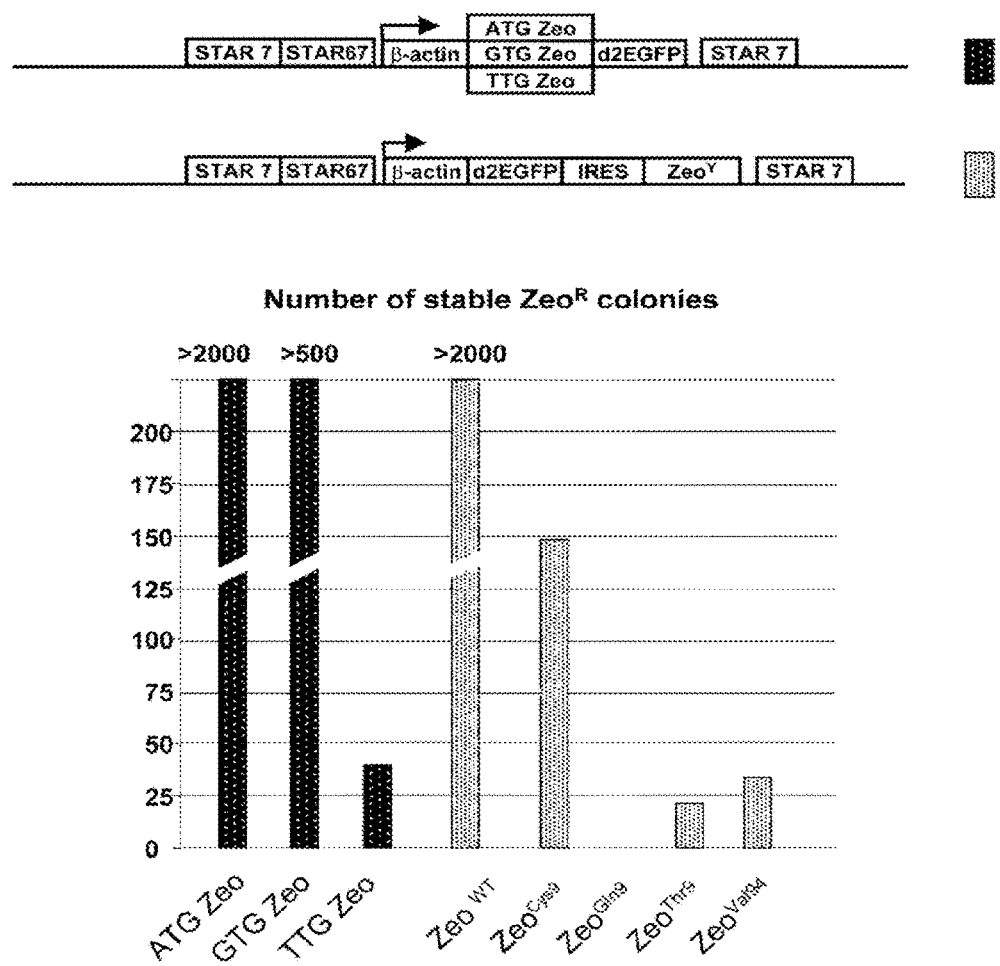
FIG. 7: Colony formation by zeocin mutations. Zeocin mutants as indicated were cloned in an expression cassette, encompassing the human β-actin promoter that drove the d2EGFP gene, followed by an IRES sequence and the Zeocin EPP mutants. STAR 7 and 67 elements flanked the expression cassettes. In the same experiment, known Zeocin selection markers (see FIG. 2) were included for comparison. The various constructs are schematically depicted and the bars indicate the number of stably transfected zeocin resistant colonies obtained with the constructs as indicated.

The Zeocin EPP mutants were cloned in an expression cassette, encompassing the human β-actin promoter that drove the d2EGFP gene, followed by an IRES sequence and the Zeocin EPP mutants. STAR 7 and 67 elements flanked the expression cassettes, as shown in FIG. 7. In the same experiment, a number of STAR-Select constructs were included to provide a comparison. For instance, the ATG/GTG/TTG Zeo configurations induced >2000, >500 and 38 colonies respectively. Selection was done with 400 µg/ml Zeocin in the culture medium. The decreasing numbers of formed colonies signify the increasing selection stringencies conferred by the ATG, GTG and TTG translation initiation codons. In comparison, the wild type Zeocin gene placed downstream of the IRES sequence also resulted in the induction of >2000 colonies. In contrast, the Zeo$^{Gln9}$ mutant allowed no colonies to be formed, indicating that this mutation creates a Zeocin marker protein that is functionally so impaired that it cannot function anymore as selection marker. This closely reflects the result with this mutation in E. coli, as described in Example 4. Introducing the Cys9, Thr9 and Val94 mutations resulted in Zeocin marker proteins that respectively induced 150, 24 and 35 stably transfected CHO-DG44 colonies. Both the Thr9 and Val94 mutations in the d2EGFP-IRES-Zeo configuration apparently approach the same selection stringency as the TTG Zeo-d2EGFP configuration in the STAR-Select system.

Figure 8:
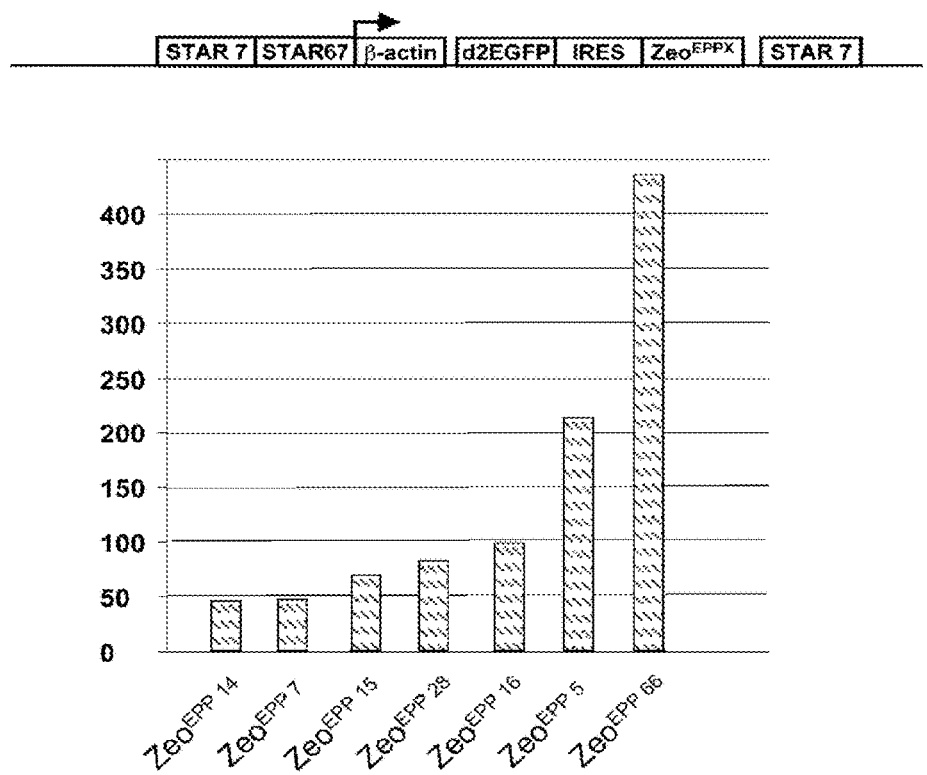
FIG. 8: Colony formation by the zeocin EPP (Error Prone PCR) mutants. The zeocin EPP14, EPP7, EPP15, EPP28, EPP16, EPP5 and EPP66 mutants, tested in the same experiment as described FIG. 7, were able to induce 37, 34, 66, 73, 97, 215 and 435 stably transfected CHO-DG44 colonies, respectively. The constructs are schematically depicted and the bars indicate the number of stably transfected zeocin resistant colonies obtained with the constructs as indicated.

Several EPP Zeocin mutants that we created and that showed impaired functional activity in E. coli (FIG. 5), were cloned downstream of the IRES sequence. In the same experiment, as shown in FIG. 7, the Zeocin EPP14, EPP7, EPP15, EPP28, EPP16, EPP5 and EPP66 mutants were able to induce 37, 34, 66, 73, 97, 215 and 435 stably transfected CHO-DG44 colonies respectively (FIG. 8). These numbers indicate that these mutations create Zeocin mutants with similar selection stringency as the Cys9 and Val94 mutations (compare FIG. 7).

In the same experiment, we also measured the expression levels of the d2EGFP protein in the expression cassettes, as indicated by the mean fluorescence in the stably transfected CHO-DG44 colonies. As shown in FIG. 9, different Zeocin mutants gave rise to colonies with different average d2EGFP fluorescence values. As expected, the TTG Zeo STAR-Select configuration gave high d2EGFP values (average 1402). The ATG Zeo (control), Cys9, Thr9 and Val94 mutations gave average d2EGFP values of 57, 570, 3385 and 2280, respectively. These results show that the Cys9 induced a less stringent mutation than the TTG Zeo in the STAR-Select configuration, whereas the Thr9 and Val94 induced a higher Zeocin selection stringency than TTG Zeo in the STAR-Select configuration.

Figure 10:
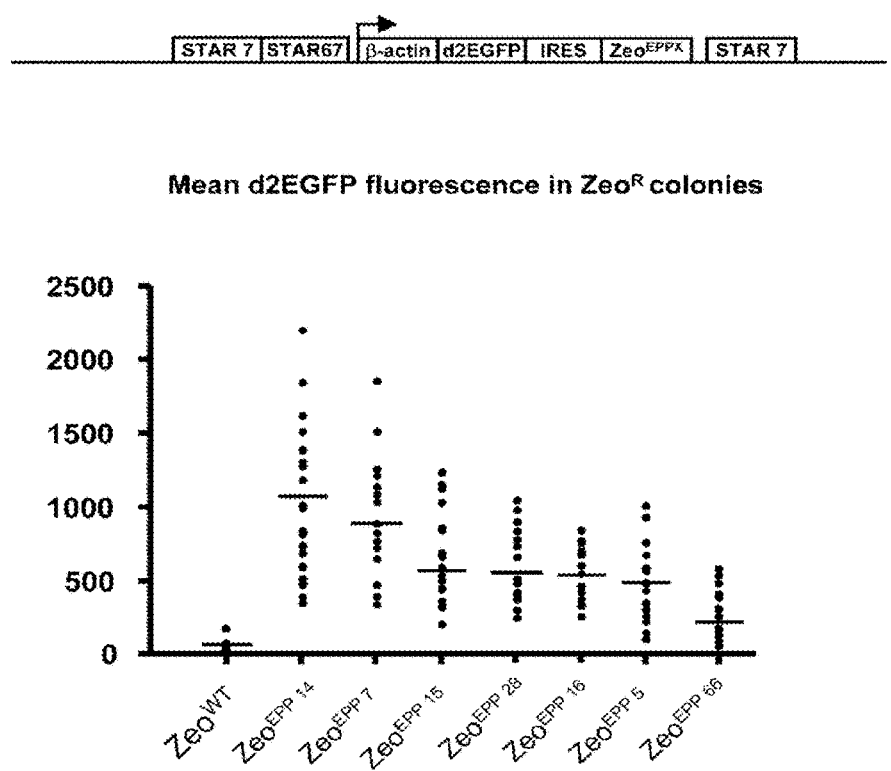
FIG. 10: Influence of EPP zeocin mutations on reporter protein expression levels. EPP zeocin mutants as indicated were placed behind an internal ribosome entry site (IRES). The EPP zeocin genes and IRES were placed downstream of the d2EGFP reporter gene, to determine the expression levels after selecting stably transfected clones. As controls the wild type zeocin gene (Zeo WT) behind the IRES sequence was used. The constructs are schematically depicted and the mean d2GFP expression levels in the zeocine resistant colonies are indicated (bars).

In comparison, the Zeocin EPP14, EPP7, EPP15, EPP28, EPP16, EPP5 and EPP66 mutants induced an average d2EGFP value in CHO-DG44 colonies of 1219, 850, 525, 503, 631, 498 and 187 respectively (FIG. 10). The averages induced by the EPP 14, 7 and 15 are higher than observed with the Cys9 mutation (570), but significantly lower than with the Thr9 and Val94 mutations (FIG. 9). Instead, they are more in the range of the TTG Zeo STAR-Select configuration. This indicates that the EPP14, 7 and 15 mutations induce selection stringency in the Zeocin selection marker protein that lies between the selection stringency induced by the Cys 9 (570) and Val94 (2280) mutations.

These results show that Error Prone PCR can be used to create Zeocin marker proteins that convey high selection stringency in mammalian cells. The EPP Zeocin mutants convey similar selection stringencies as the previously described TTG Zeo STAR-Select configuration.

6. Example 6: Small Peptides, Combined with Error Prone PCR Created Zeocin Mutants Confer Higher Selection Stringencies We next tested whether placing a small peptide upstream of the ATG of the Zeocin EPP mutants has an influence on the selection stringencies of these mutants. This provides more flexibility to the system. It may, for instance, be useful to lower the amount of Zeocin mutant protein that has to be made by a cell. When a relatively severe EPP mutation is introduced in the Zeocin coding region, probably very high amounts of mutant Zeocin protein have to be made by the cell. After all, the hampered activity of the Zeocin EPP mutant protein originates from the functionality of the Zeocin protein itself. It may be less favorable to produce such high amounts of selection marker though, since this can put a metabolic burden on the cell. Alternatively, the high amount of mutated selection (e.g. Zeocin) protein might be toxic in itself, which could also not be advantageous to the cell. Either way, this could result in for instance reduced cell growth. Using a relatively mild EPP-induced mutein of the selection protein (e.g Zeocin) could circumvent these disadvantages. This warrants that less of the mutant selection protein (e.g Zeocin) has to be made, but it also will lower the selection stringency. Combining a mild mutant of the selection protein (e.g. Zeocin) with a small peptide can be circumvented these drawbacks. This addition requires higher levels of mRNA encoding the selection protein to provide sufficient functional protein for selection and may therefore provide a more favorable condition.

6.1 Results

Figure 11:
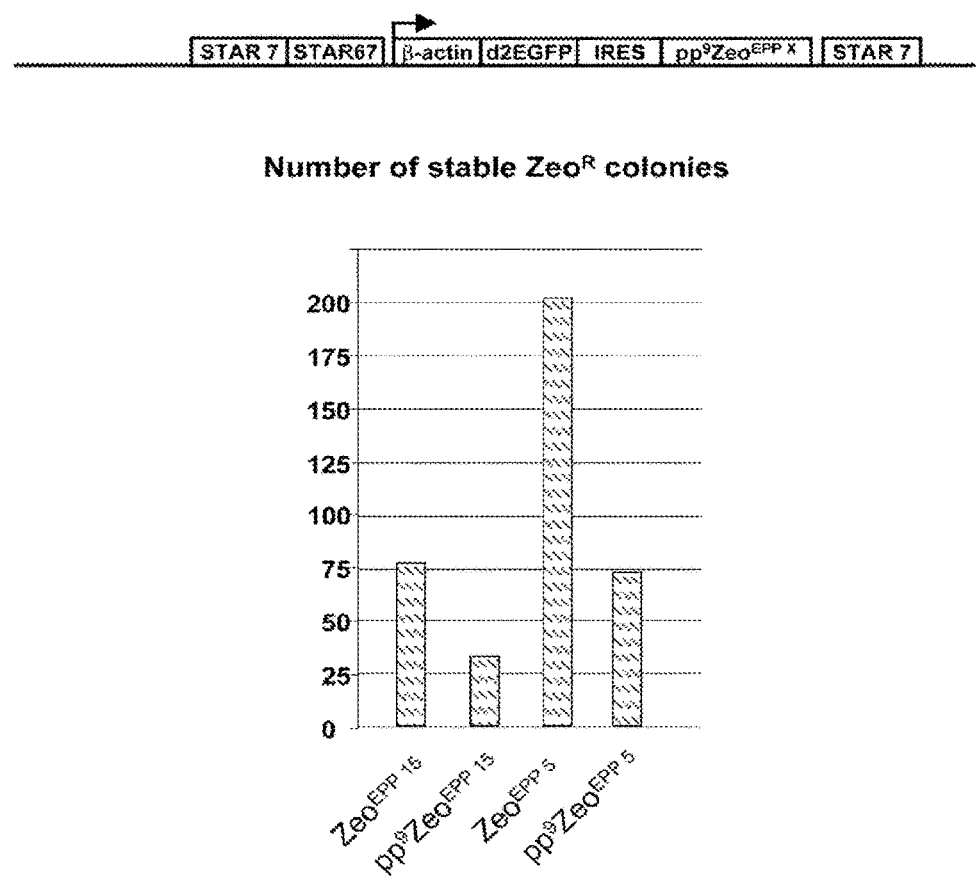
FIG. 11: Influence of the combination of zeocin mutations with the use of small peptides on colony formation. Zeocin mutants EEP5 and 15 with or without small peptide $pp^9$ were placed behind an internal ribosome entry site (IRES). The zeocin genes and IRES were placed downstream of the d2EGFP reporter gene. The constructs are schematically depicted and the bars indicate the number of stably transfected zeocin resistant colonies obtained with the constructs as indicated.

A small peptide, 9 amino acids long was placed upstream of the Zeo$^{EPP15}$ and Zeo$^{EPP5}$ mutants. These new Zeocin configurations were placed downstream of the IRES sequence and d2EGFP gene (FIG. 11). Introducing the small peptides upstream of the ATG of the Zeocin EPP15 and EPP5 proteins resulted in a progressive decrease in the number of stably transfected CHO-DG44 colonies (FIG. 11). In either case, the number of stably transfected cloned decreased by more than 50% when the pp9 was added to the Zeo mutant (FIG. 11).

Figure 12:
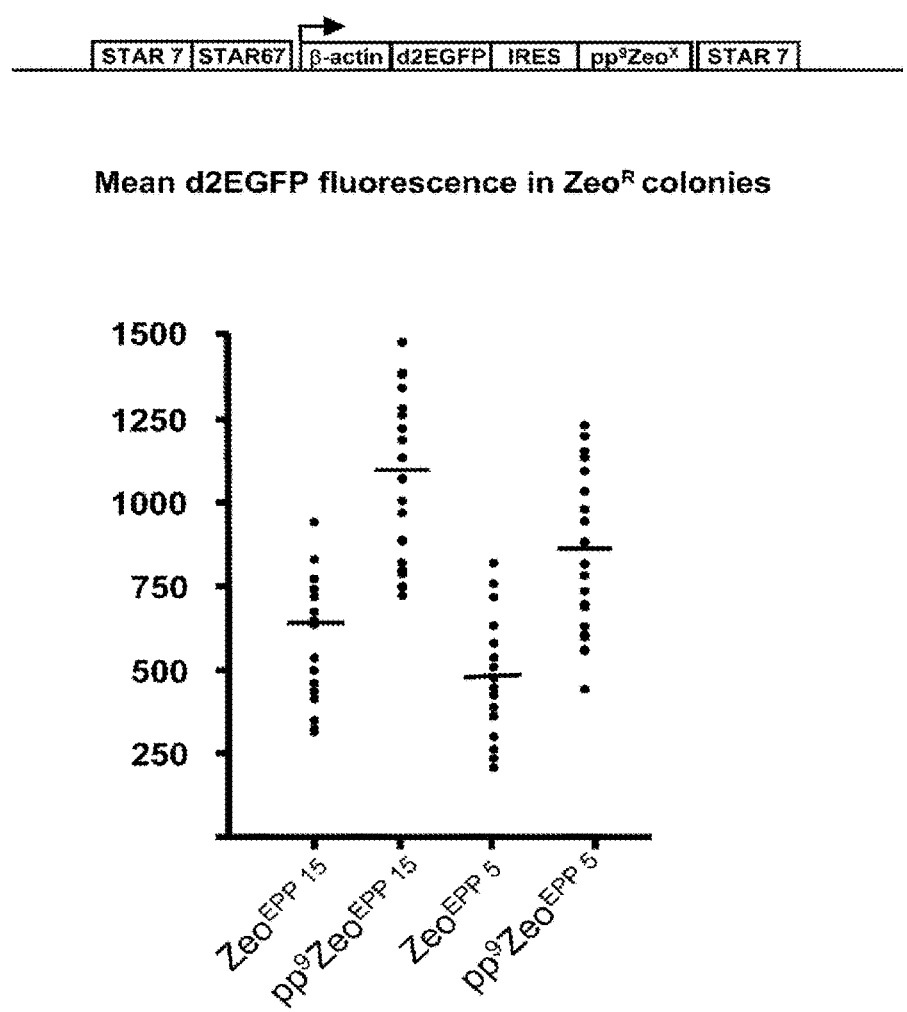
FIG. 12: Influence of the combination of zeocin mutations with the use of small peptides on reporter protein expression levels. Zeocin mutants EEP5 and 15 with or without small peptide $pp^9$ were placed behind an internal ribosome entry site (IRES). The zeocin genes and IRES were placed downstream of the d2EGFP reporter gene. The constructs are schematically depicted and the mean d2GFP expression levels in the zeocine resistant colonies are indicated (bars).

We also measured the expression levels of the d2EGFP protein, as indicated by the mean fluorescence in the stably transfected CHO-DG44 colonies. As shown in FIG. 12, the additional pp9 in the Zeo$^{EPP15}$ mutant induced an average d2EGFP fluorescence value of 1109, as compared to the average 648 with the Zeo$^{EPP15}$ mutant alone (FIG. 12). Similarly, the additional pp9 in the Zeo$^{EPP5}$ mutant induced an average d2EGFP fluorescence value of 863, as compared to the average 481 with the Zeo$^{EPP5}$ mutant alone (FIG. 12).

Figure 13:
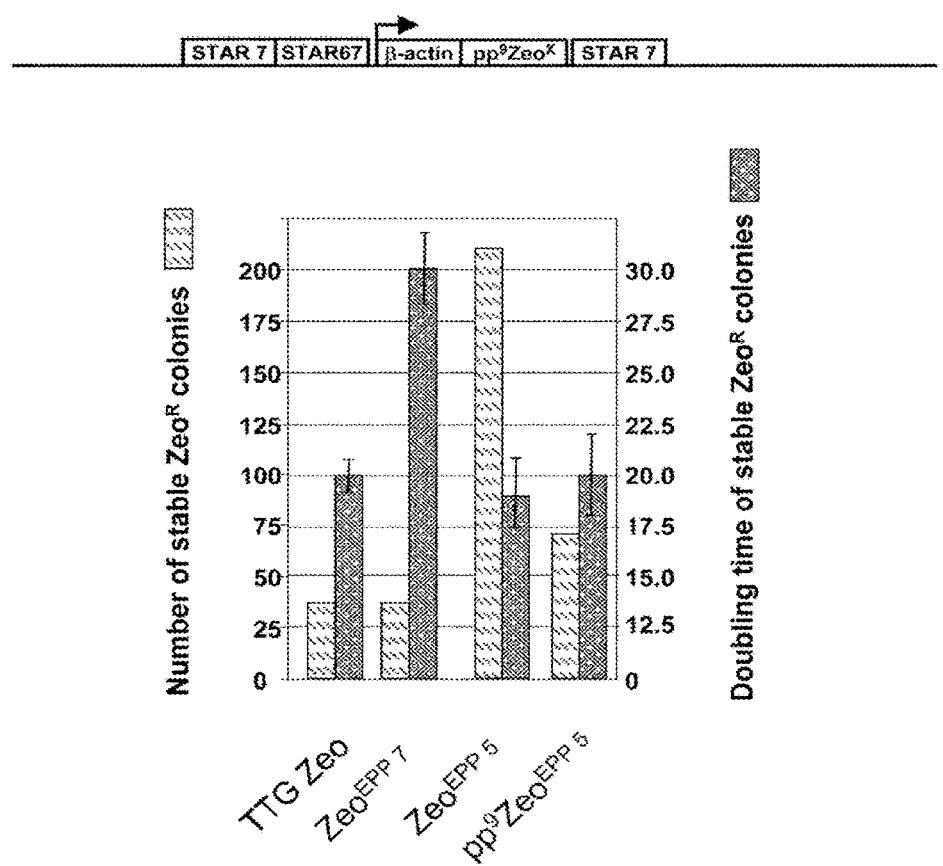
FIG. 13: Influence of the combination of zeocin mutations with the use of small peptides on selection stringency and cell growth. Selection stringencies and growth rates of the colonies that were established with zeocin mutants EPP 7 and EPP 5 with or without small peptide $pp^9$ were compared with those of the TTG Zeo mutant. The constructs are schematically depicted. The left hand bars indicate the number of stable zeocin resistant colonies and the right hand bars indicate the doubling time of the stable zeocin resistant colonies obtained with the various constructs.

We also compared the growth rates of the colonies that were established with the different selection marker configurations (FIG. 13). The selection stringency of the TTG Zeo mutant was very similar to the selection stringency of the Zeo$^{EPP7}$ mutant, as signified by the numbers of stable colonies (34 versus 36, respectively). However, the colonies established by the Zeo$^{EPP7}$ mutant grew significantly slower than the TTG Zeo induced colonies (average 30 versus 20 hours, respectively) (FIG. 13). In comparison, the selection stringency of the Zeo$^{EPP5}$ mutant was low (200 colonies), but the selection stringency was increased by addition of the pp9 small peptide (65 colonies, see also FIG. 11). The average growth rate of the colonies established with the Zeo$^{EPP5}$ mutant was 20 hours, comparable with the TTG Zeo growth rate. Importantly, addition of the pp9 small peptide to the Zeo$^{EPP5}$ mutant did increase the selection stringency, but the average growth rate remained 20 hours. These results show that combining the small peptide approach with Error Prone PCR created Zeocin mutants results in the creation of progressively higher selection stringencies of the Zeocin marker protein. Importantly, combining a small peptide and a relatively mild EPP-created Zeocin mutant results in an increase of selection stringency, without affecting the growth rate of a cell. Such configuration clearly has an advantage over a very stringent EPP-created Zeocin mutant that is not combined with a small peptide.

7. Example 7: The Influence of Spacers, Placed Between the Small Peptides and the ATG of the Gene of Interest In the previous examples, we have placed the small peptide immediately upstream of the Zeocin resistance gene. That is, only 9 bp that provided convenient restriction sites were present between the stop codon of the small peptide and the ATG of the Zeocin gene. It is, however, possible that placing a 'spacer' sequence between the small peptide and the Zeocin gene might influence the selection stringency of the system. We tested this directly by placing a subsequently longer DNA stretch between the stop codon of the small peptide and the ATG of the Zeocin resistance gene. This synthetic spacer sequence was chosen as such that it contained no ATG sequences, in order to avoid unwanted, premature translation initiation at this point.

7.1 Results

Figure 14:
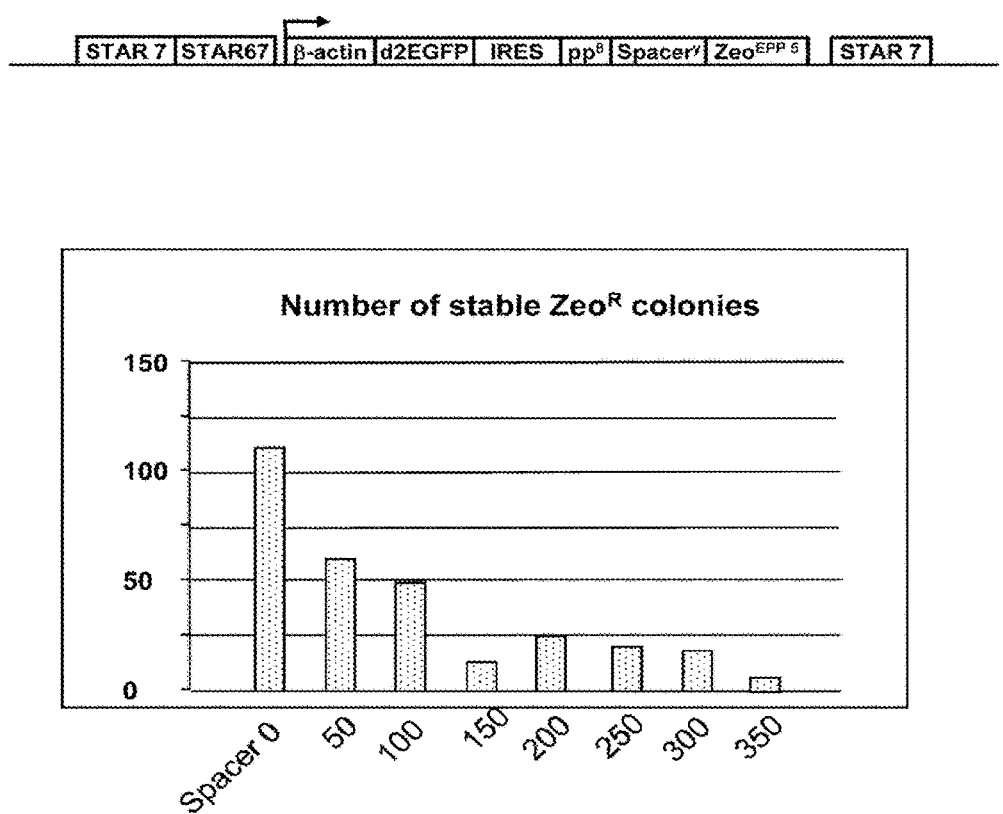
FIG. 14: Influence of an 'spacer' sequence between the stop codon of the small peptide and the start codon of the selectable marker on number stable colonies. Spacer sequences of increasing length, as indicated were inserted between the $pp^8$ open reading frame and the start codon of the Zeocin coding sequence in the DNA constructs as depicted. The number of stable Zeocin-resistant colonies was determined for the constructs with varying spacer lengths.
Figure 15:
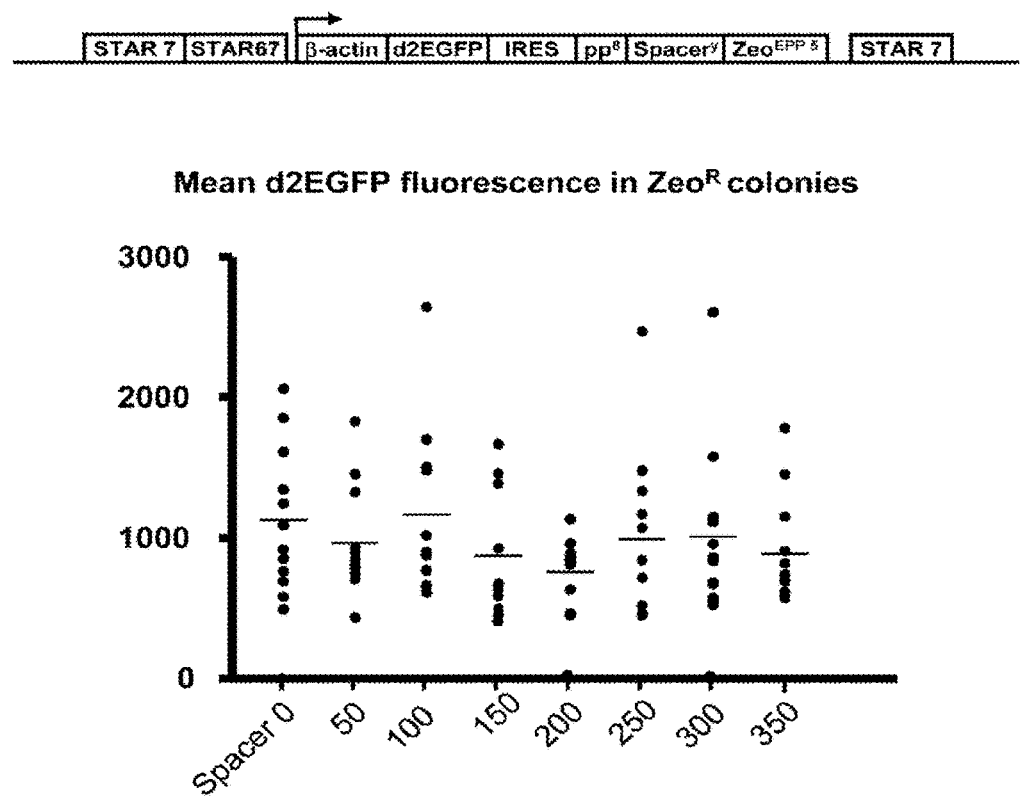
FIG. 15: Influence of an 'spacer' sequence between the stop codon of the small peptide and the start codon of the gene of interest on expression levels. Spacer sequences of increasing length, as indicated were inserted between the $pp^8$ open reading frame and the start codon of the Zeocin coding sequence in the DNA constructs as depicted. The mean d2EGFP fluorescence in Zeocin-resistant colonies obtained with the constructs with varying spacer lengths was determined.

A spacer DNA stretch was synthesized in a way that it allowed easy cloning of parts of this sequence. Constructs were made in which the small peptide was separated by 50, 100, 150, 200, 250, 300 and 350 bp of the spacer sequence presented below (SEQ ID NO: 32; FIG. 14). As small peptide 8 amino acids of the luciferase protein were used (pp8) and as Zeocin marker, the EEP5 Zeocin mutant was used (FIG. 14). As comparison, a construct was used in which no spacer sequence was present (spacer 0, FIG. 14), in fact the configuration that was used in the previous examples. In all cases STARs 7 and 67 were used to flank the construct. The plasmids were transfected to CHO-DG44 cells and the induced stable colonies were counted. As shown in FIG. 14, the highest number of colonies was formed when no spacer sequence was present. Even the inclusion of 50 bp between the small peptide and the ATG of the Zeocin gene resulted in a decline of the number of colonies. When the d2EGFP expression levels were analyzed in these colonies, no major differences were found between the different constructs (FIG. 15). This result indicates that inclusion of a spacer sequence between the small peptide and the resistance gene does not result in an advantage for the selection system, neither in terms of induced colony numbers nor in protein expression levels.

```
Spacer sequence
                                          (SEQ ID NO: 32)
TAAggatccctcatcatcaactcctctcgatctactcgtctccctcaag gtatcgctctccctcaaagaactccctccgtcagatcctcgcatcccag agatcctatctagatcctatatcatccaaaaaatcatcatcatcgatcc tcaaatcgatcaccagggatctcagtcgatctacatcttcgtcacatct catctacctcccggttttcatcaatatcatcttctaccagagtccttcg aaagggacaagacaatcccactcatcatcaactcctctcgatctactcg tctccctcaaggtatcgctctccctcaaagaactccctccgtcagatcc tcgcatcccagagatcctatctagatccaccATG
```

8. Example 8: The Use of Small Peptide to Create a Selection System Using the dhfr Protein as Selection Marker In all previous examples, the Zeocin resistance gene was used as selection marker. In this example we tested whether another selection marker could also be used as 'maintenance' and/or selection marker. We chose the dhfr protein as selection marker.

The dhfr protein is essential for cell survival, since it is an enzyme that metabolizes one or more essential steps in a metabolic pathway. With essential is meant that the cell is not able to synthesize specific metabolic building blocks itself, implying that these building blocks have to be present in the culture medium in order to allow the cell to survive. The dhfr protein is an enzyme in the folate pathway that converts folate into 5,6,7,8 tetrahydrofolate, a methyl group shuttle required for the synthesis of purines (Hypoxanthine), thymidylic acid (Thymidine), and certain amino acids (Glycine). CHO-DG44 cells lack the dhfr gene and CHO-DG44 cells therefore need glycine, hypoxanthine and thymidine in the culture medium to survive. If, however, the dhfr gene is present on the expression cassette, the cell can convert folate into 5,6,7,8 tetrahydrofolate, provided that the end-products glycine, hypoxanthine and thymidine (GHT) are absent from the culture medium (often only hypoxanthine and thymidine (HT) are removed). Furthermore, the non-toxic precursor folate needs to be present in order for the cell to be able to synthesize the 5,6,7,8 tetrahydrofolate (Urlaub et al, 1980, Proc Natl Acad Sci USA, 77: 4216-4220). This principle has been used for many years as selection methodology to create stably transfected mammalian cell lines.

8.1 Results

Figure 16A:
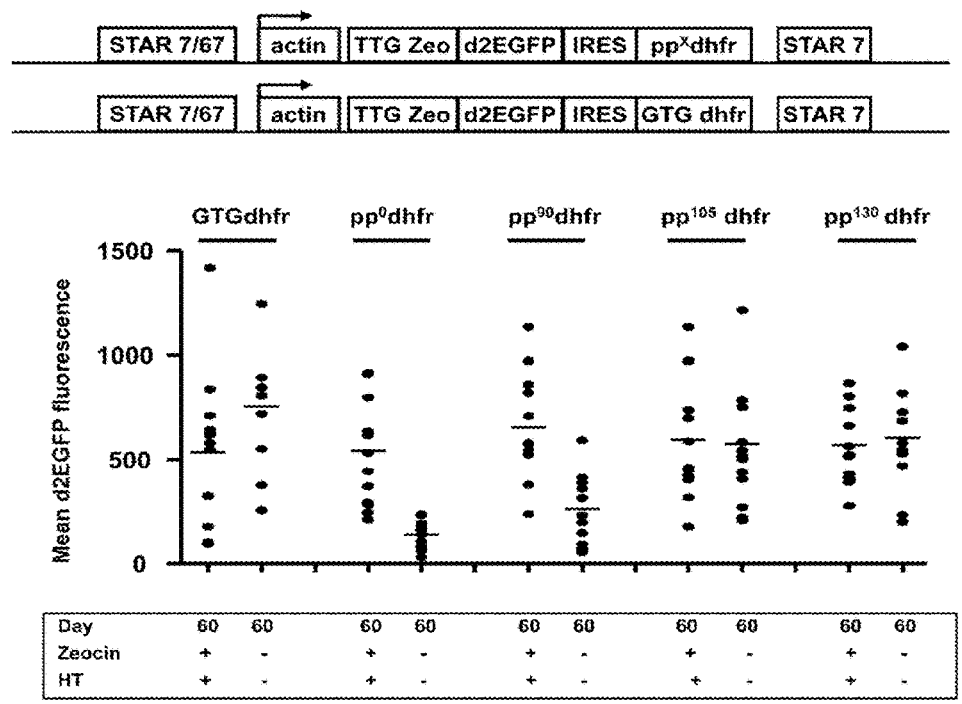
FIGS. 16A and 16B: The use of small peptides to create a 'maintenance' system using dhfr as marker. Constructs as depicted were made wherein the TTG Zeo marker was used for initial selection. Downstream of the d2EGFP reporter gene, an IRES sequence and a specific dhfr gene was placed, which dhfr gene was either the ATG (or $pp^0$) dhfr, or the ATG dhfr gene proceeded by a $pp^{90}$ $pp^{105}$ or $pp^{130}$ small peptide. In a control construct the GTG dhfr gene was placed downstream of the IRES sequence. In all cases STARs 7 and 67 were used to flank the construct. The constructs were transfected to CHO-DG44 cells and mean d2EGFP fluorescence in FIG. 16A and average daily doubling times in FIG. 16B were determined after 60 days of culture in the presence of Zeocin and HT supplement (=Zeocin selection) and in the absence of Zeocin and HT supplement (=DHFR selection).

We made constructs in which the TTG Zeo was used for initial selection (FIG. 16). Downstream of the d2EGFP reporter gene, we placed an IRES sequence and a specific dhfr gene. This dhfr gene was either the ATG (or pp0) dhfr, or the ATG dhfr gene proceeded by a pp90, pp105 or pp130 small peptide (FIG. 16). In a control construct we placed the GTG dhfr gene downstream of the IRES sequence. In all cases STARs 7 and 67 were used to flank the construct. The constructs were transfected to CHO-DG44 cells. As expected similar numbers of colonies emerged, since selection took pace through the TTG Zeo protein. After an initial d2EGFP expression measurement, clones were split and cultured in the presence of Zeocin and HT supplement. As shown in FIG. 16A, the d2EGFP expression values remained rather similar over a time period of 60 days. However, when both Zeocin and HT supplement were removed from the culture medium, a different picture emerged. In case of the pp0 dhfr downstream of the IRES sequence, the d2EGFP expression levels dropped severely. Also with the construct harboring the pp90 dhfr gene, d2EGFP expression values declined. Only when a pp105 or pp130 was included, the d2EGFP expression levels remained constant (FIG. 16A). In case of the GTG dhfr gene, the d2EGFP expression levels increased slightly. We interpret these results as such that in case of the pp0 and pp90 dhfr too much functional dhfr protein is made to create a stringent selection system. As a result, d2EGFP expression levels drop. Only when more stringent small peptides, pp105 and pp130 are used, or the GTG dhfr variant, the selection system becomes stringent enough to allow constant d2EGFP expression levels over a prolonged period of time. Since the pp105 and pp130 small peptide are rather long, it might be more efficient to modify the dhfr protein itself, to create a more stringent dhfr protein. Combining such a mutated dhfr protein with a shorter small peptide might create a more stringent selection system. This would follow the error prone PCR (EPP) Zeocin mutant approach as described in the previous examples.

Figure 16B:
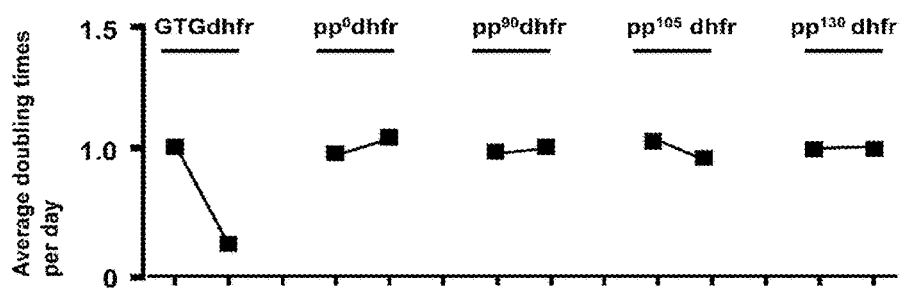

We also compared growth rates of the colonies that were analyzed. As shown in FIG. 16B, no major impact on growth rates was observed in case of the pp90, 105 and 130. In contrast, when the GTG dhfr protein was used, growth rates of the cells declined dramatically (FIG. 16B). Therefore, whereas the d2EGFP expression levels in the GTG dhfr clones increased, the growth rates of the cell declined, making the GTG dhfr rather unusable in this context.

We next tested the possibility to use dhfr protein that is modified with a small peptide directly as selection marker. We removed the Zeocin resistance gene from the constructs, resulting in a d2EGFP reporter gene, followed by an IRES sequence and a modified dhfr gene. These constructs were transfected to CHO-DG44 cells, and grown in the absence of HT supplement. As shown in FIG. 17, inclusion of pp0, 14, 23, 42, 54 and 63 induced >600 stable colonies in CHO-DG44. In contrast, no colonies were formed under identical conditions with the GTG dhfr gene placed downstream of the IRES sequence (FIG. 17). Only in case of pp75, 90, 105 and 130 a decline in the number of induced colonies was observed (FIG. 17). d2EGFP expression levels were only measured in colonies induced by the pp0, 14, 90, 105 and 130 (FIG. 18). D2EGFP expression values were very low in case of the pp0 and pp14. Whereas d2EGFP expression levels increased with pp90, reasonable expression levels were obtained only in case of pp105 and pp130. This is in line with the high number of colonies induced with these modifications, as shown in FIG. 17. This reinforces the idea to employ a modified dhfr protein, in combination with a much shorter small peptide, as we used with the EPP modified Zeo mutants.

Taken together, this example shows that it is possible to use the small peptide approach with a different selection marker than Zeo as selection marker, in this case dhfr. However, the differences in selection stringencies are obvious, the dhfr protein requiring much longer small peptides to create a stringent selection system than the Zeo protein.

Figure 19:
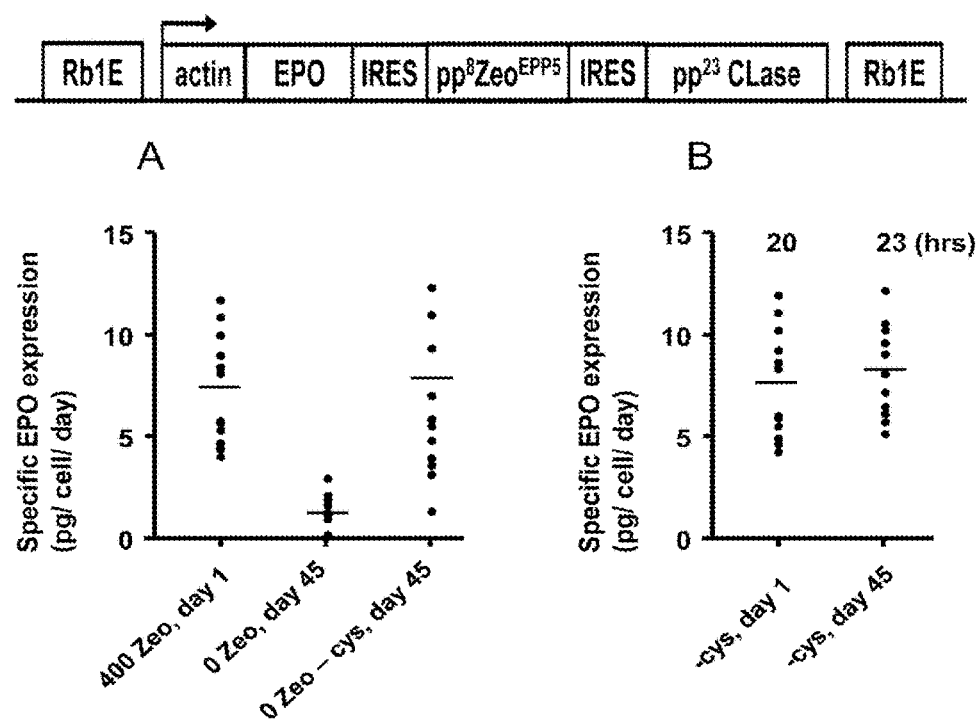
FIG. 19: Induction of high EPO expressing colonies by using the CLase marker. A construct as depicted was constructed comprising a mutant Zeocin protein, coupled to an 8 amino acid long small peptide. This specific Zeocin mutant is called EPP5. This mutant selection marker was placed downstream of the EPO reporter gene, but upstream from the pp23CLase marker. Rb1E elements flanked the entire construct. The construct was transfected to CHO-DG44 cells that were selected and maintained as indicated and described in detail in Example 9. EPO expression levels were determined after 1 day (selection) or 45 days (maintenance).

9. Example 9: CLase as Maintenance and Selection Marker Using EPO as Reporter Protein Here we tested the potential of CLase as maintenance/selection marker by using EPO as a secreted reporter gene.
9.1 Results In these experiments we used a mutant Zeocin protein, coupled to an 8 amino acid long small peptide. This specific Zeocin mutant was created through error prone PCR (EPP) and was called EPP5. This mutant selection marker, referred to as pp8ZeoEPP5 (SEQ ID NO: 33) was placed downstream of the EPO reporter gene, but upstream from the pp23CLase marker (SEQ ID NO: 34) (FIG. 19). Rb1E elements (SEQ ID NO: 36) flanked the entire construct. When initial selection was performed using 400 µg/ml Zeocin in the culture medium an average specific EPO production of 7.6 pg/cell/day was induced in 12 propagated colonies (FIG. 19A). After this initial day 1 measurement, cells were split and left for 45 days with no Zeocin selection pressure, but with L-cysteine/L-cystine in the culture medium, or without Zeocin and without L-cysteine/L-cystine in the culture medium. As shown in FIG. 19A, EPO expression levels dropped to below 1 pg/cell/day when no Zeocin was present. However, without L-cysteine/L-cystine in the culture medium the EPO specific expression levels remained constant (7.6 pg/cell/day) (FIG. 19A). This demonstrates the ability of pp23CLase to act as 'maintenance' marker in CHO-DG44 cells.

We also attempted direct selection with culture medium from which L-cysteine/L-cystine was omitted. We used the same constructs in this experiment. As shown in FIG. 19B, similar EPO levels as with pp8ZeoEPP5 were obtained, either at day 1 or day 45. When the growth of these cells was examined, we found that the average doubling time was 20 and 23 hours at day 1 and day 45 respectively. This is close to the grow rate of wild type CHO-DG44. We conclude that also with EPO as reporter protein the pp23CLase provides enough selection stringency for high protein expression levels, while retaining the ability of the cells to grow.

Figure 20:
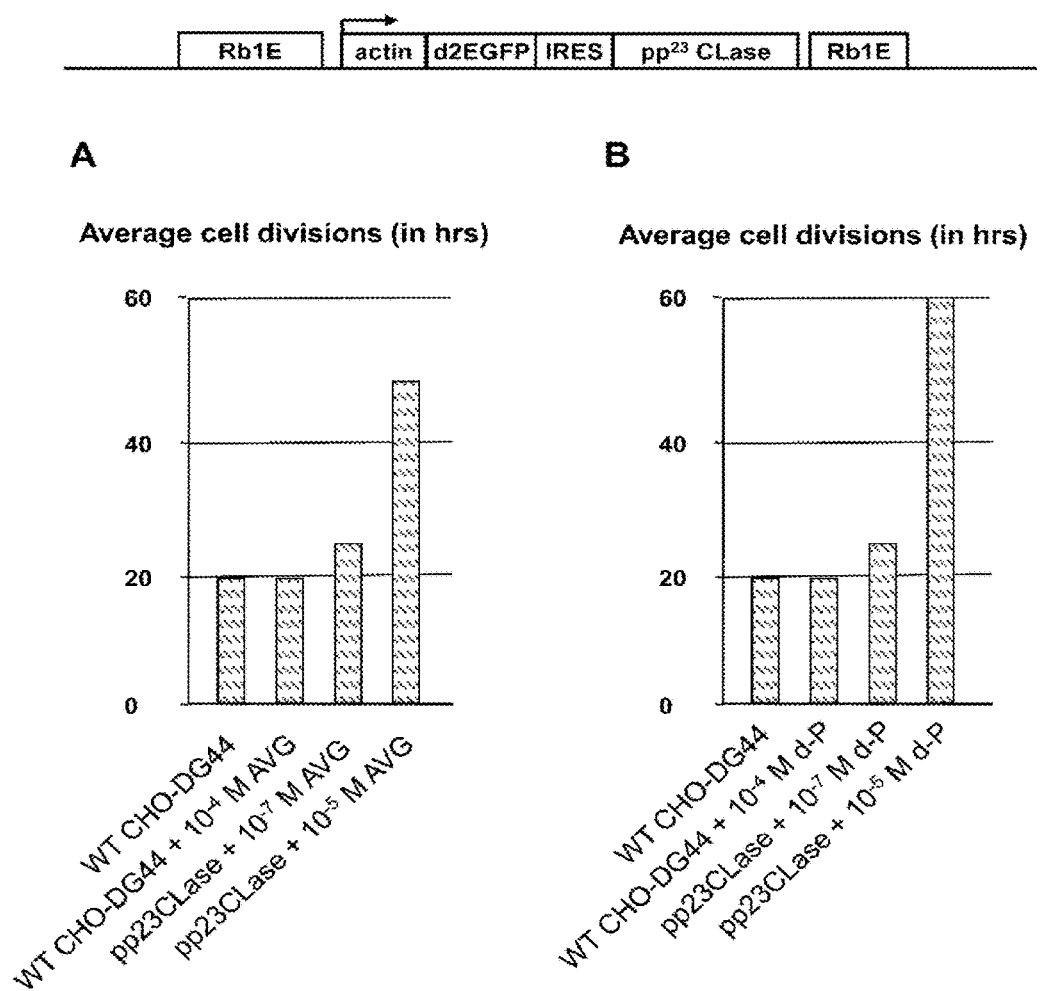
FIG. 20: Identification of CLase inhibitors. A pp23 CLase construct as depicted was transfected to CHO-DG44 cells and stable transformants were selected. Next CLase inhibitors aminoethoxyvinylglycine (AVG, A) and d-propargylglycine (d-P, B) were added in concentrations as indicated and cell division times in hours were determined for concentrations of inhibitors as indicated.

10. Example 10: Aminoethoxyvinylglycine (AVG) and d-Propargylglycine (d-P) are Inhibitors of the CLase Enzyme In the above described experiments we used CHO-DG44 as cell line. This cell line is known to be auxotrophic for the CLase enzyme. Cell lines of human or mouse origin are, however, not auxotrophic for the CLase enzyme. The dhfr and glutathione synthase (GS) selection marker are, however, also often used in cells that do contain a functional corresponding enzyme. This requires that the endogenous enzyme activity must be inhibited, in case of dhfr and GS by methotrexate and methionine sulfoximine (MSX) respectively. We tested two chemicals that have been found to inhibit CLase in vitro. Purified CLase enzyme has been used for enzyme kinetics and it was found that Aminoethoxyvinylglycine (AVG) was a reversible inhibitor and that d-Propargylglycine (d-P) was an irreversible inhibitor of CLase (Steegborn et al., 1999, J. Biol. Chem. 274: 12675-12684). AVG is a substance that is widely used in the food industry, as an inhibitor of ethylene that is responsible for ripening processes. This non-toxic characteristic makes AVG a suitable substance for use as CLase inhibitor. We tested AVG and d-P for their potential use as inhibitor of CLase in cell lines.
10.1 Results We first tested the use of AVG and d-P in CHO-DG44 cells. We added $10^{-10}$ to $10^{-4}$ M AVG and $10^{-8}$ to $10^{-4}$ M d-P to wild type CHO-DG44 cells and determined the division time of the cells. We noted no effect on cell growth or otherwise even with the highest concentrations of $10^{-4}$ M AVG (FIG. 20A) or $10^{-4}$ M d-P (FIG. 20B). This is not surprising since CHO-DG44 do not possess a functional CLase gene. The result is important though, since it also demonstrates the non-toxicity of the substances. We next tested AVG and d-P on cells that were stably transfected with the pp23 CLase construct and that grew in medium devoid of L-cysteine/L-cystine and in the presence of the precursor L-glutathionine. These cells are therefore dependent on the activity of the transfected CLase protein for their survival. When $10^{-7}$ to $10^{-5}$ M AVG (FIG. 20A) or $10^{-7}$ to $10^{-5}$ M d-P (FIG. 20B) was added to these cells, we observed a rapid effect on cell growth. At low concentrations ($10^{-7}$ M), cells still had a division time of average 23 hours in case of AVG (FIG. 20A) or 25 hours in case of d-P (FIG. 20B). When higher ($10^{-5}$ M) concentrations of AVG or d-P were used, cells had severe grow problems, as indicated by cell divisions of 50 (AVG) and >60 (d-P) hrs (FIG. 20). This result indicates that both substances are very effective inhibitors of CLase.

Figure 21:
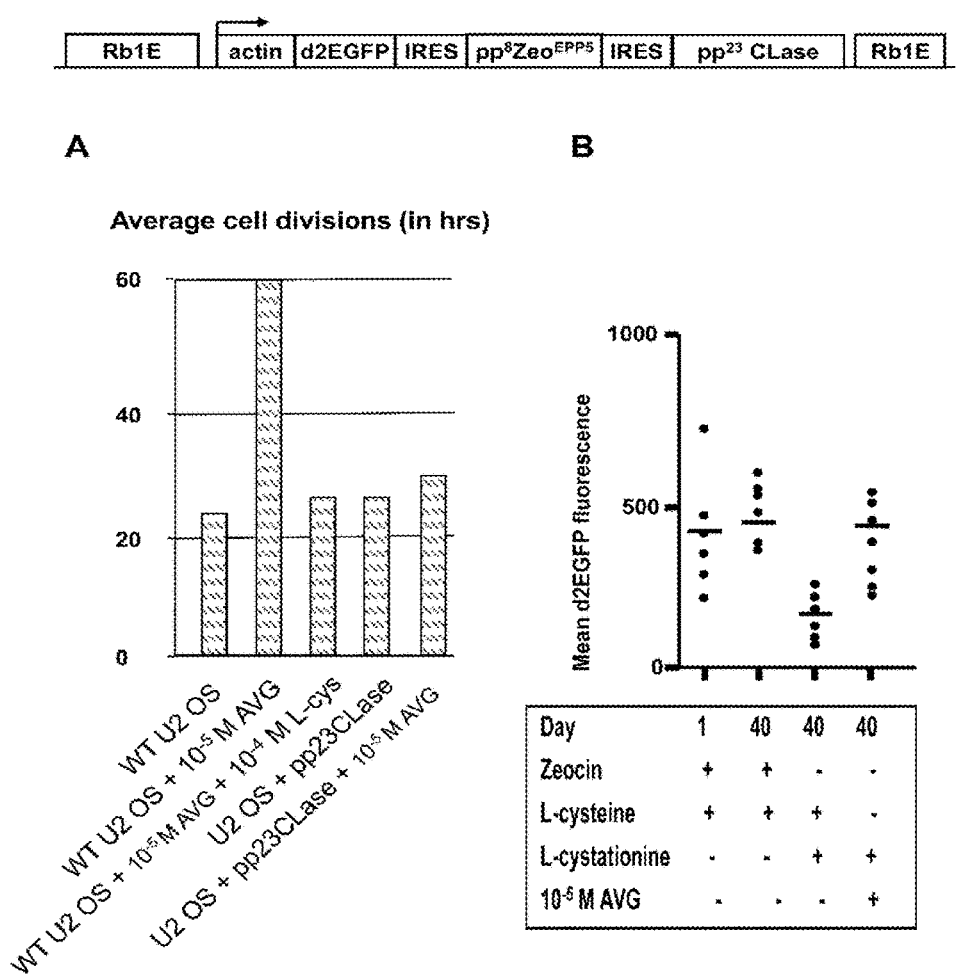
FIG. 21: The use of aminoethoxyvinylglycine as a CLase inhibitor in the human U2 OS cell line.

Next, we tested the usefulness of the AVG inhibitor in the human cell line U2 OS. When we added $10^{-5}$ M AVG to the culture medium of wild type U2 OS cells, we observed that the cells stopped growing, as shown in FIG. 21A, as they exhibited >60 hrs doubling time. This is not surprising, since the human U2 OS cell contains a functional CLase gene and is not dependent on the presence of L-cysteine/L-cystine in the culture medium. The effect was specific on the CLase pathway, since simultaneous addition of $10^{-4}$ M L-cysteine to the culture medium rescued the cells that continued growing at a normal pace (FIG. 21A, third column). When we analyzed colonies of U2 OS cells that were transfected with the pp23 CLase gene as selection marker, we observed no differences in the average growth rates of the cells (FIG. 21A). Addition of $10^{-5}$ M AVG resulted in a slight delay in the growth rate of these cells (FIG. 21A, most right column). When we analyzed the respective clones for their d2EGFP values, we found that when Zeocin was removed from the culture medium, d2EGFP expression levels dropped to low values (FIG. 21B). This measurement was done in the presence of L-cysteine/L-cystine in the culture medium. In contrast, in the absence of L-cysteine/L-cystine and in the presence of L-cystathionine, in combination with $10^{-5}$ M AVG we observed that the average d2EGFP values remained as high as when Zeocin stayed in the culture medium. This result indicates that inhibition of the endogenous and transfected CLase enzymes leads to a situation in which the cell needs to use the transfected plasmid to increase transcription and thus the amount of functional CLase enzyme. Increased transcription results in d2EGFP expression levels that remain high in the absence of Zeocin in the culture medium. It also warrants survival of the cell, due to sufficient CLase enzyme levels. Taken together, the result indicates the usefulness of the CLase selection marker, even in cells that are not auxotrophic for the CLase enzyme, such as human cells.

The invention claimed is:

1. A nucleic acid construct comprising a multicistronic transcription unit comprising:
   a) a nucleotide sequence encoding a selectable marker functional in a eukaryotic host cell, wherein the selectable marker provides resistance against lethal or growth-inhibitory effects of a selection agent selected from the group consisting of zeocin, puromycin, blasticidin, hygromycin, methotrexate, methionine sulphoximine, and kanamycin or wherein the selectable marker is an auxotrophic selection marker selected from the group consisting of cystathionine gamma-lyase (CLase), dihydrofolate reductase (DHFR) and glutamine synthetase (GS);
   b) a functional open reading frame comprising in a 5' to 3' direction a translation initiation codon, between 90 and 130 amino acid codons, and a translation stop codon, and
   c) a nucleotide sequence coding for a gene product of interest upstream of the functional open reading frame, wherein the stop codon of the functional open reading frame is present between 0 and 300 nucleotides upstream of a translation initiation codon of the nucleotide sequence encoding the selectable marker, wherein the functional open reading frame encodes a non-functional peptide, and wherein the sequence separating the stop codon of the functional open reading frame and the translation initiation codon of the nucleotide sequence encoding the selectable marker is devoid of translation initiation codons.

2. The nucleic acid construct according to claim 1, wherein at least one of the initiation codons of the nucleotide sequence encoding the selectable marker and the functional open reading frame is an ATG codon.

3. The nucleic acid construct according to claim 1, wherein at least one of the initiation codons of the nucleotide sequence encoding the selectable marker and the functional open reading frame is embedded in a Kozak consensus sequence.

4. The nucleic acid construct according to claim 1, wherein the nucleotide sequence encoding the selectable marker encodes a selectable marker polypeptide comprising a mutation that reduces the activity of the selectable marker polypeptide compared to its wild-type counterpart.

5. The nucleic acid construct according to claim 4, wherein the selectable marker polypeptide with reduced activity is selected from the group consisting of:
   a) a zeocin resistance polypeptide wherein proline at position 9 is changed into a different amino acid, wherein the position is relative to the polypeptide encoded by the sequence of SEQ ID NO: 1;
   b) a zeocin resistance polypeptide wherein valine at position 10 is changed into a different amino acid, wherein the position is relative to the polypeptide encoded by the sequence of SEQ ID NO: 1;
   c) a zeocin resistance polypeptide wherein threonine at position 12 is changed into a different amino acid, wherein the position is relative to the polypeptide encoded by the sequence of SEQ ID NO: 1;
   d) a zeocin resistance polypeptide wherein arginine at position 14 is changed into a different amino acid, wherein the position is relative to the polypeptide encoded by the sequence of SEQ ID NO: 1;
   e) a zeocin resistance polypeptide wherein glutamic acid at position 21 is changed into a different amino acid, wherein the position is relative to the polypeptide encoded by the sequence of SEQ ID NO: 1;
   f) a zeocin resistance polypeptide wherein phenylalanine at position 22 is changed into a different amino acid, wherein the position is relative to the polypeptide encoded by the sequence of SEQ ID NO: 1;
   g) a zeocin resistance polypeptide wherein aspartic acid at position 25 is changed into a different amino acid, wherein the position is relative to the polypeptide encoded by the sequence of SEQ ID NO: 1;
   h) a zeocin resistance polypeptide wherein glycine at position 28 is changed into a different amino acid, wherein the position is relative to the polypeptide encoded by the sequence of SEQ ID NO: 1;
   i) a zeocin resistance polypeptide wherein phenylalanine at position 33 is changed into a different amino acid, wherein the position is relative to the polypeptide encoded by the sequence of SEQ ID NO: 1;
   j) a zeocin resistance polypeptide wherein glutamic acid at position 35 is changed into a different amino acid, wherein the position is relative to the polypeptide encoded by the sequence of SEQ ID NO: 1;
   k) a zeocin resistance polypeptide wherein glutamic acid at position 73 is changed into a different amino acid, wherein the position is relative to the polypeptide encoded by the sequence of SEQ ID NO: 1;
   l) a zeocin resistance polypeptide wherein alanine at position 76 is changed into a different amino acid, wherein the position is relative to the polypeptide encoded by the sequence of SEQ ID NO: 1;
   m) a zeocin resistance polypeptide wherein valine at position 82 is changed into a different amino acid, wherein the position is relative to the polypeptide encoded by the sequence of SEQ ID NO: 1;
   n) a zeocin resistance polypeptide wherein aspartic acid at position 88 is changed into a different amino acid, wherein the position is relative to the polypeptide encoded by the sequence of SEQ ID NO: 1; and o) a zeocin resistance polypeptide wherein methionine at position 94 is changed into a different amino acid, wherein the position is relative to the polypeptide encoded by the sequence of SEQ ID NO: 1.

6. The nucleic acid construct according to claim 5, wherein the selectable marker polypeptide with reduced activity is selected from the group consisting of:
   a) a zeocin resistance polypeptide wherein proline at position 9 is changed into cysteine, glutamine or threonine;
   b) a zeocin resistance polypeptide wherein valine at position 10 is changed into alanine;
   c) a zeocin resistance polypeptide wherein threonine at position 12 is changed into alanine;
   d) a zeocin resistance polypeptide wherein arginine at position 14 is changed into proline;
   e) a zeocin resistance polypeptide wherein glutamic acid at position 21 is changed into glycine;
   f) a zeocin resistance polypeptide wherein phenylalanine at position 22 is changed into tyrosine;
   g) a zeocin resistance polypeptide wherein aspartic acid at position 25 is changed into glycine;
   h) a zeocin resistance polypeptide wherein glycine at position 28 is changed into arginine;
   i) a zeocin resistance polypeptide wherein phenylalanine at position 33 is changed into leucine;
   j) a zeocin resistance polypeptide wherein glutamic acid at position 35 is changed into glycine;
   k) a zeocin resistance polypeptide wherein glutamic acid at position 73 is changed into glycine or lysine;
   l) a zeocin resistance polypeptide wherein alanine at position 76 is changed into threonine;
   m) a zeocin resistance polypeptide wherein valine at position 82 is changed into glutamic acid;
   n) a zeocin resistance polypeptide wherein aspartic acid at position 88 is changed into glycine; and
   o) a zeocin resistance polypeptide wherein methionine at position 94 is changed into valine.

7. The nucleic acid construct according to claim 6, wherein the selectable marker polypeptide with reduced activity is selected from the group consisting of:
   a) a zeocin resistance polypeptide wherein at least one of valine at position 10 is changed into alanine, threonine at position 12 is changed into alanine, and glutamic acid at position 35 is changed into glycine;
   b) a zeocin resistance polypeptide wherein at least one of arginine at position 14 is changed into proline, glutamic acid at position 73 is changed into lysine, and aspartic acid at position 88 is changed into glycine;
   c) a zeocin resistance polypeptide wherein at least one of glutamic acid at position 21 is changed into glycine, and alanine at position 76 is changed into threonine;
   d) a zeocin resistance polypeptide wherein at least one of glycine at position 28 is changed into arginine, and glutamic acid at position 73 is changed into glycine; and
   e) a zeocin resistance polypeptide wherein at least one of phenylalanine at position 22 is changed into tyrosine, and aspartic acid at position 25 is changed into glycine.

8. An expression cassette comprising a nucleic acid construct according to claim 1, wherein the expression cassette comprises a promoter operably linked to the multicistronic transcription unit and a transcription termination sequence downstream of the multicistronic transcription unit, and wherein the promoter is functional in a eukaryotic host cell for initiating transcription of the multicistronic transcription unit.

9. An expression vector comprising an expression cassette according to claim 8.

10. An isolated eukaryotic host cell comprising a nucleic acid construct according to claim 1.

11. The nucleic acid construct according to claim 1, wherein the selectable marker is DHFR.

12. A method of generating an in vitro eukaryotic host cell for expression of a gene product of interest, wherein the method comprises the steps of:
   a) introducing into a plurality of in vitro eukaryotic host cells an expression vector according to claim 9;
   b) culturing the plurality of host cells obtained in a) under conditions selecting for expression of the selectable marker; and
   c) selecting at least one host cell expressing the selectable marker for expression of the gene product of interest.

13. A method of expressing a gene product of interest, comprising culturing an in vitro eukaryotic host cell comprising an expression vector according to claim 9, and expressing the gene product of interest from the expression vector, and optionally further comprising recovering or harvesting the gene product of interest.

14. The method according to claim 13, wherein the nucleotide sequence encoding the selectable marker encodes an auxotrophic marker selected from the group consisting of CLase, DHFR and GS, and wherein the host cell is cultured under conditions selective for expression of the auxotrophic marker.

* * * * *